United States Patent
Lee et al.

(10) Patent No.: US 9,403,885 B2
(45) Date of Patent: Aug. 2, 2016

(54) WNT COMPOSITIONS AND THERAPEUTIC USES OF SUCH COMPOSITIONS

(75) Inventors: Tom Tong Lee, San Diego, CA (US); Monica Hayhurst Bennett, San Diego, CA (US); Michael J. Fitch, Carlsbad, CA (US); Peter Flynn, San Diego, CA (US)

(73) Assignee: Fate Therapeutics, Inc., San Diego, CA (US)

(*) Notice: Subject to any disclaimer, the term of this patent is extended or adjusted under 35 U.S.C. 154(b) by 65 days.

(21) Appl. No.: 13/979,368

(22) PCT Filed: Jan. 11, 2012

(86) PCT No.: PCT/US2012/020984
§ 371 (c)(1),
(2), (4) Date: Feb. 3, 2014

(87) PCT Pub. No.: WO2012/097093
PCT Pub. Date: Jul. 19, 2012

(65) Prior Publication Data
US 2014/0142046 A1    May 22, 2014

Related U.S. Application Data

(60) Provisional application No. 61/431,701, filed on Jan. 11, 2011.

(51) Int. Cl.
C07K 14/47 (2006.01)
C07K 14/475 (2006.01)
A61K 38/18 (2006.01)

(52) U.S. Cl.
CPC .......... *C07K 14/47* (2013.01); *A61K 38/18* (2013.01); *C07K 14/475* (2013.01); *C07K 2319/00* (2013.01); *C07K 2319/02* (2013.01); *C07K 2319/21* (2013.01); *C07K 2319/40* (2013.01); *C07K 2319/41* (2013.01); *C07K 2319/42* (2013.01); *C07K 2319/43* (2013.01); *C07K 2319/50* (2013.01)

(58) Field of Classification Search
CPC ...... A61K 38/18; C07K 14/47; C07K 14/475; C07K 2319/02; C07K 2319/00; C07K 2319/50; C07K 2319/40
See application file for complete search history.

(56) References Cited

U.S. PATENT DOCUMENTS 4,751,180 A    6/1988    Cousens et al.
4,935,233 A    6/1990    Bell et al.

FOREIGN PATENT DOCUMENTS

WO    WO 2013/040309 A2    3/2013

OTHER PUBLICATIONS

Willert et al., Nature. May 22, 2003;423(6938):448-452.*
Anakwe et al., "Wnt signalling regulates myogenic differentiation in the developing avian wing", *Development*, 130(15): 3503-3514 (2003).
Australia Application No. 2012205583, Examination Report dated Dec. 5, 2014.
Australia Application No. 2012205583, Examination Report dated May 11, 2015.
Bird et al.,"Single-chain antigen-binding proteins", *Science*, 242: 423-426 (1988).
Bodine et al., "Akt/mTOR pathway is a crucial regulator of skeletal muscle hypertrophy and can prevent muscle atrophy in vivo", *Nature Cell Biology*, 3: 1014-1019 (2001).
Bönnemann, "Beyond dystrophin: current progress in the muscular dystrophies", C. G. et al., *Curr. Opin. Ped.*, 8(6): 569-582 (1996).
Borello et al., "The Wnt/β-catenin pathway regulates Gli-mediated Myf5 expression during somitogenesis", *Development*, 133: 3723-3732 (2006).
Brack et al., "A Temporal Switch from Notch to Wnt Signaling in Muscle Stem Cells Is Necessary for Normal Adult Myogenesis", *Cell Stem Cell*, 2: 50-59 (2008).
Brown, R.H., Jr., "Dystrophin-associated proteins and the muscular dystrophies", *Annu. Rev. Med.*, 48: 457-466 (1997).
Burrus et al., "Biochemical analysis of murine Wnt proteins reveals both shared and distinct properties", *Exp Cell Res.*, 220(2): 363-373 (1995).
Chargé and Rudnicki, "Cellular and molecular regulation of muscle regeneration", *Physiol Rev.*, 84(1): 209-238 (2004).
Chaudhary et al., "A rapid method of cloning functional variable-region antibody genes in *Escherichia coli* as single-chain immunotoxins",*Proc. Natl. Acad. Sci. U.S.A.*, 87: 1066-1070 (1990).
Chen et al., "Protein kinase a signalling via CREB controls myogenesis induced by Wnt proteins", *Nature*, 433: 317-322 (2005).
Ching et al. "Lipid-independent Secretion of a *Drosophila* Wnt Protein", *Journal of Biological Chemistry*, 283(25): 17092-17098 (2008).
Ciciliot and Schiaffino, "Regeneration of mammalian skeletal muscle. Basic mechanisms and clinical implications", *Current Pharmaceutical Design*, 16(8): 906-914 (2010).
Clevers, Hans, "Wnt/β-Catenin Signaling in Development and Disease", *Cell*, 127: 469-480 (2006).
De Vos et al., "Human growth hormone and extracellular domain of its receptor: crystal structure of the complex", *Science*, 255:306-312 (1992).
Dierick and Bejsovec, "Cellular Mechanisms of Wingless/Wnt Signal Transduction", *Current Topics in Developmental Biology*, 43: 153-178 (1999).

(Continued)

*Primary Examiner* — Daniel C Gamett
(74) *Attorney, Agent, or Firm* — Cooley LLP

(57) ABSTRACT

The invention provides novel Wnt polypeptides that have enhanced solubility and improved biologic drug-like properties, and polynucleotides encoding the Wnt polypeptides of the invention. The Wnt polypeptides of the invention can be used therapeutically, such as, for example, in methods of preventing or treating muscle loss and/or promoting muscle hypertrophy and growth.

18 Claims, 16 Drawing Sheets

(56) References Cited

OTHER PUBLICATIONS

Doubravska et al. "Fatty acid modification of Wnt1 and Wnt3a at serine is prerequisite for lipidation at cysteine and is essential for Wnt signalling", *Cellular Signalling*, 23(5): 837-848 (2011).
European Application No. 12734079.2, Partial European Search Report Dec. 5, 2014.
European Application No. 12734079.2, Extended European Search Report dated Apr. 2, 2015.
Fisher and Upadhyaya, "Molecular genetics of facioscapulohumeral muscular dystrophy (FSHD)", *Neuromuscular Disorders*, 7(1): 55-62 (1997).
Franch-Marro et al., "Wingless secretion requires endosome-to-Golgi retrieval of Wntless/Evi/Sprinter by the retromer complex", *Nature Cell Biology*, 10(2): 170-177 (2008). Published online: Jan. 13, 2008.
Funakoshi et al., "Emerin and cardiomyopathy in Emery-Dreifuss muscular dystrophy", *Neuromuscular Disorders*, 9(2): 108-114 (1999).
Galli and Burrus, "Differential Palmit(e)oylation of Wnt1 on C93 and S224 Residues Has Overlapping and Distinct Consequences", *PLoS One*, 6(10): e26636, pp. 1-17 (2011).
Glass et al., "Signalling pathways that mediate skeletal muscle hypertrophy and atrophy", *Nature Cell Biology*, 5: 87-90 (2003).
Gros et al., "WNT11 acts as a directional cue to organize the elongation of early muscle fibres", *Nature*, 457: 589-593 (2009).
Hoffman et al., "Characterization of dystrophin in muscle-biopsy specimens from patients with Duchenne's or Becker's muscular dystrophy", *N. Engl. J. Med.*, 318(21): 1363-1368 (1988).
Huston et al., "Protein engineering of antibody binding sites: recovery of specific activity in an anti-digoxin single-chain Fv analogue produced in *Escherichia coli*", *Proc. Natl. Acad. Sci. U.S.A.*, 85: 5879-5883 (1988).
Kadowaki et al., "The segment polarity gene porcupine encodes a putative multitransmembrane protein involved in Wingless processing", *Genes Development*, 10: 3116-3128 (1996).
Komekado, H. et al. "Glycosylation and palmitoylation of Wnt-3a are coupled to produce an active form of Wnt-3a", *Genes to Cells*, 12(4): 521-534 (2007).
Kuang et al., Niche Regulation of Muscle Satellite Cell Self-Renewal and Differentiation, *Cell Stem Cell*, 2: 22-31 (2008).
Kurayoshi et al. "Post-translational palmitoylation and glycosylation of Wnt-5a are necessary for its signalling", *Biochem J.*, 402(3): 515-523 (2007).
Le Grand et al., "Wnt7a activates the planar cell polarity pathway to drive the symmetric expansion of satellite stem cells", *Cell Stem Cell*, 4: 535-547 (2009).
Lim et al., "The sarcoglycan complex in limb-girdle muscular dystrophy", *Current Opinion in Neurology*, 11(5): 443-452 (1998).
Maratea et al., "Deletion and fusion analysis of the phage phi X174 lysis gene E", *Gene*, 40: 39-46 (1985).
Mason et al., "Mutational analysis of mouse Wnt-1 identifies two temperature-sensitive alleles and attributes of Wnt-1 protein essential for transformation of a mammary cell line", *Mol. Biol. Cell*, 3: 521-533 (1992).
Murphy et al., "Genetic construction, expression, and melanoma-selective cytotoxicity of a diphtheria toxin-related alpha-melanocyte-stimulating hormone fusion protein", *Proc. Natl. Acad. Sci. USA*, 83: 8258-8262 (1986).
Nusse, R., "Wnts and Hedgehogs: lipid-modified proteins and similarities in signaling mechanisms at the cell surface", *Development*, 130: 5297-5305 (2003).

PCT Application No. PCT/US2012/020984, International Search Report and Written Opinion, mailed Jul. 30, 2012.
PCT Application No. PCT/US2012/020984, International Preliminary Report on Patentability, dated Jul. 16, 2013.
Polesskaya et al, "Wnt signaling induces the myogenic specification of resident CD45+ adult stem cells during muscle regeneration", *Cell*, 113(7): 841-52 (2003).
Rochat et al., "Insulin and Wnt1 Pathways Cooperate to Induce Reserve Cell Activation in Differentiation and Myotube Hypertrophy", *Molecular Biology of the Cell*, 15: 4544-4555 (2004).
Smith et al., "Human interleukin 4. The solution structure of a four-helix bundle protein", *J. Mol. Biol.*, 224: 899-904 (1992).
Smolich et al., "Wnt family proteins are secreted and associated with the cell surface", *Molecular Biology of the Cell*, 4(12): 1267-1275 (1993).
Tajbakhsh et al., "Differential activation of Myf5 and MyoD by different Wnts in explants of mouse paraxial mesoderm and the later activation of myogenesis in the absence of Myf5", *Development*, 125: 4155-4162 (1998).
Takada et al. "Monounsaturated Fatty Acid Modification of Wnt Protein: Its Role in Wnt Secretion", *Developmental Cell*, 11(6): 791-801 (2006).
Tanaka et al. "*Drosophila* segment polarity gene product porcupine stimulates the posttranslational N-glycosylation of wingless in the endoplasmic reticulum", *J. Biol. Chem.*, 277: 12816-12823 (2002).
Torrente et al., "Human circulating AC133+ stem cells restore dystrophin expression and ameliorate function in dystrophic skeletal muscle", *The Journal of Clinical Investigation*, 114(2): 182-195 (2004).
Uhlman and Peyman, "Antisense Oligonucleotides: A New Therapeutic Principle", *Chemical Reviews*, 90(4): 544-584 (1990).
Van Den Heuvel et al., "Mutations in the segment polarity genes wingless and porcupine impair secretion of the wingless protein", 12(13): 5293-5302 (1993).
Voit, T., "Congenital muscular dystrophies: 1997 update", *Brain Development*, 20(2): 65-74.
Von Maltzahn et al., "Wnt7a-Fzd7 signalling directly activates the Akt/mTOR anabolic growth pathway in skeletal muscle", *Nature Cell Biology*, 14(2): 186-191 (2011).
Wodarz and Nusse, "Mechanisms of Wnt signaling in development", *Annu. Rev. Cell. Dev. Biol.*, 14: 59-88 (1998).
Worton, R., "Muscular dystrophies: diseases of the dystrophin-glycoprotein complex", *Science*, 270: 755-756 (1995).
Zhai et al., "*Drosophila* Wnt-1 Undergoes a Hydrophobic Modification and Is Targeted to Lipid Rafts, a Process That Requires Porcupine", *The Journal of Biological Chemistry*, 279(32): 33220-33227 (2004).
Alland, L. et al. "Dual myristylation nad palmitylation of Src family member p59fyn affects subcellular localization" *Journal of Biological Chemistry* 269:16701-16705 (1994).
Crise et al., "Identification of palmitoylation sites on CDR, the Human Immunodeficiency Virus receptor" *Journal of Biological Chemistry* 267: 13593-13597 (1992).
O'Dowd et al., "Palmitoylation of the human beta 2 adrenergic receptor" *Journal of Biological Chemistry* 269: 7564-7569 (1989).
Resh, M.A. "Fatty acylation of proteins: new insights into membrane targeting of myristoylated and palmitoylated proteins" *Biochimica et Biophysica Acta* 1451:1-16 (1999).
Zusinaite et al., "Mutations at the palmitoylation site of non-structural protein nsP1 of Semliki Forest virus attenuate virus replication and cause accumulation of compensatory mutations" *Journal of General Virology* 88: 1977-1985 (2007).

\* cited by examiner

```
Wnt-1      --------MGLWALLPGW----------------VSATLLLALAALPAALA  27
Wnt-2      ----------MNAPLG------------------GIWLWLPLLLTWLTP    21
Wnt-2b     ---------MLDGLGVV--------------AISIFGIQLKTEGSLRTAVP  28
Wnt-3      --------------MEPH------------------LLGLLLGLLLGGTRVLA 21
Wnt-3a     ---------------MAP-------------------LGYFL-LLCSLKQALG 18
Wnt-4      --------------MSPR------------------SCLRSLRLLVFAVFSAA 21
Wnt-5a     ---------MKKSIGILSPGVALGMAGSAMSSKFFLVALAIFFSFAQVVI    41
Wnt-5b     -----------------------------------MPSLLLLFTAALLSSWAQLLT 21
Wnt-6      -----------------------------------MLPPLPSRLGLLLLLL  16
Wnt-7a     ---------MNRKARRC-----------------LGHLFLSLG--MVYLRI  23
Wnt-7b     ---------MHRNFRKW-----------------IFYVFLCFG--VLYVKL  23
Wnt-8a     --------------------------------MGNLFMLWAALGIC---C  15
Wnt-8      -------------------------------MFLSKPSVYICLFTC      15
Wnt-9a     -------------------------MLDGSPLARWLAAAFGLTLLLA     22
Wnt-9b     --------------------------MR--PPPALALAGLC----LLA    16
Wnt-10a    MGSAHPRP-----------------WLRLRPQPQPRPALWVLLFFLL     30
Wnt-10b    ------------------------MLEEPRPRPPPSGLAGLLFLA       21
Wnt-11     -------------------------------MRARPQVCEALLFAL      15
Wnt-16     ---------MDRAALLG-----------------LARLCALWAALLVLFPY 25

Wnt-1      ANSSGRWWGIVNVASSTNLLTD--------SKSLQLVLEPSLQLLSRKQRR 70
Wnt-2      EVNSSWWY--------MRATGGS-----------SRVMCDNVPGLVSSQRQ 53
Wnt-2b     GIPTQSAFNKC---LQRYIGAL--------G----ARVICDNIPGLVSRQRQ 65
Wnt-3      GYP--IWWSLALGQQYTSLGS-----------QPLLCGSIPGLVPKQLR   57
Wnt-3a     SYP--IWWSLAVGPQYSSLGS-----------QPILCASIPGLVPKQLR   54
Wnt-4      ASN---WLYLAKLSSVGSISE-----------EETCEKLKGLIQRQVQ    55
Wnt-5a     EANSWWSLGMNNPVQMSEVYII---------G----AQPLCSQLAGLSQGQKK 81
Wnt-5b     DANSWWSLALN-PVQRPEMFII---------G----AQPVCSQLPGLSPGQRK 60
Wnt-6      LCPAHVGG------LWWAVGSP--------LVMDPTSICRKARRLAGRQAE 53
Wnt-7a     GGFSSVVA------LGAS---------------IICNKIPGLAPRQRA   50
Wnt-7b     GALSSVVA------LGAN---------------IICNKIPGLAPRQRA   50
Wnt-8a     AAFSASAWS------------------------------VNNFLIT     31
Wnt-8      VLQLSHSWS------------------------------VNNFLMT     31
Wnt-9a     ALRPSAAYFGLTGSEPLTILP--LTLEPEAAAQAHYKACDRLKLERKQRR 70
Wnt-9b     LPAAAASYFGLTGREVLTPFPGLGTAAAPAQGGAHLKQCDLLKLSRRQKQ 66
Wnt-10a    LLAAAMPRSAPNDILDLRLPPE-------PVLNANTVCLTLPGLSRRQME 73
Wnt-10b    LCSRALS----NEILGLKLPGE-------PPLTANTVCLTLSGLSKRQLG 60
Wnt-11     ALQTGVCYGIKWLALSKTPSAL--------ALN-QTQHCKQLEGLVSAQVQ 57
Wnt-16     GAQGNWMW------LGIASFGV-------P---EKLGCANLP-LNSRQKE 58

Wnt-1      LIRQNPGILHSVSGGLQSAVRECKWQFRNRRWNCP-------TAPG-PHL 112
Wnt-2      LCHRHPDVMRAISQGVAEWTAECQHQFRQHRWNCN--------TLDRDHSL 96
Wnt-2b     LCQRYPDIMRSVGEGAREWIRECQHQFRHHRWNCT--------TLDRDHTV 108
Wnt-3      FCRNYIEIMPSVAEGVKLGIQECQHQFRGRRWNCT-------TIDDSLAI 100
Wnt-3a     FCRNYVEIMPSVAEGIKIGIQECQHQFRGRRWNCT-------TVHDSLAI 97
Wnt-4      MCKRNLEVMDSVRRGAQLAIEECQYQFRNRRWNCS-------TLDS-LPV 97
Wnt-5a     LCHLYQDHMQYIGEGAKTGIKECQYQFRHRRWNCS-------TVD-NTSV 123
Wnt-5b     LCQLYQEHMAYIGEGAKTGIKECQHQFRQRRWNCS-------TAD-NASV 102
Wnt-6      LCQAEPEVVAELARGARLGVRECQFQFRFRRWNCS-----SHS-----KA 93
```

FIG. 1

```
Wnt-7a    ICQSRPDAIIVIGEGSQMGLDECQFQFRNGRWNCS--------ALGERTV  92
Wnt-7b    ICQSRPDAIIVIGEGAQMGINECQYQFRFGRWNCS--------ALGEKTV  92
Wnt-8a    GPKAYLTYTTSVALGAQSGIEECKFQFAWERWNCP--------ENALQLS  73
Wnt-8     GPKAYLIYSSSVAAGAQSGIEECKYQFAWDRWNCP--------ERALQLS  73
Wnt-9a    MCRRDPGVAETLVEAVSMSALECQFQFRFERWNCT---------LEGRY  110
Wnt-9b    LCRREPGLAETLRDAAHLGLLECQFQFRHERWNCS---------LEG--  104
Wnt-10a   VCVRHPDVAASAIQGIQIAIHECQHQFRDQRWNCS-----SLETRNKIPY 118
Wnt-10b   LCLRNPDVTASALQGLHIAVHECQHQLRDQRWNCS-----ALEGGGRLPH 105
Wnt-11    LCRSNLELMHTVVHAAREVMKACRRAFADMRWNCS--------SIELAPN  99
Wnt-16    LCKRKPYLLPSIREGARLGIQECGSQFRHERWNCMITAAATTAPMGASPL 108

Wnt-1     FGKIVNRGCRETAFIFAITSAGVTHSVARSCSEGSIESCTCDYRRRGPG- 161
Wnt-2     FGRVLLRSSRESAFVYAISSAGVVFAITRACSQGEVKSCSCDPKKMGSAK 146
Wnt-2b    FGRVMLRSSREAAFVYAISSAGVVHAITRACSQGELSVCSCDPYTRGRHH 158
Wnt-3     FGPVLDKATRESAFVHAIASAGVAFAVTRSCAEGTSTICGCDSHHKGPP- 149
Wnt-3a    FGPVLDKATRESAFVHAIASAGVAFAVTRSCAEGTAAICGCSSRHQGSP- 146
Wnt-4     FGKVVTQGTREAAFVYAISSAGVAFAVTRACSSGELEKCGCDRTVHGVS- 146
Wnt-5a    FGRVMQIGSRETAFTYAVSAAGVVNAMSRACREGELSTCGCS--RAARPK 171
Wnt-5b    FGRVMQIGSRETAFTHAVSAAGVVNAISRACREGELSTCGCS--RTARPK 150
Wnt-6     FGRILQQDIRETAFVFAITAAGASHAVTQACSMGELLQCGCQAPRG---- 139
Wnt-7a    FGKELKVGSREAAFTYAIIAAGVAHAITAACTQGNLSDCGCDKEKQGQYH 142
Wnt-7b    FGQELRVGSREAAFTYAITAAGVAHAVTAACSQGNLSNCGCDREKQGYYN 142
Wnt-8a    THNRLRSATRETSFIHAISSAGVMYIITKNCSMGDFENCGCDGSNNGKTG 123
Wnt-8     SHGGLRSANRETAFVHAISSAGVMYTLTRNCSLGDFDNCGCDDSRNGQLG 123
Wnt-9a    RASLLKRGFKETAFLYAISSAGLTHALAKACSAGRMERCTCDEAPDLENR 160
Wnt-9b    RMGLLKRGFKETAFLYAVSSAALTHTLARACSAGRMERCTCDDSPGLESR 154
Wnt-10a   ESPIFSRGFRESAFAYAIAAAGVVHAVSNACALGKLKACGCDASRRGDEE 168
Wnt-10b   HSAILKRGFRESAFSFSMLAAGVMHAVATACSLGKLVSCGCGWKGSGEQD 155
Wnt-11    YLLDLERGTRESAFVYALSAAAISHAIARACTSGDLPGCSCGPVPGEPP- 148
Wnt-16    FGYELSSGTKETAFIYAVMAAGLVHSVTRSCSAGNMTECSCDTTLQNGGS 158

Wnt-1     ---------------------------------------GPDWHWGGCSDNI 174
Wnt-2     D--------------------------------------SKGIFDWGGCSDNI 161
Wnt-2b    D--------------------------------------QRGDFDWGGCSDNI 173
Wnt-3     ---------------------------------------GEGWKWGGCSEDA 162
Wnt-3a    ---------------------------------------GKGWKWGGCSEDI 159
Wnt-4     ---------------------------------------PQGFQWSGCSDNI 159
Wnt-5a    D--------------------------------------LPRDWLGGCGDNI 186
Wnt-5b    D--------------------------------------LPRDWLGGCGDNV 165
Wnt-6     -----------RAPPRPSGLP-GTPGP-PGPAGSPEGSAAWEWGGCGDDV 176
Wnt-7a    R--------------------------------------DEG-WKWGGCSADI 156
Wnt-7b    Q--------------------------------------AEG-WKWGGCSADV 156
Wnt-8a    ---------------------------------------GHGWIWGGCSDNV 136
Wnt-8     ---------------------------------------GQGWLWGGCSDNV 136
Wnt-9a    E--------------------------------------AWQWGGCGDNL 172
Wnt-9b    Q--------------------------------------AWQWGVCGDNL 166
Wnt-10a   AFRRKLHRLQLDALQRGKGLSHGVPEHPALPTASPGLQDSWEWGGCSPDM 218
Wnt-10b   RLRAKL---LQLQALSRGKSFPHSLPSPGPGSSPSPGPQDTWEWGGCNHDM 203
Wnt-11    ---------------------------------------GPGNRWGGCADNL 161
Wnt-16    A--------------------------------------SEG-WHWGGCSDDV 172

Wnt-1     DFGRLFGREFVDSGEKGR--------DLRFLMNLHNNEAGRTTVFSEMRQ 216
```

*FIG. 1 (Continued)*

```
Wnt-2    DYGIKFARAFVDAKERKG-------KDARALMNLHNNRAGRKAVKRFLKQ 204
Wnt-2b   HYGVRFAKAFVDAKEKRL-------KDARALMNLHNNRCGRTAVRRFLKL 216
Wnt-3    DFGVLVSREFADARENRP--------DARSAMNKHNNEAGRTTILDHMHL 204
Wnt-3a   EFGGMVSREFADARENRP--------DARSAMNRHNNEAGRQAIASHMHL 201
Wnt-4    AYGVAFSQSFVDVRERSKG-----ASSSRALMNLHNNEAGRKAILTHMRV 204
Wnt-5a   DYGYRFAKEFVDARERERIHAKGSYESARILMNLHNNEAGRRTVYNLADV 236
Wnt-5b   EYGYRFAKEFVDAREREKNFAKGSEEQGRVLMNLQNNEAGRRAVYKMADV 215
Wnt-6    DFGDEKSRLFMDARHKRG------RGDIRALVQLHNNEAGRLAVRSHTRT 220
Wnt-7a   RYGIGFAKVFVDAREIKQN---ART-----LMNLHNNEAGRKILEENMKL 198
Wnt-7b   RYGIDFSRRFVDAREIKKN---ARR-----LMNLHNNEAGRKVLEDRMQL 198
Wnt-8a   EFGERISKLFVDSLEKGKD--------ARALMNLHNNRAGRLAVRATMKR 178
Wnt-8    GFGEAISKQFVDALETGQD--------ARAAMNLHNNEAGRKAVKGTMKR 178
Wnt-9a   KYSSKFVKEFLG-RRSSKD--------LRARVDFHNNLVGVKVIKAGVET 213
Wnt-9b   KYSTKFLSNFLGSKRGNKD--------LRARADAHNTHVGIKAVKSGLRT 208
Wnt-10a  GFGERFSKDFLDSREP--------HRDIHARMRLHNNRVGRQAVMENMRR 260
Wnt-10b  DFGEKFSRDFLDSREA--------PRDIQARMRIHNNRVGRQVVTENLKR 245
Wnt-11   SYGLLMGAKFSDAPMKVKKTG----SQANKLMRLHNSEVGRQALRASLEM 207
Wnt-16   QYGMWFSRKFLDFPIGNTT---GKENKVLLAMNLHNNEAGRQAVAKLMSV 219

Wnt-1    ECKCHGMSGSCTVRTCWMRLPTLRAVGDVLRDRFDGASRVLYGNRGSNRA 266
Wnt-2    ECKCHGVSGSCTLRTCWLAMADFRKTGDYLWRKYNGAIQVVMNQ---DGT 251
Wnt-2b   ECKCHGVSGSCTLRTCWRALSDFRRTGDYLRRRYDGAVQVMATQ---DGA 263
Wnt-3    KCKCHGLSGSCEVKTCWWAQPDFRAIGDFLKDKYDSASEMVVEK----HRE 251
Wnt-3a   KCKCHGLSGSCEVKTCWWSQPDFRAIGDFLKDKYDSASEMVVEK----HRE 248
Wnt-4    ECKCHGVSGSCEVKTCWRAVPPFRQVGHALKEKFDGATEVEPRR----VGS 251
Wnt-5a   ACKCHGVSGSCSLKTCWLQLADFRKVGDALKEKYDSAAAMRLNS----RGK 283
Wnt-5b   ACKCHGVSGSCSLKTCWLQLAEFRKVGDRLKEKYDSAAAMRVTR----KGR 262
Wnt-6    ECKCHGLSGSCALRTCWQKLPPFREVGARLLERFHGASRVMGTN----DGK 267
Wnt-7a   ECKCHGVSGSCTTKTCWTTLPQFRELGYVLKDKYNEAVHVEPVR---ASR 245
Wnt-7b   ECKCHGVSGSCTTKTCWTTLPKFREVGHLLKEKYNAAVQVEVVR---ASR 245
Wnt-8a   TCKCHGISGSCSIQTCWLQLAEFREMGDYLKAKYDQALKIEMDKRQ--LR 226
Wnt-8    TCKCHGVSGSCTTQTCWLQLPEFREVGAHLKEKYHAALKVDLLQG----- 223
Wnt-9a   TCKCHGVSGSCTVRTCWRQLAPFHEVGKHLKHKYETALKVGSTTNEAAGE 263
Wnt-9b   TCKCHGVSGSCAVRTCWKQLSPFRETGQVLKLRYDSAVKVSSATNEALGR 258
Wnt-10a  KCKCHGTSGSCQLKTCWQVTPEFRTVGALLRSRFHRATLIRPHNR--NGG 308
Wnt-10b  KCKCHGTSGSCQFKTCWRAAPEFRAVGAALRERLGRAIFIDTHNR--NSG 293
Wnt-11   KCKCHGVSGSCSIRTCWKGLQELQDVAADLKTRYLSATKVVHRP---MGT 254
Wnt-16   DCRCHGVSGSCAVKTCWKTMSSFEKIGHLLKDKYENSIQISDKT----KRK 266

Wnt-1    SRAELLR-----LEPEDPAHKPPSPHDLVYFEKSPNFCTYSGRLGTAGTA 311
Wnt-2    GFTVAN-----------ERFKKPTKNDLVYFENSPDYCIRDREAGSLGTA 290
Wnt-2b   NFTAAR-----------QGYRRATRTDLVYFDNSPDYCVLDKAAGSLGTA 302
Wnt-3    SRGWVET-----LRAKYSLFKPPTERDLVYYENSPNFCEPNPETGSFGTR 296
Wnt-3a   SRGWVET-----LRPRYTYFKVPTERDLVYYEASPNFCEPNPETGSFGTR 293
Wnt-4    SR----A-----LVPRNAQFKPHTDEDLVYLEPSPDFCEQDMRSGVLGTR 292
Wnt-5a   -LVQVN-----------SRFNSPTTQDLVYIDPSPDYCVRNESTGSLGTQ 321
Wnt-5b   -LELVN-----------SRFTQPTPEDLVYVDPSPDYCLRNESTGSLGTQ 300
Wnt-6    ALLPAVR----------TLKPPGRADLLYAADSPDFCAPNRRTGSPGTR 306
Wnt-7a   NKRPTFL-----KIKKPLSYRKPMDTDLVYIEKSPNYCEEDPVTGSVGTQ 290
Wnt-7b   LRQPTFL-----RIKQLRSYQKPMETDLVYIEKSPNYCEEDAATGSVGTQ 290
Wnt-8a   AGNSAEG-----HWVPAEAFLPSAEAELIFLEESPDYCTCNSSLGIYGTE 271
Wnt-8    AGNSAAG-----RGAIADTFRSISTRELVHLEDSPDYCLENKTLGLLGTE 268
```

*FIG. 1 (Continued)*

```
Wnt-9a      AGAISPPRGR--ASGAGGSDPLPRTPELVHLDDSPSFCLAGR--FSPGTA  309
Wnt-9b      LELWAPAR-----QGSLTKGLAPRSGDLVYMEDSPSFCRPSK--YSPGTA  301
Wnt-10a     QLEPGPAGAPSPAPGAPGPRRRASPADLVYFEKSPDFCEREPRLDSAGTV  358
Wnt-10b     AFQPRLR------------PRRLSG--ELVYFEKSPDFCERDPTMGSPGTR  330
Wnt-11      RKHLVPK---------DLDIRPVKDSELVYLQSSPDFCMKNEKVGSHGTQ  295
Wnt-16      MRR----------REKDQRKIPIHKD-DLLYVNKSPNYCVEDKKLGIPGTQ  306

Wnt-1       GRACNSSSPALDGCELLCCGRGHRTRTQRVTER-------CNCTFHWCCH  354
Wnt-2       GRVCNLTSRGMDSCEVMCCGRGYDTSHVTRMTK-------CGCKFHWCCA  333
Wnt-2b      GRVCSKTSKGTDGCEIMCCGRGYDTTRVTRVTQ-------CECKFHWCCA  345
Wnt-3       DRTCNVTSHGIDGCDLLCCGRGHNTRTEKRKEK-------CHCIFHWCCY  339
Wnt-3a      DRTCNVSSHGIDGCDLLCCGRGHNARAERRREK-------CRCVFHWCCY  336
Wnt-4       GRTCNKTSKAIDGCELLCCGRGFHTAQVELAER-------CSCKFHWCCF  335
Wnt-5a      GRLCNKTSEGMDGCELMCCGRGYDQFKTVQTER-------CHCKFHWCCY  364
Wnt-5b      GRLCNKTSEGMDGCELMCCGRGYNQFKSVQVER-------CHCKFHWCCF  343
Wnt-6       GRACNSSAPDLSGCDLLCCGRGHRQESVQLEEN-------CLCRFHWCCV  349
Wnt-7a      GRACNKTAPQASGCDLMCCGRGYNTHQYARVWQ-------CNCKFHWCCY  333
Wnt-7b      GRLCNRTSPGADGCDTMCCGRGYNTHQYTKVWQ-------CNCKFHWCCF  333
Wnt-8a      GRECLQNSHNTSRWERRSCGRLCTECGLQVEERKTEVISSCNCKFQWCCT  321
Wnt-8       GRECLRRGRALGRWERRSCRRLCGDCGLAVEERRAETVSSCNCKFHWCCA  318
Wnt-9a      GRRCHREK----NCESICCGRGHNTQSRVVTRP-------CQCQVRWCCY  348
Wnt-9b      GRVCSREA----SCSSLCCGRGYDTQSRLVAFS-------CHCQVQWCCY  340
Wnt-10a     GRLCNKSSAGSDGCGSMCCGRGHNILRQTRSER-------CHCRFHWCCF  401
Wnt-10b     GRACNKTSRLLDGCGSLCCGRGHNVLRQTRVER-------CHCRFHWCCY  373
Wnt-11      DRQCNKTSNGSDSCDLMCCGRGYNPYTDRVVER-------CHCKYHWCCY  338
Wnt-16      GRECNRTSEGADGCNLLCCGRGYNTHVVRHVER-------CECKFIWCCY  349

Wnt-1       VSCRNCTHTRVLHECL-----------------  370
Wnt-2       VRCQDCLEALDVHTCKAPKNADWTTAT-------  360
Wnt-2b      VRCKECRNTVDVHTCKAPKKAEWLDQT-------  372
Wnt-3       VSCQECIRIYDVHTCK-----------------  355
Wnt-3a      VSCQECTRVYDVHTCK-----------------  352
Wnt-4       VKCRQCQRLVELHTCR-----------------  351
Wnt-5a      VKCKKCTEIVDQFVCK-----------------  380
Wnt-5b      VRCKKCTEIVDQYICK-----------------  359
Wnt-6       VQCHRCRVRKELSLCL-----------------  365
Wnt-7a      VKCNTCSERTEMYTCK-----------------  349
Wnt-7b      VKCNTCSERTEVFTCK-----------------  349
Wnt-8a      VKCDQCRHVVSKYYCARSP----GSAQSLGKGSA  351
Wnt-8       VRCEQCRRRVTKYFCSRAERPRGGAAHKPGRKP-  351
Wnt-9a      VECRQCTQREEVYTCKG----------------  365
Wnt-9b      VECQQCVQEELVYTCKH----------------  357
Wnt-10a     VVCEECRITEWVSVCK-----------------  417
Wnt-10b     VLCDECKVTEWVNVCK-----------------  389
Wnt-11      VTCRRCERTVERYVCK-----------------  354
Wnt-16      VRCRRCESMTDVHTCK-----------------  365
```

*FIG. 1 (Continued)*

Wnt-7A Alignment

```
            10        20        30        40        50        60        70        80
    ---------+---------+---------+---------+---------+---------+---------+---------+
  1 MNRKARRCLGHLFLSLGMVYLRIGGFSSVVALGASIICNKIPGLAPRQRAICQSRPDAIIVIGEGSQMGLDECQFQFRNG Wnt7A_Human
  1 MTRKARRCLGHLFLSLGIVYLRIGGFSSVVALGASIICNKIPGLAPRQRAICQSRPDAIIVIGEGSQMGLDECQFQFRNG Wnt7A_Mouse
  1 MTRKARRCLGHLFLSLGIVYLRIGDFSSVVALGASIICNKIPGLAPRQRAICQSRPDAIIVIGEGSQMGLDECQFQFRNG Wnt7A_Rat
  1 MNRKTRRWIFHIFLSLGIVYIKIGGFSSVVALGASIICNKIPGLAPRQRAICQSRPDAIIVIGEGSQMGINECQFQFRNG Wnt7A_Chicken
  1 MSRKTRRWIFHIFLCLGIIYLKIGGFSSVVALGASIICNKIPGLAPRQRTICQSRPDAIIVIGEGAQMGINECQFQFRNG Wnt7A_Zebrafish
  1 MNRKARRCLGHLFLSLGLVYLRIGGFSSVVALGASIICNKIPGLAPRQRAICQSRPDAIIVIGEGSQMGLDECQFQFRNG Wnt7A_Pig
  1 MNRKARRCLGHLFLSLGMVYLRIGGFSSVVALGASIICNKIPGLAPRQRAICQSRPDAIIVIGEGSQMGLDECQFQFRNG Wnt7A_Cow 90       100       110       120       130       140       150       160
    ---------+---------+---------+---------+---------+---------+---------+---------+
 81 RWNCSALGERTVFGKELKVGSREAAFTYAIIAAGVAHAITAACTQGNLSDCGCDKEKQGQYHRDEGWKWGGCSADIRYGI Wnt7A_Human
 81 RWNCSALGERTVFGKELKVGSREAAFTYAIIAAGVAHAITAACTQGNLSDCGCDKEKQGQYHRDEGWKWGGCSADIRYGI Wnt7A_Mouse
 81 RWNCSALGERTVFGKELKVGSREAAFTYAIIAAGVAHAITAACTQGNLSDCGCDKEKQGQYHRDEGWKWGGCSADIRYGI Wnt7A_Rat
 81 RWNCSALGERTVFGKELKVGSREAAFTYAIIAAGVAHAITAACTQGNLSDCGCDKEKQGQYHKEEGWKWGGCSADIRYGI Wnt7A_Chicken
 81 RWNCSALGERTVFGKELKVGSREAAFTYAIIAAGVAHAITAACTQGTLSGCGCDKEKQGFYNQEEGWKWGGCSADIRYGL Wnt7A_Zebrafish
 81 RWNCSALGERTVFGKELKVGSREAAFTYAIIAAGVAHAITAACTQGNLSDCGCDKEKQGQYHRDEGWKWGGCSADIRYGI Wnt7A_Pig
 81 RWNCSALGERTVFGKELKVGSREAAFTYAIIAAGVAHAITAACTQGNLSDCGCDKEKQGQYHRDEGWKWGGCSADIRYGI Wnt7A_Cow 170       180       190       200       210       220       230       240
    ---------+---------+---------+---------+---------+---------+---------+---------+
161 GFAKVFVDAREIKQNARTLMNLHNNEAGRKILEENMKLECKCHGVSGSCTTKTCWTTLPQFRELGYVLKDKYNEAVHVEP Wnt7A_Human
161 GFAKVFVDAREIKQNARTLMNLHNNEAGRKILEENMKLECKCHGVSGSCTTKTCWTTLPQFRELGYVLKDKYNEAVHVEP Wnt7A_Mouse
161 GFAKVFVDAREIKQNARTLMNLHNNEAGRKILEENMKLECKCHGVSGSCTTKTCWTTLPQFRELGYVLKDKYNEAVHVEP Wnt7A_Rat
161 GFAKVFVDAREIKQNARTLMNLHNNEAGRKILEENMKLECKCHGVSGSCTTRTCWTTLPKFRELGYILKDKYNEAVQVEP Wnt7A_Chicken
161 SFSKVFVDAREIKQNARTLMNLHNNEVGRKILEENMKLECKCHGVSGSCTTKTCWTTLPQFRQLGYILKERYNHAVHVEP Wnt7A_Zebrafish
161 GFAKVFVDAREIKQNARTLMNLHNNEAGRKILEENMKLECKCHGVSGSCTTKTCWTTLPQFRELGYVLKDKYNEAVHVEP Wnt7A_Pig
161 GFAKVFVDAREIKQNARTLMNLHNNEAGRKILEENMKLECKCHGVSGSCTTKTCWTTLPQFRELGYVLKDKYNEAVHVEP Wnt7A_Cow 250       260       270       280       290       300       310       320
    ---------+---------+---------+---------+---------+---------+---------+---------+
241 VRASRNKRPTFLKIKKPLSYRKPMDTDLVYIEKSPNYCEEDPVTGSVGTQGRACNKTAPQASGCDLMCCGRGYNTHQYAR Wnt7A_Human
241 VRASRNKRPTFLKIKKPLSYRKPMDTDLVYIEKSPNYCEEDPVTGSVGTQGRACNKTAPQASGCDLMCCGRGYNTHQYAR Wnt7A_Mouse
241 VRASRNKRPTFLKIKKPLSYRKPMDTDLVYIEKSPNYCEEDPVTGSVGTQGRACNKTAPQASGCDLMCCGRGYNTHQYAR Wnt7A_Rat
241 VRASRNKRPTFLKIKKPLSYRKPMDTDLVYIEKSPNYCEEDPVTGSVGTQGRMCNKTAQQSNGCDLMCCGRGYNTHQYSR Wnt7A_Chicken
241 VRASRNKRPAFLKVKKPYSYRKPMDTDLVYIEKSPNYCEADPVTGSMGTQGRICNKTAQHTNGCDLMCCGRGYNTHQYSR Wnt7A_Zebrafish
241 VRASRNKRPTFLKIKKPLSYRKPMDTDLVYIEKSPNYCEEDPVTGSVGTQGRACNKTAPQASGCDLMCCGRGYNTHQYAR Wnt7A_Pig
241 VRASRNKRPAFLKIKKPLSYRKPMDTELVYIEKSPSYCEEDPATGSVGTQGRACNKTAPQASGCDLMCCGRGYNTHQYAR Wnt7A_Cow 330       340
    ---------+---------+
321 VWQCNCKFHWCCYVKCNTCSERTEMYTCK              Wnt7A_Human
321 VWQCNCKFHWCCYVKCNTCSERTEMYTCK              Wnt7A_Mouse
321 VWQCNCKFHWCCYVKCNTCSERTEMYTCK              Wnt7A_Rat
321 VWQCNCKFHWCCYVKCNTCSERTEVYTCK              Wnt7A_Chicken
321 VWQCNCKFLWCCYVKCNTCSERTEVYTCK              Wnt7A_Zebrafish
321 VWQCNCKFHWCCYVKCNTCSERTEVYTCK              Wnt7A_Pig
321 VWQCNCKFHWCCYVKCNTCSERTEVYTCK              Wnt7A_Cow
```

*FIG. 2*

WNT COMPOSITIONS AND THERAPEUTIC USES OF SUCH COMPOSITIONS

CROSS REFERENCE TO RELATED APPLICATIONS

This application is a U.S. national phase of PCT/US2012/020984, filed Jan. 11, 2012, which application claims the benefit under 35 U.S.C. §119(e) of U.S. Provisional Application No. 61/431,701, filed Jan. 11, 2012, each of which is incorporated by reference herein, in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FATE_095_00WO_ST25.txt. The text file is 124 KB, was created on Jan. 11, 2011, and is being submitted electronically via EFS-Web.

BACKGROUND

1. Technical Field

The invention relates generally to novel Wnt compositions and therapeutic methods of using the same. The Wnt polypeptides of the invention and compositions thereof may be used therapeutically, for example for promoting muscle regeneration by promoting stem cell expansion and muscle hypertrophy.

2. Description of the Related Art

The Wnt family of genes encodes over twenty cysteine-rich, secreted Wnt glycoproteins that act by binding to Frizzled (Fzd) receptors on target cells. Frizzled receptors are a family of G-protein coupled receptor proteins. Binding of different members of the Wnt-family to certain members of the Fzd family can initiate signaling by one of several distinct pathways. In the "canonical pathway," activation of the signaling molecule, Disheveled, leads to the inactivation of glycogen synthase kinase-3 (GSK-3β), a cytoplasmic serine-threonine kinase. The GSK-3β target, β-catenin, is thereby stabilized and translocates to the nucleus where it activates TCF (T-cell-factor)-dependant transcription of specific promoters (Wodarz, 1998, Dierick, 1999). "Non-canonical" Wnt pathway activation includes a subset of interactions between Wnt and Fzd that may activate $Ca^{2+}$ pathway signaling and potentially PI3K signaling, Rho pathway signaling, and planar cell polarity (PCP) pathway signaling.

Wnts are secreted glycoproteins that function as paracrine or autocrine signals active in several primitive cell types. Although Wnt proteins are secreted from cells, they are found to be hydrophobic and are post-translationally modified by addition of a lipid moiety at a conserved cysteine residue and a conserved serine residue. These lipid modifications are widely accepted to be important for the biological activity and secretion of Wnt proteins. Lipidation and the low solubility of lipidated Wnts, however, are associated with low production yields when detergents are not used during formulation and thus, present a unique challenge for clinical scale production of Wnt. Thus, while Wnts have a tremendous potential for use as therapeutics in a variety of clinical settings, the therapeutic potential of Wnts has yet to be fully realized due to Wnt insolubility and corresponding insufficient production as a purified, biologically active therapeutic.

Accordingly, the art is in need of soluble, novel Wnt polypeptides that retain Wnt biological activity, methods for generating the novel Wnts on a clinical scale, and methods of using the novel Wnts to promote tissue formation, regeneration, maintenance and repair.

BRIEF SUMMARY

The invention provides modified Wnt polypeptides comprising one or more amino acids that reduce lipidation of the Wnt polypeptide. In a particular embodiment, the Wnt polypeptide comprises one or more amino acid deletions, insertions, or substitutions that reduce lipidation of the Wnt polypeptide.

In one embodiment, the polypeptide is a Wnt polypeptide that actives a non-canonical Wnt signaling pathway.

In a particular embodiment, a Wnt polypeptide that actives a non-canonical Wnt signaling pathway is selected from the group consisting of: Wnt4, Wnt5a, Wnt5b, Wnt6, Wnt7a, Wnt7b, and Wnt11.

In some embodiments of the invention, the polypeptide is a Wnt7a or Wnt 5a polypeptide.

In particular embodiments, the invention provides a modified Wnt7a polypeptide having decreased lipidation relative to the lipidation of the Wnt7a polypeptide corresponding to any one of SEQ ID NOs: 2 and 6-11. In other embodiments, the invention provides a modified Wnt7a polypeptide comprising an amino acid deletion, insertion, or substitution at the amino acid position corresponding to position 73 of any one of SEQ ID NOs: 2 and 6-11. In some embodiments, the invention provides a Wnt7a polypeptide comprising an amino acid deletion, insertion, or substitution at the amino acid position corresponding to position 206 of any one of SEQ ID NOs: 2 and 6-11. In particular embodiments, the invention provides a Wnt7a polypeptide comprising amino acid deletions, insertions, or substitutions at the amino acid positions corresponding to positions 73 and 206 of any one of SEQ ID NOs: 2 and 6-11.

In some embodiments, the invention provides a Wnt7a polypeptide comprising an Alanine at the amino acid position corresponding to position 73 or 206 of any one of SEQ ID NOs: 2 and 6-11. In other embodiments, the invention provides a Wnt7a polypeptide comprising Alanine at the amino acid positions corresponding to positions 73 and 206 of any one of SEQ ID NOs: 2 and 6-11. The invention also provides a composition comprising any of the embodiments herein wherein the Wnt7a polypeptide is a human or mouse Wnt7a polypeptide.

In particular embodiments, the invention provides a modified Wnt5a polypeptide having decreased lipidation relative to the lipidation of the Wnt5a polypeptide corresponding to any one of SEQ ID NOs: 15 and 19-23. In other embodiments, the invention provides a modified Wnt5a polypeptide comprising an amino acid deletion, insertion, or substitution at the amino acid position corresponding to position 104 of any one of SEQ ID NOs: 15 and 19-23. In some embodiments, the invention provides a Wnt5a polypeptide comprising an amino acid deletion, insertion, or substitution at the amino acid position corresponding to position 244 of any one of SEQ ID NOs: 15 and 19-23. In particular embodiments, the invention provides a Wnt5a polypeptide comprising amino acid deletions, insertions, or substitutions at the amino acid positions corresponding to positions 104 and 244 of any one of SEQ ID NOs: 15 and 19-23.

In some embodiments, the invention provides a Wnt5a polypeptide comprising an Alanine at the amino acid position corresponding to position 104 or 244 of any one of SEQ ID NOs: 15 and 19-11. In other embodiments, the invention provides a Wnt5a polypeptide comprising Alanine at the amino acid positions corresponding to positions 104 and 244 of any one of SEQ ID NOs: 15 and 19-23. The invention also provides a composition comprising any of the embodiments herein wherein the Wnt5a polypeptide is a human or mouse Wnt5a polypeptide.

In some embodiments, the invention provides a Wnt polypeptide comprising an amino acid sequence as set forth in any one of SEQ ID NOs: 3-5, 12-13, and 16-18.

In various embodiments, the present invention contemplates, in part, a fusion polypeptide comprising a Wnt polypeptide comprising an amino acid sequence as set forth in any one of SEQ ID NOs: 3-5, 12-13, and 16-18.

In one embodiment, the fusion polypeptide comprises a native signal peptide, a heterologous signal peptide, or a hybrid of a native and a heterologous signal peptide.

In a particular embodiment, the heterologous signal peptide is selected from the group consisting of: a CD33 signal peptide, an immunoglobulin signal peptide, a growth hormone signal peptide, an erythropoietin signal peptide, an albumin signal peptide, a secreted alkaline phosphatase signal peptide, and a viral signal peptide.

In a certain embodiment, the heterologous signal peptide is a CD33 signal peptide, an IgGκ signal peptide, or an IgGμ signal peptide.

In additional embodiments, the fusion polypeptide comprises a heterologous protease cleavage site.

In one embodiment, the heterologous protease cleavage site is selected from the group consisting of: a tobacco etch virus (TEV) protease cleavage site, a heparin cleavage site, a thrombin cleavage site, an enterokinase cleavage site and a Factor Xa cleavage site.

In further embodiments, the fusion polypeptide comprises an epitope tag selected from the group consisting of: a HIS6 epitope, a MYC epitope, a FLAG epitope, a V5 epitope, a VSV-G epitope, and an HA epitope.

In particular embodiments, the fusion polypeptide comprises an amino acid sequence as set forth in any one of SEQ ID NOs: 3-5 and 12-13, has increased production, secretion, or solubility compared to a corresponding native Wnt polypeptide as set forth in SEQ ID NOs: 2 and 6-11.

In certain embodiments, the fusion polypeptide comprises an amino acid sequence as set forth in any one of SEQ ID NOs: 16-18, has increased production, secretion, or solubility compared to a corresponding native Wnt polypeptide as set forth in SEQ ID NOs: 15 and 19-23.

The invention also provides polynucleotides encoding Wnt polypeptides having one or more amino acids that reduce lipidation of the Wnt polypeptide. Some embodiments of the invention provide a vector comprising a polynucleotide encoding a Wnt polypeptide having one or more amino acids that reduce lipidation of the Wnt polypeptide. The invention also provides a host cell comprising such vector, and Wnt polypeptides produced by the host cell.

The invention also provides compositions comprising the Wnt polypeptides, polynucleotides, and vectors of the invention. In some embodiments, the composition comprises a pharmaceutically-acceptable salt, carrier, or excipient, and in some embodiments, the composition is soluble in an aqueous solution. In particular embodiments of the invention, the composition is formulated for injection. In certain embodiments, the composition is formulated without a detergent. In related embodiments, detergent is substantially absent from the formulation of the composition. In another related embodiment, the formulated composition is substantially free of detergent. In more specific embodiments the composition is formulated for one or more of intravenous injection, intracardiac injection, subcutaneous injection, intraperitoneal injection, or direct injection into a muscle.

In some embodiments of the invention, the composition promotes tissue formation, regeneration, maintenance or repair. In particular embodiments, the tissue is muscle, and in more specific embodiments the muscle is skeletal, cardiac, or smooth muscle.

In other embodiments, the composition of the invention promotes stem cell expansion. In some embodiments, the stem cell is an adult stem cell, and in particular embodiments, the adult stem cell is a satellite stem cell.

In some embodiments, the composition of the invention promotes muscle hypertrophy or prevents atrophy.

The invention additionally provides a method for treating or preventing muscle loss comprising administering to a subject a composition having a Wnt polypeptide comprising one or more amino acids that reduce lipidation of the Wnt polypeptide. In some embodiments, the composition comprises a pharmaceutically-acceptable salt, carrier, or excipient, and in particular embodiments the composition is soluble in an aqueous solution. In other particular embodiments, the composition is formulated for injection, and in even more particular embodiments, the composition is formulated for one or more of intravenous injection, intracardiac injection, subcutaneous injection, intraperitoneal injection, or direct injection into muscle.

In certain embodiments, the composition is formulated without a detergent. In related embodiments, detergent is substantially absent from the formulation of the composition. In another related embodiment, the formulated composition is substantially free of detergent.

In some embodiments of the method of the invention, the subject has or is at risk of having a disease or condition affecting muscle. In particular embodiments, the disease is a degenerative disease, and in more particular embodiments the degenerative disease is muscular dystrophy. In even more particular embodiments, the muscular dystrophy is selected from Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

In other embodiments of the method, the disease or condition affecting muscle is a wasting disease, muscular attenuation, muscle atrophy, ICU-induced weakness, prolonged disuse, surgery-induced weakness, or a muscle degenerative disease. In more particular embodiments, the condition is muscle atrophy associated with muscle disuse, immobilization, surgery-induced weakness, or injury.

In some embodiments, administering the composition promotes muscle atrophy. In particular embodiments, the muscle is skeletal muscle or cardiac muscle.

In other embodiments of the method of the invention, administering the composition promotes satellite cell expansion.

BRIEF DESCRIPTION OF THE SEVERAL VIEWS OF THE DRAWINGS

FIG. 1 shows a ClustalW alignment of all 19 human Wnt polypeptide sequences. Conserved potential post-translational lipidation sites are shaded in grey and aligned with Cysteine 73 and Serine 206 of Human Wnt 7a. Asparagine residues thought to be sites of glycosylation are underlined.

FIG. 2 shows a ClustalW alignment of the conserved Wnt7a polypeptide sequences from various species.

FIG. 3 shows Myoblast hypertrophy on stimulation with non-canonical Wnts.

FIG. 6 shows High Performance Liquid Chromatography (HPLC) traces detecting the detergent CHAPS in solution.

FIG. 11 immunoglobulin Fc fusion proteins.

BRIEF DESCRIPTION OF THE SEQUENCE IDENTIFIERS

Figure 3A:
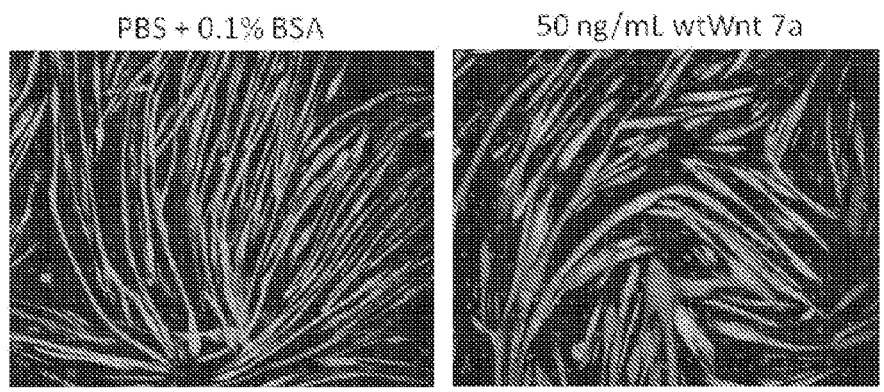
FIG. 3a shows a representative image of in vitro myoblast hypertrophy stimulated by a non-canonical Wnt treatment (Wnt7a).

SEQ ID NO: 1 sets forth a cDNA sequence of human Wnt7a.

SEQ ID NO: 2 sets forth the amino acid sequence of the human Wnt7a polypeptide encoded by SEQ ID NO: 1.

SEQ ID NO: 3 sets forth the amino acid sequence of the human Wnt7a polypeptide of SEQ ID NO: 2, having an alanine mutation at amino acid position 73.

SEQ ID NO: 4 sets forth the amino acid sequence of the human Wnt7a polypeptide of SEQ ID NO: 2, having an alanine mutation at amino acid position 206.

SEQ ID NO: 5 sets forth the amino acid sequence of the human Wnt7a polypeptide of SEQ ID NO: 2, having an alanine mutation at amino acid position 73 and at position 206.

SEQ ID NO: 6 sets forth the amino acid sequence of a mouse Wnt7a polypeptide.

SEQ ID NO: 7 sets forth the amino acid sequence of a rat Wnt7a polypeptide.

SEQ ID NO: 8 sets forth the amino acid sequence of a chicken Wnt7a polypeptide.

SEQ ID NO: 9 sets forth the amino acid sequence of a zebrafish Wnt7a polypeptide.

SEQ ID NO: 10 sets forth the amino acid sequence of a porcine Wnt7a polypeptide.

SEQ ID NO: 11 sets forth the amino acid sequence of a bovine Wnt7a polypeptide.

SEQ ID NO: 12 sets forth the amino acid sequence of a human Wnt7a polypeptide with the native secretion signal peptide replaced with the signal peptide of Human Immunoglobulin Kappa Chain.

SEQ ID NO: 13 sets forth the amino acid sequence of a human Wnt7a polypeptide having an alanine mutation at amino acid position 73 and at position 206, with the native secretion signal peptide replaced with the signal peptide of Human Immunoglobulin Kappa Chain.

SEQ ID NO: 14 sets forth a cDNA sequence of human Wnt5a.

SEQ ID NO: 15 sets forth the amino acid sequence of the human Wnt5a polypeptide encoded by SEQ ID NO: 14.

SEQ ID NO: 16 sets forth the amino acid sequence of the human Wnt5a polypeptide of SEQ ID NO: 15, having an alanine mutation at amino acid position 104.

SEQ ID NO: 17 sets forth the amino acid sequence of the human Wnt5a polypeptide of SEQ ID NO: 15, having an alanine mutation at amino acid position 244.

SEQ ID NO: 18 sets forth the amino acid sequence of the human Wnt5a polypeptide of SEQ ID NO: 15, having an alanine mutation at amino acid position 104 and at position 244.

SEQ ID NO: 19 sets forth the amino acid sequence of a mouse Wnt5a polypeptide.

SEQ ID NO: 20 sets forth the amino acid sequence of a rat Wnt5a polypeptide.

SEQ ID NO: 21 sets forth the amino acid sequence of a chicken Wnt5a polypeptide.

SEQ ID NO: 22 sets forth the amino acid sequence of a zebrafish Wnt5a polypeptide.

SEQ ID NO: 23 sets forth the amino acid sequence of a bovine Wnt5a polypeptide.

SEQ ID NO: 24 sets forth the amino acid sequence of a human Wnt1 polypeptide.

SEQ ID NO: 25 sets forth the amino acid sequence of a human Wnt2 polypeptide.

SEQ ID NO: 26 sets forth the amino acid sequence of a human Wnt2b polypeptide.

SEQ ID NO: 27 sets forth the amino acid sequence of a human Wnt3 polypeptide.

SEQ ID NO: 28 sets forth the amino acid sequence of a human Wnt3a polypeptide.

SEQ ID NO: 29 sets forth the amino acid sequence of a human Wnt4 polypeptide.

SEQ ID NO: 30 sets forth the amino acid sequence of a human Wnt5b polypeptide.

SEQ ID NO: 31 sets forth the amino acid sequence of a human Wnt6 polypeptide.

SEQ ID NO: 32 forth the amino acid sequence of a human Wnt7b polypeptide.

SEQ ID NO: 33 sets forth the amino acid sequence of a human Wnt8a polypeptide.

SEQ ID NO: 34 sets forth the amino acid sequence of a human Wnt8b polypeptide.

SEQ ID NO: 35 sets forth the amino acid sequence of a human Wnt9a polypeptide.

SEQ ID NO: 36 sets forth the amino acid sequence of a human Wnt9b polypeptide.

SEQ ID NO: 37 sets forth the amino acid sequence of a human Wnt10a polypeptide.

SEQ ID NO: 38 sets forth the amino acid sequence of a human Wnt10b polypeptide.

SEQ ID NO: 39 sets forth the amino acid sequence of a human Wnt11 polypeptide.

SEQ ID NO: 40 sets forth the amino acid sequence of a human Wnt16 polypeptide.

SEQ ID NOs: 41-46 set forth oligonucleotide sequences.

DETAILED DESCRIPTION

A. Overview

While post-translational lipidation of Wnts is believed to be required for biological activity and protein secretion, the invention provides novel Wnt polypeptides having the amino acid sites of lipidation altered so that no post-translational lipidation occurs. The proteins of the invention retain Wnt biological activity, and the invention thus provides modified Wnt compositions having improved biologic drug-like properties such as enhanced solubility, production, and formulation, and therapeutic uses for such Wnt compositions. The invention provides a novel solution to the problem posed by the insolubility of Wnt polypeptides and further, provides inventive Wnt polypeptides, including fusion polypeptides, that are suitable for clinical scale production and therapeutic use. Therapeutic uses for the Wnt compositions of the invention include, for example, promoting tissue formation, regeneration, repair or maintenance.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., Molecular Cloning: A Laboratory Manual (3$^{rd}$ Edition, 2001); Sambrook, et al., Molecular Cloning: A Laboratory Manual (2$^{nd}$ Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, Greene Pub. Associates and Wiley-interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); and Harlow and Lane, Antibodies, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

As used herein, the term "substantially" refers to a quantity, level, concentration, value, number, frequency, percentage, dimension, size, amount, weight or length that is 95%, 96%, 97%, 98%, 99% or 100% of a reference value. For example, a composition that is substantially free of a substance, e.g., a detergent, is 95%, 96%, 97%, 98%, 99% or 100% free of the specified substance, or the substance is undetectable as measured by conventional means. Similar meaning can be applied to the term "absence of," where referring to the absence of a particular substance or component of a composition.

As used herein, the term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent.

As used herein, the term "adult stem cell" refers to a stem cell found in a developed organism. Adult stem cells include, but are not limited to, ectodermal stem cells, endodermal stem cells, mesodermal stem cells, neural stem cells, hematopoietic stem cells, muscle stem cells, and the like. A muscle stem cell is an example of stem cell that is traditionally thought to be unipotent, giving rise to muscle cells only.

As used herein, the term "satellite stem cell" refers to a type of adult stem cell that gives rise to cells of the myogenic lineage, e.g., myoblasts and myocytes.

As used herein, the term "progenitor cell" refers to a cell that has the capacity to self-renew and to differentiate into more mature cells, but is committed to a lineage (e.g., hematopoietic progenitors are committed to the blood lineage), whereas stem cells are not necessarily so limited. A myoblast is an example of a progenitor cell, which is capable of differentiation to only one type of cell, but is itself not fully mature or fully differentiated. A myoblast may differentiate into a myocyte.

As used herein, the term "myocyte" or "myofiber" refers to a differentiated type of cell found in muscles. Each myocyte contains myofibrils, which are long chains of sarcomeres, the contractile units of the muscle cell. There are various specialized forms of myocytes: cardiac, skeletal, and smooth muscle cells, with various properties known in the art.

As used herein, the term "self-renewal" refers to a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Asymmetric cell division thus does not increase the number of daughter cells identical to the parental cell, but maintains the number of cells of the parental cell type. Symmetric cell division, in contrast, produces two daughter cells that are each identical to the parental cell. Symmetric cell division thus increases the number of cells identical to the parental cell, expanding the population of parental cells. In particular embodiments, symmetric cell division is used interchangeably with "cell expansion."

As used herein, the term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. States of undifferentiation or differentiation may be assessed, for example, by assessing or monitoring the presence or absence of biomarkers using immunohistochemistry or other procedures known to a person skilled in the art.

As used herein, the term "lineage commitment" refers to the process by which a stem cell becomes committed to forming a particular limited range of differentiated cell types. Lineage commitment arises, for example, when a stem cell gives rise to a progenitor cell during asymmetric cell division. Committed progenitor cells are often capable of self-renewal or cell division.

As used herein, the term "terminal differentiation" refers to the final differentiation of a cell into a mature, fully differentiated cell. Usually, terminal differentiation is associated with withdrawal from the cell cycle and cessation of proliferation.

As used herein, the term "muscle hypertrophy" refers to an increase in muscle size, and may include an increase in individual fiber volume and/or an increase in the cross-sectional area of myofibers, and may also include an increase in the number of nuclei per muscle fiber. Muscle hypertrophy may also include an increase in the volume and mass of whole muscles; however, muscle hypertrophy can be differentiated from muscle hyperplasia, which is an increased number of muscle fibers. In one embodiment, muscular hypertrophy refers to an increase in the number of actin and myosin contractile proteins.

As used herein, the terms "promoting," "enhancing," "stimulating," or "increasing" generally refer to the ability of a Wnt composition of the invention to produce or cause a greater physiological response (i.e., measurable downstream effect), as compared to the response caused by either vehicle or a control molecule/composition. One such measurable physiological response includes, without limitation, an increase in symmetrical stem cell division compared to asymmetrical cell division, e.g., increase in satellite stem cells, and/or an increase muscle hypertrophy compared to normal, untreated, or control-treated muscle cells. For example, the physiological response may be increased by at least 5%, 10%, 20%, 30%, 40%, 50%, 60%, 70%, 80%, 90%, 100%, 125%, 150%, 175%, 200%, or greater. In another non-limiting example, muscle hypertrophy in response to administration of a Wnt composition of the invention may be increased by at least 5%, 10%, 20%, 30%, 40%, 50%, 60%, 70%, 80%, 90%, 100%, 125%, 150%, 175%, 200%, or greater, compared to normal, untreated, or control-treated muscle. An "increased" or "enhanced" response is typically a "statistically significant" response, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the terms "retaining" or "maintaining," or "retain" or "maintain", generally refer to the ability of a Wnt composition of the invention (i.e., a composition of a modified Wnt) to produce or cause a physiological response (i.e., measurable downstream effect) that is of a similar nature to the response caused by a Wnt composition of the naturally occurring Wnt amino acid or nucleic acid sequence. For example, the Wnt compositions of the invention exhibit Wnt biological activity, and thus retain Wnt activity. The compositions of the invention also produce a physiological response, such as muscle hypertrophy, that is of a similar nature to the response caused by a naturally occurring Wnt polypeptide. A Wnt composition of the invention that elicits a similar physiological response may elicit a physiological response that is at least 5%, at least 10%, at least 15%, at least 20%, at least 25%, at least 30%, at least 40%, at least 50%, at least 60%, at least 70%, at least 75%, at least 80%, at least 85%, at least 90%, at least 95% or about 100% of the level of physiological response elicited by a composition comprising a naturally occurring Wnt amino acid or nucleic acid sequence.

A modified or engineered Wnt7a polypeptide of the invention that retains the "naturally occurring Wnt7a activity" refers to a modified Wnt7a polypeptide having one or more amino acid mutations, additions, deletions, and/or substitutions that reduce lipidation of the protein, wherein the polypeptide generates a physiological response that is at least 100%, at least 90%, at least 80%, at least 70%, at least 60%, at least 50%, at least 40%, at least 30%, at least 20%, at least 10%, or at least 5% of the physiological response generated by the corresponding naturally occurring Wnt7a polypeptide.

A modified or engineered Wnt5a polypeptide of the invention that retains the "naturally occurring Wnt5a activity" refers to a modified Wnt5a polypeptide having one or more amino acid mutations, additions, deletions, and/or substitutions that reduce lipidation of the protein, wherein the polypeptide generates a physiological response that is at least 100%, at least 90%, at least 80%, at least 70%, at least 60%, at least 50%, at least 40%, at least 30%, at least 20%, at least 10%, or at least 5% of the physiological response generated by the corresponding naturally occurring Wnt5a polypeptide.

As used herein, the terms "decrease" or "lower," or "lessen," or "reduce," or "abate" refers generally to the ability of a Wnt composition of the invention to produce or cause a lesser physiological response (i.e., downstream effects), as compared to the response caused by either vehicle or a control molecule/composition, e.g., decreased apoptosis. In one embodiment, the decrease can be a decrease in gene expression or a decrease in cell signaling that normally is associated with a reduction of cell viability. A "decrease" or "reduced" response is typically a "statistically significant" response, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

C. Wnt Signaling Pathways

The Wnt signaling pathway is an ancient and evolutionarily conserved pathway that regulates crucial aspects of cell fate determination, cell migration, cell polarity, neural patterning and organogenesis during development and throughout adult life. Wnt signaling pathways downstream of the Fz receptor have been identified, including canonical or Wnt/β-catenin dependent pathways and non-canonical or β-catenin-independent pathways, which can be further divided into Planar Cell Polarity, Wnt/Ca$^{2+}$ pathways, and others.

Wnt proteins bind to the N-terminal extra-cellular cysteine-rich domain of the Frizzled (Fz) receptor family of which there is ten Fz in humans. The Fz protein is a seven-transmembrane-span protein with topological homology to G-protein coupled receptors. In addition, to the interaction between Wnt and Fz, co-receptors are also required for mediating Wnt signaling. For example the low-density-lipoprotein-related protein5/6 (LRP5/6) is required to mediate the canonical Wnt signal whereas receptor tyrosine kinase RYK may be required for non-canonical functions. Another level of regulation of Wnt signaling occurs in the extra-cellular milieu with the presence of a diverse number of secreted Wnt antagonists. After Wnt binds to a receptor complex, the signal is transduced to cytoplasmic phosphoprotein Dishevelled (Dsh/Dvl). Dsh can directly interact with Fz. At the level of Dsh, the Wnt signal branches into at least three major cascades, canonical (β-catenin), Planar Cell Polarity and Wnt/Ca$^{2+}$. Further, G protein coupled receptor signaling may also stimulate growth and survival pathways such as PI3K.

1. The Canonical Wnt Signaling Pathway

The canonical Wnt signaling pathway was first identified and delineated from genetic screens in *Drosophila* and intensive studies in the fly, worm, frog, fish and mouse have led to the identification of a basic molecular signaling framework. The hallmark of the canonical Wnt pathway is the accumulation and translocation of the adherens junction associated-protein β-catenin into the nucleus. In the absence of Wnt signaling, cytoplasmic β-catenin is degraded by a β-catenin destruction complex, which includes Axin, adenomatosis polyposis coli (APC), protein phosphatase 2A (PP2A), glycogen synthase kinase 3β (GSK3β) and casein kinase 1α (CK1α). Phosphorylation of β-catenin within this complex by CK1α and GSK3β targets it for ubiquitination and subsequent proteolytic destruction by the proteosomal machinery. Binding of Wnt to its receptor complex composed of the Fz and the LRP5/6 induces the dual phosphorylation of LRP6 by CK1 and GSK3-β and this allows for the translocation of a protein complex containing Axin from the cytosol to the plasma membrane. Dsh is also recruited to the membrane and binds to Fz and Axin binds to phosphorylated LRP5/6. This complex formed at the membrane at Fz/LRP5/6 induces the stabilization of β-cat via either sequestration and/or degradation of Axin. B-catenin translocates into the nucleus where it complexes with Lef/Tcf family members to mediate transcriptional induction of target genes.

Canonical Wnt signaling affects formation of anterior head structure and neuroectodermal pattering, posterior patterning and tail formation, as well as for formation of various organ systems including the heart, lungs, kidney, skin and bone.

Wnts that can signal through the canonical Wnt signaling pathway include, but are not limited to, Wnt1, Wnt2, Wnt2b/13, Wnt3, Wnt3a, Wnt8, Wnt8a, Wnt8b, Wnt10a, Wnt10b, and Wnt16.

2. The Non-Canonical Wnt Signaling Pathway

The non-canonical pathway is often referred to as the β-catenin-independent pathway. This pathway can be further divided into at least two distinct branches, the Planar Cell Polarity pathway (or PCP pathway) and the Wnt/Ca2+ pathway, of which only the PCP is discussed in further detail herein. The PCP pathway emerged from genetic studies in *Drosophila* in which mutations in Wnt signaling components including Frizzled and Dishevelled were found to randomize the orientation of epithelial structures including cuticle hairs and sensory bristles. Cells in the epithelia are known to possess a defined apical-basolateral polarity but, in addition, they are also polarized along the plane of the epithelial layer. This rigid organization governs the orientation of structures including orientation of hair follicles, sensory bristles and hexagonal array of the ommatidia in the eye. In vertebrates, this organization has been shown to underlie the organization and orientation of muscle cells, stereo-cilia in the sensory epithelium of the inner ear, the organization of hair follicles, and the morphology and migratory behavior of dorsal mesodermal cells undergoing gastrulation.

Wnt signaling is transduced through Fz independent of LRP5/6 leading to the activation of Dsh. Dsh through Daam1 mediates activation of Rho which in turn activates Rho kinase (ROCK). Daam1 also mediates actin polymerization through the actin binding protein Profilin. Dsh also mediates activation of Rac, which in turn activates JNK. The signaling from Rock, JNK and Profilin are integrated for cytoskeletal changes for cell polarization and motility during gastrulation.

Wnts that can signal through the non-canonical Wnt signaling pathway include, but are not limited to, Wnt4, Wnt5a, Wnt5b, Wnt6, Wnt7a, Wnt7b, and Wnt11.

3. Wnt Signaling in Muscle Cell Development

Satellite stem cells are adult stem cells that give rise to muscle cells. Satellite cells in adult skeletal muscle are located in small depressions between the sarcolemma of their host myofibers and the basal lamina. Upon damage, such as physical trauma, repeated exercise, or in disease, satellite cells become activated, proliferate and give rise to a population of myogenic precursor cells (myoblasts) expressing the myogenic regulatory factors (MRF) MyoD and Myf5. In the course of the regeneration process, myoblasts undergo multiple rounds of division before committing to terminal differentiation, fusing with the host fibers or generating new myofibers to reconstruct damaged tissue (Charge and Rudnicki, 2004). During skeletal muscle regeneration, the satellite cell population is maintained by a stem cell subpopulation, thus allowing tissue homeostasis and multiple rounds of regeneration during the lifespan of an individual (Kuang et al., 2008). Satellite stem cells (Pax7+/Myf5−) represent about 10% of the adult satellite cell pool, and give rise to daughter satellite myogenic cells (Pax7+/Myf5+) through asymmetric apical-basal cell divisions.

Wnt signaling plays a key role in regulating developmental programs through embryonic development, and in regulating stem cell function in adult tissues (Clevers, 2006). Wnts are necessary for embryonic myogenic induction in the paraxial mesoderm (Borello et al., 2006; Chen et al., 2005; Tajbakhsh et al., 1998), as well in the control of differentiation during muscle fiber development (Anakwe et al., 2003). Recently, the Wnt planar cell polarity (PCP) pathway has been implicated in regulating the orientation of myocyte growth in the developing myotome (Gros et al., 2009). In the adult, Wnt signaling is thought to be necessary for the myogenic commitment of adult stem cells in muscle tissue following acute damage (Polesskaya et al., 2003; Torrente et al., 2004). Other studies suggest that Wnt/β-catenin signaling regulates myogenic differentiation through activation and recruitment of reserve myoblasts (Rochat et al., 2004). In addition, the Wnt/β-catenin signaling in satellite cells within adult muscle appears to control myogenic lineage progression by limiting Notch signaling and thus promoting differentiation (Brack et al., 2008).

Recently, it was determined that the Wnt receptor Fzd7 was markedly upregulated in quiescent satellite stem cells. In addition, further studies revealed that Wnt7a is expressed during muscle regeneration and acts through its receptor Fzd7 and Vang12, a component of the planar cell polarity (PCP) pathway, to induce symmetric satellite stem cell expansion and dramatically enhance muscle regeneration.

Inhibition of receptor or effector molecules in the PCP pathway, e.g., Fzd7 or Vang12, is believed to abrogate the effects of Wnt7a on satellite stem cells (Le Grand et al., 2009). It has further been demonstrated that administration of lipidated Wnt7a polypeptide, or a polynucleotide encoding a Wnt7a polypeptide that is subsequently post-translationally modified by lipidation, significantly increased satellite stem cell numbers in vitro and in vivo, and promoted tissue formation in vivo, leading to enhanced repair and regeneration in injured and diseased muscle tissue (Le Grand et al., 2009).

Without wishing to be bound to any particular theory, it is contemplated that the mechanism of action of Wnt7a that leads to enhanced repair and regeneration in injured and diseased muscle tissue has two paths: Wnt7a may stimulate the symmetrical expansion of muscle satellite (stem) cells through a PCP pathway, resulting in a larger pool of cells that can subsequently differentiate into myoblasts; and secondly, Wnt7a signaling via the G protein coupled receptor (Frizzled) may stimulate phosphatidylinositol 3-kinase/Akt (protein kinase B)/mammalian target of rapamycin (PI3K/Akt/mTOR) pathway signaling in myoblasts and myofibers, which has been shown to stimulate hypertrophy (Bodine et al., Nature Cell Biology. 2001; vol. 3; pp. 1014-1017; Glass et al., Nature Cell Biology. 2003; vol. 5; pp. 87-90; Ciciliot and Schiaffino, Current Pharmaceutical Design. 2010; 16(8); pp. 906-914). Wnt7a can signal via the G-protein coupled receptor Frizzled 7 and this Wnt/Frz interaction may contribute to both biological effects.

In various embodiments, the invention contemplates, in part, using Wnt compositions comprising one or more modified Wnts that signal through the non-canonical Wnt signaling pathway to repair and regenerate injured muscle tissue. In particular embodiments, the inventive compositions comprise a modified non-canonical Wnt selected from the group consisting of: Wnt4, Wnt5a, Wnt5b, Wnt6, Wnt7a, Wnt7b, and Wnt11. In preferred embodiments, the inventive compositions comprise a modified Wnt5a or Wnt7a polypeptide. In another preferred embodiment, the inventive compositions comprise a modified Wnt5a or Wnt7a polypeptide lacking one or more lipidation sites.

In certain embodiments, the invention compositions comprise a fusion polypeptide comprising a native, heterologous, or hybrid signal peptide, and a non-canonical Wnt polypeptide, optionally lacking one or more lipidation sites.

Although the importance of the PI3K/Akt/mTOR pathway for muscle cell hypertrophy has been described, the therapeutic challenge to specifically stimulate this pathway in muscle cells poses significant obstacles to enhancing repair and regeneration in injured and diseased muscle tissue. Early studies with potent PI3-kinase activators such as IGF-1 produced hypertrophy in vitro but the possibility exists for "off-target" metabolic effects (i.e., IGF-1 and PI3K are key regulators of housekeeping metabolic, survival and metabolic processes). Thus, the potential for a muscle-specific stimulation of a non-canonical Wnt pathway, e.g., Wnt7a-Fzd7 stimulation of PI3K/Akt/mTOR pathway, would represent an important and unique therapeutic breakthrough.

As described in further detail below, the present invention contemplates, in part, inventive Wnt compositions that provide an unexpected solution to this technological hurdle as well as other obstacles to the therapeutic use of Wnt compositions to enhance repair and regeneration in injured and diseased muscle tissue.

D. Polypeptides

Wnt signaling pathways are key components of cell signaling networks. The human Wnt gene family consists of 19 members, encoding evolutionarily conserved glycoproteins with 22 or 24 Cys residues and several conserved Asn and Ser residues. Exemplary human Wnt proteins include Wnt1, Wnt2, Wnt2b/13, Wnt3, Wnt3a, Wnt4, Wnt5a, Wnt5b, Wnt6, Wnt7a, Wnt7b, Wnt8, Wnt8a, Wnt8b, Wnt9a, Wnt9b, Wnt10a, Wnt10b, Wnt11, and Wnt16.

The Wnts are secreted glycoproteins that are heavily modified prior to transport and release into the extra-cellular milieu. After signal sequence cleavage and translocation into the endoplasmic reticulum (ER), Wnts are transported through the endomembrane system to the cell surface and undergo several modifications. Wnts undergo N-linked glycosylation (Burrus and McMahon 1995; Kadowaki et al., 1996; Komekado et al., 2007; Kurayoshi et al., 2007; Mason et al., 1992; Smolich et al., 1993; Tanaka et al. 2002). Many Wnts also are palmitoylated at the first conserved cysteine, e.g., C93 in Wnt1, C77 in Wnt3a, and C104 in Wnt5a (Galli et al., 2007; Kadowaki et al., 1996; Komekado et al., 2007; Willert et al. 2003). In addition, Wnt3a is modified with palmitoleic acid at a conserved serine, 5209, which is also conserved in Wnt1 (S224) Wnt5a (Takada et al., 2006). Furthermore, these conserved cysteine and serine residues are present in many Wnts, e.g., Wnt1, Wnt3a, Wnt4, Wnt5a, Wnt6, Wnt7a, Wnt9a, wnt10a, and Wnt 11, among others (Takada et al., 2006; see also FIG. 1).

Wnt acylation is widely accepted to cause the notoriously hydrophobic nature of secreted Wnts (Willert et al., 2003). In addition, post-translational lipidation of mammalian Wnts is believed to be important for function. Mutating a conserved N-terminal cysteine of Wnt1, Wnt3a, or Wnt5a prevented palmitoylation in cell culture. These mutant Wnts were secreted but were shown to have little or no signaling activity (Galli et al., 2007; Komekado et al., 2007; Kurayoshi et al., 2007; Willert et al., 2003), and unpalmitoylated Wnts are believed to be unable to bind Fz receptors (Komekado et al., 2007; Kurayoshi et al. 2007). Mutating the conserved serine in the central portion of Wnt3a prevented palmitoleic acid addition and blocked secretion and thus, activity (Takada et al., 2006). Research on *Drosophila* Wg confirmed the importance of acylation (Franch-Marro et al., 2008a; Nusse 2003; van den Heuvel et al., 1993).

Further, these data are supported by the porcupine (porc) phenotype in *Drosophila*, which shows a strong loss of Wg signaling (van den Heuvel et al., 1993). Porc is an ER-localized integral membrane O-acyl transferase (Kadowaki et al., 1996) required for Wg palmitoylation (Zhai et al., 2004), and for Wg ER exit (Tanaka et al., 2002). Vertebrate Porc also promotes Wnt lipidation and is required for Wnt signaling and Wnt biological activity (Galli et al., 2007).

These studies establish a model in which palmitoleic acid-modification is required for secretion, and palmitate for Fz binding. Thus, Wnt polypeptides lacking either or both of these lipid modifications would be expected to lack biological activity.

In various embodiments, the invention contemplates, in part, Wnt polypeptides that have been modified or engineered to decrease or remove canonical lipidation sites, but that unexpectedly retain Wnt biological activity. In particular embodiments, the inventive Wnt polypeptides promote cell expansion and muscle hypertrophy, and promote tissue formation, regeneration, maintenance and repair. As used herein, the term "canonical" when used in reference to an amino acid sequence, refers to an amino acid or group of amino acids present in the naturally occurring polypeptide. In some contexts, "canonical" is used interchangeably with "native" when referring to amino acids present in the naturally occurring polypeptide.

In certain embodiments, a Wnt polypeptide has been modified or engineered to lack one or more of the native amino acids for lipidation of the Wnt polypeptide. In certain particular embodiments, a Wnt polypeptide has been modified or engineered to lack all of the native amino acids for lipidation of the Wnt polypeptide. In some embodiments, the Wnt polypeptide is a non-canonical Wnt polypeptide, a Wnt polypeptide that signals through a non-canonical Wnt signaling pathway. In particular embodiments, the non-canonical Wnt is selected from the group consisting of: Wnt4, Wnt5a, Wnt5b, Wnt6, Wnt7a, Wnt7b, and Wnt11. In preferred embodiments, the Wnt polypeptide is a Wnt5a or Wnt7a polypeptide that is modified or engineered as discussed herein to lack canonical or native lipidation sites, but that retains or has increased canonical and/or non-canonical Wnt signaling activity.

As noted above, the invention, in embodiments, provides compositions comprising engineered Wnt polypeptides or polynucleotides encoding such engineered Wnt polypeptides, using techniques known and available in the art. In particular embodiments, the Wnt polypeptides are engineered to remove one or more, or all, lipidation sites.

As used herein, the terms "polypeptide," "peptide," and "protein" are used interchangeably, unless specified to the contrary, and according to conventional meaning, i.e., as a sequence of amino acids linked by peptide bonds or modified peptide bonds. In particular embodiments, the term "polypeptide" includes fusion polypeptides. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides of the invention may be prepared using any of a variety of well known recombinant and/or synthetic techniques, illustrative examples of which are further discussed below. However, in particular embodiments, Wnt polypeptides of the invention have been engineered such that they have one or more amino acid substitutions, deletions, insertions, or mutations that remove or eliminate one, two, or more or all lipidation sites on the Wnt polypeptide. In certain embodiments, the Wnt polypeptide is a non-canonical Wnt polypeptide, i.e., a Wnt polypeptide that signals through a non-canonical Wnt signaling pathway.

In various embodiments, the Wnt polypeptide is selected from the group consisting of: Wnt4, Wnt5a, Wnt5b, Wnt6, Wnt7a, Wnt7b, and Wnt11, wherein the Wnt polypeptide lacks, e.g., by amino acid substitution, deletion, or mutation, one or more or all lipidation sites. In preferred embodiments, the Wnt polypeptide is a Wnt5a or Wnt7a polypeptide that lacks, e.g., by amino acid substitution, deletion, or mutation, one or more or all lipidation sites.

As used herein, the term "non-canonical Wnt polypeptide," refers to a Wnt polypeptide that generally or predominantly signals through non-canonical Wnt signaling pathways. Exemplary non-canonical Wnt polypeptides include, but are not limited to Wnt4, Wnt5a, Wnt5b, Wnt6, Wnt7a, Wnt7b, and Wnt11. In some embodiments, the term "non-canonical Wnt polypeptide," refers to a modified or engineered non-canonical Wnt polypeptide having a sequence that is at least about 70%, more preferably about 80%, 85%, 90%, 91%, 92%, 93%, 94%, 95%, 96%, 97%, 98%, 99% or about 100%, identical to a naturally occurring non-canonical Wnt polypeptide sequence. Identity may be assessed over at least about 10, 25, 50, 100, 200, 300, or more contiguous amino acids, or may be assessed over the full length of the sequence. Methods for determining % identity or % homology are known in the art and any suitable method may be employed for this purpose. Illustrative examples of non-canonical Wnt polypeptides are set forth in SEQ ID Nos: 2-13 and 15-23, 29-32, and 39.

As used herein, the term "Wnt7a polypeptide," refers to a Wnt7a protein having a polypeptide sequence corresponding to a wild type Wnt7a sequence. In some embodiments, the term "Wnt7a polypeptide," refers to a modified or engineered Wnt7a polypeptide having a sequence that is at least about 70%, more preferably about 80%, 85%, 90%, 91%, 92%, 93%, 94%, 95%, 96%, 97%, 98%, 99% or about 100%, identical to a naturally occurring Wnt7a sequence. Identity may be assessed over at least about 10, 25, 50, 100, 200, 300, or more contiguous amino acids, or may be assessed over the full length of the sequence. Illustrative examples of Wnt7a polypeptides are set forth in SEQ ID Nos: 2-13.

As used herein, the term "Wnt5a polypeptide," refers to a Wnt5a protein having a polypeptide sequence corresponding to a wild type Wnt5a sequence. In some embodiments, the term "Wnt5a polypeptide," refers to a modified or engineered Wnt5a polypeptide having a sequence that is at least about 70%, more preferably about 80%, 85%, 90%, 91%, 92%, 93%, 94%, 95%, 96%, 97%, 98%, 99% or about 100%, identical to a naturally occurring Wnt5a sequence. Identity may be assessed over at least about 10, 25, 50, 100, 200, 300, or more contiguous amino acids, or may be assessed over the full length of the sequence. Illustrative examples of Wnt5a polypeptides are set forth in SEQ ID Nos: 15-23.

As used herein, the terms "modified Wnt polypeptide," "modified or engineered Wnt polypeptide," and "engineered Wnt polypeptide," are used interchangeably and refer to a Wnt polypeptide, biologically active fragments or variants thereof, or homolog, paralog, or ortholog thereof that comprises one or more amino acid mutations, additions, deletions, or substitutions. In particular embodiments of the invention, modified Wnt polypeptides comprise one or more amino acid mutations, additions, deletions, and/or substitutions of conserved lipidation sites in order to prevent lipidation of the Wnt polypeptide but that also result in a Wnt polypeptide that retains Wnt biological activity. In particular embodiments, the modified Wnt polypeptide lacks one or more or all lipidation sites but retains Wnt activity. Preferably, modified Wnt polypeptides of the invention retain at least 100%, at least 90%, at least 80%, at least 70%, at least 60%, at least 50%, at least 40%, at least 30%, at least 20%, at least 10%, or at least 5% of the naturally occurring Wnt activity.

As used herein, the terms "modified non-canonical Wnt polypeptide," "modified or engineered non-canonical Wnt polypeptide," and "engineered non-canonical Wnt polypeptide," are used interchangeably and refer to a non-canonical Wnt polypeptide, biologically active fragments or variants thereof, or homolog, paralog, or ortholog thereof that comprises one or more amino acid mutations, additions, deletions, or substitutions. In particular embodiments of the invention, modified non-canonical Wnt polypeptides comprise one or more amino acid mutations, additions, deletions, and/or substitutions of conserved lipidation sites in order to prevent lipidation of the non-canonical Wnt polypeptide but that also result in a non-canonical Wnt polypeptide that retains non-canonical Wnt biological activity, e.g., signaling through the non-canonical Wnt pathway. In particular embodiments, the modified non-canonical Wnt polypeptide lacks one or more or all lipidation sites but retains non-canonical Wnt activity. Preferably, modified non-canonical Wnt polypeptides of the invention retain at least 100%, at least 90%, at least 80%, at least 70%, at least 60%, at least 50%, at least 40%, at least 30%, at least 20%, at least 10%, or at least 5% of the naturally occurring non-canonical Wnt activity.

As used herein, the terms "modified Wnt7a polypeptide," "modified or engineered Wnt7a polypeptide," and "engineered Wnt7a polypeptide," are used interchangeably and refer to a Wnt7a polypeptide, biologically active fragments or variants thereof, or homolog, paralog, or ortholog thereof that comprises one or more amino acid mutations, additions, deletions, or substitutions. In particular embodiments, modified Wnt7a polypeptides of the invention comprise one or more amino acid mutations, additions, deletions, and/or substitutions of conserved lipidation sites in order to prevent lipidation of the Wnt7a polypeptide but that also result in a Wnt7a polypeptide that retains or has increased Wnt7a biological activity. In particular embodiments, the modified Wnt7a polypeptide lacks one or more or all lipidation sites but retains Wnt biological activity. Preferably, Wnt7A polypeptide variants of the invention retain at least 100%, at least 90%, at least 80%, at least 70%, at least 60%, at least 50%, at least 40%, at least 30%, at least 20%, at least 10%, or at least 5% of the naturally occurring Wnt7a activity. Illustrative examples of modified Wnt7a polypeptides are set forth in SEQ ID Nos: 3-5 and 12-13.

As used herein, the terms "modified Wnt5a polypeptide," "modified or engineered Wnt5a polypeptide," and "engineered Wnt5a polypeptide," are used interchangeably and refer to a Wnt5a polypeptide, biologically active fragments or variants thereof, or homolog, paralog, or ortholog thereof that comprises one or more amino acid mutations, additions, deletions, or substitutions. In particular embodiments, modified Wnt5a polypeptides of the invention comprise one or more amino acid mutations, additions, deletions, and/or substitutions of conserved lipidation sites in order to prevent lipidation of the Wnt5a polypeptide but that also result in a Wnt5a polypeptide that retains or has increased Wnt5a biological activity. In particular embodiments, the modified Wnt5a polypeptide lacks one or more or all lipidation sites but retains Wnt biological activity. Preferably, Wnt5A polypeptide variants of the invention retain at least 100%, at least 90%, at least 80%, at least 70%, at least 60%, at least 50%, at least 40%, at least 30%, at least 20%, at least 10%, or at least 5% of the naturally occurring Wnt5a activity. Illustrative examples of modified Wnt5a polypeptides are set forth in SEQ ID Nos: 16-18.

In particular embodiments, the modified Wnt polypeptides of the invention comprise amino acid mutations, additions, deletions, and/or substitutions that decrease or prevent lipidation of the polypeptide, yet such polypeptides have Wnt biological activity. In particular embodiments, the Wnt polypeptide is a canonical Wnt polypeptide comprising an amino acid mutation, addition, deletion, and/or substitution at one or more of the amino acid positions identified in Table 1, wherein the amino acid mutation, addition, deletion, and/or substitution prevents lipidation at at the identified position, and wherein the canonical Wnt polypeptide retains or has increased levels of canonical Wnt biological activity.

TABLE 1

| Wnt | AA positions | Ref. SEQ ID |
| --- | --- | --- |
| Wnt1 | 93; 224 | 24 |
| Wnt2 | 76; 212 | 25 |
| Wnt2b | 88; 224 | 26 |
| Wnt3 | 80; 212 | 27 |
| Wnt3a | 77; 209 | 28 |
| Wnt8a | 54; 186 | 33 |
| Wnt8b | 54; 186 | 34 |
| Wnt9a | 93; 221 | 35 |
| Wnt9b | 89; 216 | 36 |
| Wnt10a | 96; 268 | 37 |
| Wnt10b | 83; 253 | 38 |
| Wnt16 | 81; 227 | 40 |

In particular embodiments, the Wnt polypeptide is a non-canonical Wnt polypeptide comprising an amino acid mutation, addition, deletion, and/or substitution at one or more of the amino acid positions identified in Table 2, wherein the amino acid mutation, addition, deletion, and/or substitution prevents lipidation at at the identified position, and wherein the non-canonical Wnt polypeptide retains or has increased levels of non-canonical Wnt biological activity.

TABLE 2

| Wnt | AA positions | Ref. SEQ ID |
| --- | --- | --- |
| Wnt4 | 78; 212 | 29 |
| Wnt5a | 104; 244 | 15 |
| Wnt5b | 83; 223 | 30 |
| Wnt6 | 76; 228 | 31 |
| Wnt7a | 73; 206 | 2 |
| Wnt7b | 73; 206 | 32 |
| Wnt11 | 80; 215 | 39 |

In particular embodiments, the Wnt polypeptide is a Wnt7a polypeptide comprising an amino acid mutation, addition, deletion, and/or substitution at amino acid 73 and/or 206 that prevents lipidation at such position(s), wherein the Wnt7a polypeptide retains or has increased levels of Wnt7a biological activity. In one embodiment, the polypeptide is a Wnt7a polypeptide comprising an amino acid mutation, addition, deletion, and/or substitution at amino acid position 73 that prevents lipidation at this position, wherein the Wnt7a polypeptide retains or has increased levels of Wnt7a biological activity. In some embodiments, the Wnt polypeptide of the invention is a Wnt7a polypeptide comprising an amino acid mutation, addition, deletion, and/or substitution at amino acid position 206 that prevents lipidation of Wnt7a at this position, wherein the Wnt7a polypeptide retains or has increased levels of Wnt7a biological activity. In some embodiments, the polypeptide is a Wnt7a polypeptide comprising amino acid mutations, additions, deletions, and/or substitutions at amino acid positions 73 and 206, wherein the Wnt7a polypeptide lacks post-translational lipidation and has Wnt biological activity.

In certain embodiments, the C73 and/or S206 of a Wnt7a polypeptide are substituted with Ala or another amino acid that prevents lipidation of these residues. In other embodiments, C73 and/or S206 are mutated or deleted to prevent lipidation of these residues, e.g., SEQ ID Nos: 3-5. In some embodiments, C73 and S206 are substituted with Ala, and the Wnt7a polypeptide of the invention lacks lipidation sites and retains some level of Wnt biological activity e.g., SEQ ID NO: 5.

In particular embodiments, the Wnt polypeptide is a Wnt5a polypeptide comprising an amino acid mutation, addition, deletion, and/or substitution at amino acid 104 and/or 244 that prevents lipidation at such position(s), wherein the Wnt5a polypeptide retains or has or increased levels of Wnt5a biological activity. In one embodiment, the polypeptide is a Wnt5a polypeptide comprising an amino acid mutation, addition, deletion, and/or substitution at amino acid position 104 that prevents lipidation at this position, wherein the Wnt5a polypeptide retains or has increased levels of Wnt5a biological activity. In some embodiments, the Wnt polypeptide of the invention is a Wnt5a polypeptide comprising an amino acid mutation, addition, deletion, and/or substitution at amino acid position 244 that prevents lipidation of Wnt5a at this position, wherein the Wnt5a polypeptide retains or has increased levels of Wnt5a biological activity. In some embodiments, the polypeptide is a Wnt5a polypeptide comprising amino acid mutations, additions, deletions, and/or substitutions at amino acid positions 104 and 244, wherein the Wnt5a polypeptide lacks post-translational lipidation and has Wnt biological activity.

In certain embodiments, the C104 and/or S244 of a Wnt5a polypeptide are substituted with Ala or another amino acid that prevents lipidation of these residues. In other embodiments, C104 and/or S244 are mutated or deleted to prevent lipidation of these residues, e.g., SEQ ID Nos: 16-18. In some embodiments, C104 and S244 are substituted with Ala, and the Wnt5a polypeptide of the invention lacks lipidation sites and retains some level of Wnt biological activity e.g., SEQ ID NO: 18.

As used herein, the term "naturally occurring", refers to a polypeptide or polynucleotide sequence that can be found in nature. For example, a naturally occurring polypeptide or polynucleotide sequence would be one that is present in an organism, and can be isolated from the organism, and which has not been intentionally modified by man in the laboratory. The term "wild-type" is often used interchangeably with the term "naturally occurring."

In the context of the invention, a polypeptide, a biologically active fragment or variant thereof, or homolog, paralog, or ortholog thereof, is considered to have at least substantially the same activity as the wild-type protein when it exhibits about 10%, 20%, 30%, 40% or 50% of the activity of the wild-type protein, preferably at least 50%, at least 55%, at least 60%, at least 65%, at least 70%, at least 75%, or at least 80% of the activity of the wild type protein. In particular embodiments, the polypeptide, a biologically active fragment or variant thereof, or homolog, paralog, or ortholog thereof, exhibits at least 70%, at least 80%, at least 90%, at least 95% or about 100% of the activity of the wild-type protein. In certain embodiments, an activity greater than wild type activity may be achieved. Activity of a non-canonical Wnt polypeptide, e.g., a Wnt 5a or Wnt7a polypeptide, a biologically active fragment or variant thereof, or homolog, paralog, or ortholog thereof, for example, can be determined by measuring its ability to mimic wild-type Wnt biological activity by, for example, stimulating the Wnt signaling pathway, such as by promoting symmetrical stem cell expansion or cell growth, and comparing the ability to the activity of a wild type protein. Methods of measuring and characterizing stem cell division, e.g., satellite stem cell division, and cell growth, e.g., muscle hypertrophy are known in the art.

As used herein, the term "biologically active fragment," as applied to fragments of a reference polynucleotide or polypeptide sequence, refers to a fragment of a modified Wnt polypeptide that has at least about 5, 10, 15, 20, 25, 30, 40, 50, 55, 60, 65, 70, 75, 80, 85, 90, 95, 96, 97, 98, 99, 100, 110, 120, 150, 200, 300, 400, 500, 600, 700, 800, 900, or 1000% or more of the biological activity of a Wnt reference sequence, such as its biological activity to stimulate the Wnt signaling pathway. Certain embodiments of the present invention contemplate, in part, biologically active fragments of a modified Wnt polypeptide of at least about 20, 50, 100, 150, 200, 250, or 300 contiguous amino acid residues in length or polynucleotide sequences encoding the same, including all integers in between, which comprise or encode a polypeptide having the biological activity of a reference Wnt polypeptide, e.g., a naturally occurring Wnt polypeptide.

Modified polypeptides include polypeptide variants. The term "variant" as used herein, refers to polypeptides that are distinguished from a reference polypeptide by the modification, addition, deletion, or substitution of at least one amino acid residue, as discussed elsewhere herein and as understood in the art. In certain embodiments, a polypeptide variant is distinguished from a reference polypeptide by one or more amino acid substitutions (e.g., 1, 2, 3, 4, 5 or more substitutions), which may be conservative or non-conservative. For example, in various embodiments, one or more conservative or non-conservative substitutions can be made in any amino acid residue that is targeted for lipidation in the naturally occurring Wnt polypeptide.

In other particular embodiments, Wnt polypeptide variants comprise one or more amino acid additions, deletions, or substitutions in order to prevent lipidation, to increase Wnt pathway signaling activity, and/or to increase stability of the modified Wnt polypeptide compared to the naturally occurring Wnt polypeptide.

In other particular embodiments, non-canonical Wnt polypeptide variants comprise one or more amino acid additions, deletions, or substitutions in order to prevent lipidation, to increase Wnt pathway signaling activity, and/or to increase stability of the modified Wnt polypeptide compared to the naturally occurring non-canonical polypeptide.

In other particular embodiments, Wnt7a polypeptide variants comprise one or more amino acid additions, deletions, or substitutions in order to prevent lipidation, to increase Wnt pathway signaling activity, and/or to increase stability of the modified Wnt polypeptide compared to the naturally occurring Wnt7a polypeptide.

In other particular embodiments, Wnt5a polypeptide variants comprise one or more amino acid additions, deletions, or substitutions in order to prevent lipidation, to increase Wnt pathway signaling activity, and/or to increase stability of the modified Wnt polypeptide compared to the naturally occurring Wnt5a polypeptide.

To generate such variants, one skilled in the art, for example, can change one or more of the codons of the encoding DNA sequence, e.g., according to Table 3.

TABLE 3

Amino Acid Codons

| Amino Acids | Codons | | | | | |
|---|---|---|---|---|---|---|
| Alanine | GCA | GCC | GCG | GCU | | |
| Cysteine | UGC | UGU | | | | |
| Aspartic acid | GAC | GAU | | | | |
| Glutamic acid | GAA | GAG | | | | |
| Phenylalanine | UUC | UUU | | | | |
| Glycine | GGA | GGC | GGG | GGU | | |
| Histidine | CAC | CAU | | | | |
| Isoleucine | AUA | AUC | AUU | | | |
| Lysine | AAA | AAG | | | | |
| Leucine | UUA | UUG | CUA | CUC | CUG | CUU |
| Methionine | AUG | | | | | |
| Asparagine | AAC | AAU | | | | |
| Proline | CCA | CCC | CCG | CCU | | |
| Glutamine | CAA | CAG | | | | |
| Arginine | AGA | AGG | CGA | CGC | CGG | CGU |
| Serine | AGC | AGU | UCA | UCC | UCG | UCU |
| Threonine | ACA | ACC | ACG | ACU | | |
| Valine | GUA | GUC | GUG | GUU | | |
| Tryptophan | UGG | | | | | |
| Tyrosine | UAC | UAU | | | | |

Guidance in determining which amino acid residues can be substituted, inserted, or deleted without abolishing biological or immunological activity can be found using computer programs well known in the art, such as DNASTAR™ software. If desired, amino acid substitutions can be made to change and/or remove functional groups from a polypeptide. Alternatively, amino acid changes in the protein variants disclosed herein can be conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. See TABLE 4.

TABLE 4

Conservative Amino Acid Substitutions

| Original residue | Conservative substitution |
|---|---|
| Ala (A) | Gly; Ser |
| Arg I | Lys |
| Asn (N) | Gln; His |
| CI (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

Variants of the polypeptides of the invention include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Amino acids in polypeptides of the present invention that are essential for function can be identified by methods known in the art, such as site-directed mutagenesis or alanine-scanning mutagenesis (Cunningham and Wells, *Science* 244: 1081-1085, 1989). Sites that are critical for ligand-receptor binding can also be determined by structural analysis such as crystallization, nuclear magnetic resonance or photoaffinity labeling (Smith et al., *J. Mol. Biol.* 224:899-904, 1992 and de Vos et al. *Science* 255:306-312, 1992).

Certain changes do not significantly affect the folding or activity of the protein. The number of amino acid substitutions a skilled artisan would make depends on many factors, including those described above. Generally speaking, the number of substitutions for any given polypeptide will not be more than 50, 40, 30, 25, 20, 15, 10, 5 or 3.

In addition, pegylation of polypeptides and/or muteins is expected to provide improved properties, such as increased half-life, solubility, and protease resistance. Pegylation is well known in the art.

E. Fusion Polypeptides

In various embodiments, the present invention contemplates, in part, fusion polypeptides, and polynucleotides encoding fusion polypeptides. In one embodiment, the fusion polypeptide comprises a modified Wnt polypeptide, a biologically active Wnt polypeptide fragment, and/or such peptides further comprising one or more amino acid mutations, substitutions, and/or additions, as described elsewhere herein. In a particular embodiment, the fusion polypeptide comprises a non-canonical Wnt polypeptide selected from the group consisting of: Wnt4, Wnt5a, Wnt5b, Wnt6, Wnt7a, Wnt7b, and Wnt11. In preferred embodiments, the Wnt polypeptide is a Wnt5a or Wnt7a polypeptide that is modified or engineered as discussed herein to lack canonical or native lipidation sites, but that retains or has increased Wnt signaling activity.

Fusion polypeptides may comprise a signal peptide at the N-terminal end of the protein, which co-translationally or post-translationally directs transfer of the Wnt polypeptides. Fusion polypeptides may also comprise linkers or spacers, one or more protease cleavage sites, one or more epitope tags or other sequence for ease of synthesis, purification or production of the polypeptide.

Fusion polypeptide and fusion proteins refer to a polypeptide of the invention that has been covalently linked, either directly or via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the desired activity of the polypeptide. For example, in one embodiment, fusion partners may be selected so as to increase the solubility or stability of the protein, to facilitate production and/or purification of a Wnt polypeptide, and/or to facilitate systemic delivery and/or tissue uptake of Wnts. Fusion polypeptides may be produced by chemical synthetic methods or by chemical linkage between the two moieties or may generally be prepared using other standard techniques. In one embodiment, a Wnt fusion polypeptide comprises one or more of, or all of: a signal peptide, a Wnt polypeptide, e.g., a non-canonical Wnt such as Wnt5a or Wnt7a, or a biologically active fragment thereof, a protease cleavage site, and an epitope tag.

As used herein, the term "signal peptide" refers to a leader sequence ensuring entry into the secretory pathway. For industrial production of a secreted protein, the protein to be produced needs to be secreted efficiently from the host cell or the host organism. The signal peptide may be, e.g., the native signal peptide of the protein to be produced, a heterologous signal peptide, or a hybrid of native and heterologous signal peptide. Numerous signal peptides are used for production of secreted proteins.

Thus, in various embodiment, the present invention contemplates a method of improving the production and secretion of Wnt polypeptides, including non-canonical Wnt polypeptides such as Wnt4, Wnt5a, Wnt5b, Wnt6, Wnt7a, Wnt7b, and Wnt11, comprising expressing in cells, e.g., mammalian, insect, or bacterial, a fusion polypeptide having a signal peptide and a non-canonical Wnt polypeptide that has been modified or engineered as discussed herein to lack canonical or native lipidation sites, wherein the polypeptide retains or has increased canonical and/or non-canonical Wnt signaling activity. In preferred embodiments, a method of improving the production and secretion of Wnt5a or Wnt7a comprises expressing in cells a fusion polypeptide having a signal peptide and a Wnt5a or Wnt7a polypeptide that has been modified or engineered as discussed herein to lack canonical or native lipidation sites, but that retains or has increased canonical and/or non-canonical Wnt signaling activity.

Illustrative examples of signal peptides for use in fusion polypeptides of the invention include, but are not limited to: a CD33 signal peptide; an immunoglobulin signal peptide, e.g., an IgGκ signal peptide or an IgGμ signal peptide; a growth hormone signal peptide; an erythropoietin signal peptide; an albumin signal peptide; a secreted alkaline phosphatase signal peptide, and a viral signal peptide, e.g., rotovirus VP7 glycoprotein signal peptide.

In particular embodiments, the inventive fusion polypeptides comprise protease cleavage sites and epitope tags to facilitate purification and production of non-canonical Wnt polypeptides, e.g., Wnt5a and Wnt7a. The position of the protease cleavage site is typically between the C-terminus of the Wnt polypeptide and the epitope tag to facilitate removal of heterologous sequences prior to delivery of the Wnt to a cell or tissue.

Illustrative examples of heterologous protease cleavage sites that can be used in fusion proteins of the invention include, but are not limited to: a tobacco etch virus (TEV) protease cleavage site, a heparin cleavage site, a thrombin cleavage site, an enterokinase cleavage site and a Factor Xa cleavage site.

Illustrative examples of epitope tags that can be used in fusion proteins of the invention include, but are not limited to: a HIS6 epitope, a MYC epitope, a FLAG epitope, a V5 epitope, a VSV-G epitope, and an HA epitope.

A peptide linker sequence may also be employed to separate the fusion polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference. The two coding sequences can be fused directly without any linker or by using a flexible polylinker composed of the pentamer Gly-Gly-Gly-Gly-Ser repeated 1 to 3 times. Such linker has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (Bird et al., 1988, Science 242:423-426).

In one embodiment, fusion polypeptides of the invention comprise a portion of an antibody, such as an immunoglobulin "Fc region", and a modified Wnt polpeptide, such as a Wnt5a or Wnt7a polypeptide, that has been modified or engineered as discussed herein to lack canonical or native lipidation sites, but that retains or has increased canonical and/or non-canonical Wnt signaling activity. The Fc region of the antibody is composed of two heavy chains that contribute two or three constant domains depending on the class of the antibody. The Fc region can be obtained from any of the classes of immunoglobulin, IgG, IgA, IgM, IgD and IgE. In some embodiments, the Fc region is a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain). Wnt fusion polypeptides of the invention comprising an Fc region may have improved production and/or purification efficiencies.

In one embodiment, the Wnt fusion polypeptide of the invention comprises a Wnt7a polypeptide modified to lack native lipidation sites, but that retains non-canonical Wnt signaling activity, and a human IgG Fc region. In a specific embodiment, the Wnt7a polypeptide comprises an amino acid deletion, insertion, or substitution at the amino acid position corresponding to position 73 or 206 of SEQ ID NO: 2, and a human IgG Fc region. In a specific embodiment, the Wnt7a polypeptide comprises amino acid deletions, insertions, or substitutions at the amino acid positions corresponding to positions 73 and 206 of SEQ ID NO: 2, and a human IgG Fc region. In a specific embodiment, the Wnt7a polypeptide comprises alanine at the amino acid position corresponding to position 73 or 206 of SEQ ID NO: 2, and a human IgG Fc region. In one embodiment, the Wnt7a polypeptide comprises alanine at the amino acid positions corresponding to positions 73 and 206 of SEQ ID NO: 2, and a human IgG Fc region.

Fusion polypeptides comprising an Fc region and a modified non-canonical Wnt polypeptide, e.g., Wnt5a or Wnt7a, may further comprise one or more of, or all of a native or heterologous signal peptide, protease cleavage sites and epitope tags.

In preferred embodiments, a method of improving the half-life, pharmacokinetic properties, solubility, and production efficiency of a modified Wnt5a or Wnt7a polypeptide comprises expressing in cells a fusion polypeptide having a an Fc region and/or signal peptide and a Wnt5a or Wnt7a polypeptide that has been modified or engineered as discussed herein to lack canonical or native lipidation sites, but that retains or has increased canonical and/or non-canonical Wnt signaling activity.

For example, a modified Wnt5a or Wnt7a polypeptide fused to an immunoglobulin Fc region has increased systemic half-life, improved pharmacokinetic properties, solubility and production efficiency. In one embodiment, fusing a Wnt polypeptide to an Fc portion of an antibody optimizes the pharmacokinetic and pharmacodynamic properties of the fusion polypeptide. For example, the Fc portion of the polypeptide may protect the polypeptide from degradation, keeping the polypepitde in circulation longer. In general, polypeptides, fusion polypeptides (as well as their encoding polynucleotides), and cells are isolated. An "isolated" polypeptide or polynucleotide is one that is removed from its original environment. For example, an "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated polynucleotide," as used herein, refers to a polynucleotide that has been purified from the sequences which flank it in a naturally-occurring state, e.g., a DNA fragment that has been removed from the sequences that are normally adjacent to the fragment. A polynucleotide is considered to be isolated if, for example, it is cloned into a vector that is not a part of the natural environment. An "isolated cell" refers to a cell that has been obtained from an in vivo tissue or organ and is substantially free of extracellular matrix. Preferably, a polypeptide, polynucleotide, or cell is isolated if it is at least about 60% pure, at least about 70% pure, at least about 80% pure, at least about 90% pure, more preferably at least about 95% pure and most preferably at least about 99% pure.

As used herein, the term "obtained from" means that a sample such as, for example, a polynucleotide or polypeptide is isolated from, or derived from, a particular source, such as a recombinant host cell. In another embodiment, the term "obtained from" refers to a cell isolated from or derived from a source such as an in vivo tissue or organ.

F. Polynucleotides

The present invention also provides isolated polynucleotides that encode Wnt polypeptides of the invention. In various embodiments, the present invention contemplates, in part, Wnt polynucleotides that encode polypeptides that lack canonical lipidation sites, but that retain Wnt biological activity, and in some embodiments have increased Wnt signaling activity. In particular embodiments, the inventive Wnt polynucleotides encode Wnt polypeptides that promote stem cell expansion and promote tissue formation, regeneration, maintenance and repair.

The inventive Wnt polynucleotides are suitable for clinical scale production of Wnt polypeptides and for use in methods of enhancing repair and regeneration in injured and diseased muscle tissue in humans. In certain embodiments, a Wnt polynucleotide encodes a Wnt polypeptide that lacks one or more of the native amino acids for lipidation of the Wnt polypeptide. In certain particular embodiments, a Wnt polynucleotide encodes a Wnt polypeptide that lacks all of the native amino acids for lipidation of the Wnt polypeptide. In preferred embodiments, the Wnt polynucleotide encodes a non-canonical Wnt polypeptide that lacks canonical lipidation sites, but retains or has increased Wnt biological activity. In other preferred embodiments, the Wnt polynucleotide encodes a Wnt5a or Wnt7a polypeptide that lacks canonical lipidation sites, but retains or has increased Wnt biological activity, such as non-canonical Wnt signaling activity.

Nucleic acids can be synthesized using protocols known in the art as described in Caruthers et al., 1992, Methods in Enzymology 211, 3-19; Thompson et al., International PCT Publication No. WO 99/54459; Wincott et al., 1995, Nucleic Acids Res. 23, 2677-2684; Wincott et al., 1997, Methods Mol. Bio., 74, 59-68; Brennan et al., 1998, Biotechnol Bioeng., 61, 33-45; and Brennan, U.S. Pat. No. 6,001,311).

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other (see for example, Usman and McSwiggen, supra; Eckstein et al., International PCT Publication No. WO 92/07065; Usman et al., International PCT Publication No. WO 93/15187; Uhlman & Peyman, supra). There are several examples of modified nucleic acid bases known in the art as summarized by Limbach et al., (1994, Nucleic Acids Res. 22, 2183-2196).

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides, and the like. Such segments may be naturally isolated, recombinant, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide of the invention or a portion thereof) or may comprise a variant, or a biological functional equivalent of such a sequence. Polynucleotide variants may contain one or more substitutions, additions, deletions and/or insertions, as described elsewhere herein, preferably such that the variant encodes a polypeptide that lacks canonical lipidation sites, but retains, and in some embodiments, has increased biological activity, such as pathway signaling activity.

Also included are polynucleotides that hybridize to polynucleotides that encode a polypeptide of the invention. To hybridize under "stringent conditions" describes hybridization protocols in which nucleotide sequences at least 60% identical to each other remain hybridized. High stringency hybridization conditions are conditions that enable a probe, primer or oligonucleotide to hybridize only to its target sequence. Stringent conditions are sequence-dependent and will differ. Moderately stringent conditions are conditions that use washing solutions and hybridization conditions that are less stringent (Sambrook, 1989) than those for high stringency, such that a polynucleotide will hybridize to the entire, fragments, derivatives or analogs of nucleic acids of the present invention. Moderate stringency conditions are described in (Ausubel et al., 1987; Kriegler, 1990). Low stringent conditions are conditions that use washing solutions and hybridization conditions that are less stringent than those for moderate stringency (Sambrook, 1989), such that a polynucleotide will hybridize to the entire, fragments, derivatives or analogs of nucleic acids of the present invention. Conditions of low stringency, such as those for cross-species hybridizations are described in (Ausubel et al., 1987; Kriegler, 1990; Shilo and Weinberg, 1981).

In additional embodiments, the invention provides isolated polynucleotides comprising various lengths of contiguous stretches of sequence identical to or complementary to a polynucleotide encoding a polypeptide as described herein. For example, polynucleotides provided by this invention encode at least about 50, 100, 150, 200, 250, 300, or about 350 or more contiguous amino acid residues of a polypeptide of the invention, as well as all intermediate lengths. It will be readily understood that "intermediate lengths", in this context, means any length between the quoted values, such as 56, 57, 58, 59, etc., 101, 102, 103, etc.; 151, 152, 153, etc.; 201, 202, 203, etc.

It will be appreciated by those of ordinary skill in the art that, as a result of the degeneracy of the genetic code, there are many nucleotide sequences that encode a polypeptide as described herein, including polynucleotides that are optimized for human and/or primate codon selection. Further, alleles of the genes comprising the polynucleotide sequences provided herein may also be used.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

As used herein, the terms "control elements" or "regulatory sequences" refer to those sequences present in an expression vector that are non-translated regions of the vector, e.g., enhancers, promoters, 5' and 3' untranslated regions, and interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUE-SCRIPT phagemid (Stratagene, La Jolla, Calif.) or PSPORT1 plasmid (Gibco BRL, Gaithersburg, Md.), pET plasmid (Novagen) and the like may be used. The vector components generally include, but are not limited to, one or more of the following: a signal sequence, an origin of replication, one or more marker genes, an enhancer element, a promoter that is recognized by the host organism, and a transcription termination sequence. Specific initiation signals may also be used to achieve more efficient translation of sequences encoding a polypeptide of interest.

In the yeast *Saccharomyces cerevisiae*, a number of vectors containing constitutive or inducible promoters such as alpha factor, alcohol oxidase, and PGH may be used. Also included are *Pichia pandoris* expression systems (see, e.g., Li et al., *Nature Biotechnology*. 24, 210-215, 2006; and Hamilton et al., *Science*, 301:1244, 2003).

In cases where plant expression vectors are used, viral promoters such as the 35S and 19S promoters of CaMV may be used alone or in combination with the omega leader sequence from TMV (Takamatsu, *EMBO J.* 6:307-311 (1987)). These constructs can be introduced into plant cells by direct DNA transformation or pathogen-mediated transfection.

An insect system may also be used to express a polypeptide of interest. Exemplary baculovirus expression systems, include, but are not limited to those that utilize SF9, SF21, and Tni cells (see, e.g., Murphy and Piwnica-Worms, *Curr Protoc Protein Sci*. Chapter 5: Unit 5.4, 2001).

In mammalian host cells, a number of viral-based expression systems are generally available. In addition, transcription enhancers, such as the Rous sarcoma virus (RSV) enhancer, may be used to increase expression in mammalian host cells. Examples of useful mammalian host cell lines include COS-7 cells, 293 or 293T cells, BHK cells, VERO-76 cells, HELA cells, and CHO cells, including DHFR-CHO cells. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

In particular embodiments, polypeptides of the invention are expressed and purified from bacteria. Exemplary bacterial expression vectors include, BLUESCRIPT (Stratagene); pIN vectors (Van Heeke & Schuster, *J. Biol. Chem.* 264:5503 5509 (1989)); and pGEX Vectors (Promega, Madison, Wis.) which may be used to express foreign polypeptides as fusion proteins with glutathione S-transferase (GST). Certain embodiments may employ *E. coli*-based expression systems.

In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression system, including high-throughput expression systems. Media of this type (e.g., Overnight Express™ Autoinduction System) gradually elicit protein expression through metabolic shift without the addition of artificial inducing agents such as IPTG. Certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

The protein produced by a recombinant cell can be purified and characterized according to a variety of techniques. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

In certain embodiments, clinical grade proteins can be isolated from *E. coli* inclusion bodies. In particular embodiments, the present invention contemplates methods for producing a recombinant Wnt polypeptide that is suitable for therapeutic uses, as described elsewhere herein.

In one embodiment, a method for producing a recombinant Wnt polypeptide includes one or more of the following steps: i) expression of a Wnt polynucleotide in a host; ii) culturing the host cell to express the Wnt polypeptide as inclusion bodies; iii) one or more steps of washing the inclusion bodies; iv) solubliizing the polypeptide; v) refolding the polypeptide; vi) purifying the polypeptide; and vii) dializing the polypeptide in a desired buffer.

In certain embodiments, Wnt polynucleotide sequences are codon optimized for expression in a bacterial host.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

G. Compositions

In various embodiments, the invention contemplates, in part, novel compositions of Wnt polypeptides and polynucleotides encoding the same. As discussed elsewhere herein, one of the major limitations or obstacles to the therapeutic use of Wnts is their low solubility, which makes them impracticable to generate on a clinical scale. The inventors have engineered novel Wnt polypeptides that have increased solubility, stability, and that retain or have increased Wnt biological activity compared to naturally occurring Wnts. In particular embodiments, the invention provides aqueous formulations of soluble Wnt polypeptides to promote stem cell expansion and muscle hypertrophy, and promote tissue formation, regeneration, maintenance and repair. In certain embodiments, the invention provides aqueous formulations of soluble Wnt polypeptides to promote stem cell expansion and muscle hypertrophy, and promote tissue formation, regeneration, maintenance and repair, wherein detergents are substantially absent from the formulations.

The compositions of the invention may comprise one or more polypeptides, polynucleotides, vectors comprising same, etc., as described herein, and one or more pharmaceutically-acceptable salts or carriers and/or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins, polypeptides, small molecules or various pharmaceutically-active agents. There is virtually no limit to other components that may also be included in the compositions, provided that the additional agents do not adversely affect the therapeutic potential of the Wnt composition, such as the ability of the composition to promote muscle hypertrophy and promote tissue formation, regeneration, maintenance and repair.

Pharmaceutically-acceptable salts include the acid addition salts (formed with the free amino groups of the protein) and those formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In certain circumstances it will be desirable to deliver the compositions disclosed herein parenterally, intravascularly, e.g., intravenously or intraarterially, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety). Particular embodiments of the invention may comprise other formulations, such as those that are well known in the pharmaceutical art, and are described, for example, in Remington: The Science and Practice of Pharmacy, 20th Edition. Baltimore, Md.: Lippincott Williams & Wilkins, 2000.

H. Methods of Delivery

In one embodiment, cells, e.g., stem cells such as satellite stem cells, are contacted with a composition comprising one or more inventive Wnt polypeptides and/or polynucleotides. It is contemplated that the cells of the invention may be contacted in vitro, ex vivo, or in vivo. In other embodiments, the Wnt compositions of the invention are administered to a subject.

The compositions of the invention can be administered (as proteins/polypeptides, or in the context of expression vectors for gene therapy) directly to the subject or delivered ex vivo, to cells derived from the subject (e.g., as in ex vivo gene therapy). Direct in vivo delivery of the compositions will generally be accomplished by parenteral injection, e.g., subcutaneously, intraperitoneally, intravenously myocardial, intratumoral, peritumoral, or to the interstitial space of a tissue. Other modes of administration include oral and pulmonary administration, suppositories, and transdermal applications, needles, and gene guns or hyposprays.

The compositions of the invention may also be administered by direct injection into a tissue, such as a muscle. In some embodiments of the invention, a composition of the invention is administered by directly injecting the composition into muscle tissue to prevent a loss of muscle in the injected muscle or to promote regeneration or repair of the injected muscle, for example by promoting expansion of the muscle cells or hypertrophy of the injected muscle.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, direct microinjection of the DNA into nuclei, and viral-mediated, such as adenovirus (and adeno-associated virus) or alphavirus, all well known in the art.

In certain embodiments, it will be preferred to deliver one or more modified Wnts using a viral vector or other in vivo polynucleotide delivery technique. In a preferred embodiment, the viral vector is a non-integrating vector or a transposon-based vector. This may be achieved using any of a variety of well-known approaches, such as vectors including adenovirus, retrovirus, lentivirus, adeno-associated virus vectors (AAV), or the use of other viral vectors as expression constructs (including without limitation vaccinia virus, polioviruses and herpes viruses).

Non-viral methods may also be employed for administering the polynucleotides of the invention. In one embodiment, a polynucleotide may be administered directly to a cell via microinjection or a tissue via injection, such as by using techniques described in Dubensky et al., (1984) or Benvenisty & Reshef (1986). It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). In another embodiment, polynucleotides are administered to cells via electroporation.

I. Methods of Treatment

The modified Wnt polypeptides and compositions of the invention are useful for various therapeutic applications. For example, the compositions and methods described herein are useful for promoting tissue formation, regeneration, repair or maintenance in a subject in need thereof.

Some relevant therapeutic applications for the Wnt compositions of the invention include situations where there is a need to prevent muscle loss or regenerate lost or damaged muscle tissue by increasing muscle size, volume or strength. Such situations may include, for example, after chemotherapy or radiation therapy, after muscle injury, or in the treatment or management of diseases and conditions affecting muscle. In certain embodiments, the disease or condition affecting muscle may include a wasting disease (e.g., cachexia, which may be associated with an illness such as cancer or AIDS), muscular attenuation or atrophy, or a muscle degenerative disease. Muscular attenuation and atrophy may be associated with, for example, sarcopenia (including age-related sarcopenia), ICU-induced weakness, disuse of muscle (for example disuse of muscle due to coma paralysis, injury, or immobilization), surgery-induced weakness (e.g., following hip or knee replacement), or a muscle degenerative disease (e.g., muscular dystrophies). This list is not exhaustive.

In certain embodiments, the polypeptides and compositions of the invention may be used to stimulate symmetrical expansion of muscle satellite cells, thereby increasing the proportion of resident satellite cells, or committed precursor cells, in a muscle tissue. The polypeptides and compositions may also be used to promote muscle hypertrophy, such as by increasing the size of individual muscle fibers. The polypeptides and compositions of the invention may thus increase both the number of muscle cells and the size of muscle cells, and as a result may be useful for example, to replace damaged or defective tissue, or to prevent muscle atrophy or loss of muscle mass, in particular, in relation to diseases and disorders affecting muscle, such as muscular dystrophy, neuromuscular and neurodegenerative diseases, muscle wasting diseases and conditions, atrophy, cardiovascular disease, stroke, heart failure, myocardial infarction, cancer, HIV infection, AIDS, and the like.

In additional embodiments, the compositions and methods are useful for repairing or regenerating dysfunctional skeletal muscle, for instance, in subjects having muscle degenerative diseases. The subject can be suspected of having, or be at risk of at having skeletal muscle damage, degeneration or atrophy. The skeletal muscle damage may be disease related or non-disease related. The human subject may have or be at risk of having muscle degeneration or muscle wasting. The muscle degeneration or muscle wasting may be caused in whole or in part by a disease, for example aids, cancer, a muscular degenerative disease, or a combination thereof.

Illustrative examples of muscular dystrophies include, but are not limited to Duchenne muscular dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy. See, e.g., Hoffman et al., *N. Engl. J. Med.*, 318.1363-1368 (1988); Bonnemann, C. G. et al., *Curr. Opin. Ped.*, 8: 569-582 (1996); Worton, R., *Science*, 270: 755-756 (1995); Funakoshi, M. et al., *Neuromuscul. Discord.*, 9 (2): 108-114 (1999); Lim, L. E. and Campbell, K. P., *Cure. Opin. Neurol.*, 11 (5): 443-452 (1998); Voit, T., *Brain Dev.*, 20 (2): 65-74 (1998); Brown, R. H., *Annu. Rev. Med.*, 48: 457-466 (1997); Fisher, J. and Upadhyaya, M., *Neuromuscul. Disord.*, 7 (1): 55-62 (1997).

In certain embodiments, a use of a composition as described herein for the manufacture of a medicament for promoting muscle formation, maintenance, repair, or regeneration of muscle in a subject in need thereof is provided. In particular embodiments, a composition as described herein is provided for use in the manufacture of a medicament for promoting muscle formation, maintenance, repair, or regeneration of muscle in a subject in need thereof is provided. The Wnt polypeptides may be used for preventing or treating muscle atrophy, such as by increasing the size or number of myofibers.

The composition may be administered in an effective amount, such as a therapeutically effective amount. For in vivo treatment of human and non-human subjects, the subject is usually administered a composition comprising an effective amount of one or more modified Wnt polypeptides of the present invention. An "effective amount" refers to an amount effective, at dosages and for periods of time necessary, to achieve the desired therapeutic or prophylactic result.

A "therapeutically effective amount" of a Wnt polypeptide of the invention, or a composition comprising the same, may vary according to factors such as the disease state, age, sex, and weight of the individual, and the ability of a Wnt polypeptide to elicit a desired response in the individual. A therapeutically effective amount is also one in which any toxic or detrimental effects of a Wnt polypeptide are outweighed by the therapeutically beneficial effects. The term "therapeutically effective amount" refers to an amount of a Wnt polypeptide or composition comprising the same that is effective to "treat" a disease or disorder in a mammal (e.g., a patient).

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

In various embodiments, the invention provides for methods of increasing the division symmetry of adult stem cells, such as satellite stem cells compared to untreated stem cell populations. The methods disclosed herein are further capable of promoting symmetrical stem cell division without altering the rate of stem cell division and can promote the survival of a population of stem cells. The methods may be performed in vitro, ex vivo, or in vivo.

In particular embodiments, compositions comprising one or more modified Wnt polypeptides and/or polynucleotides are administered in vivo to a subject in need thereof. As used herein, the term "subject" includes, but is not limited to, a mammal, including, e.g., a human, non-human primate (e.g., baboon, orangutan, monkey), mouse, pig, cow, goat, dog, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate. In preferred embodiments, the subject is human. Subjects in need of treatment for a disease or condition include subjects exhibiting symptoms of such disease or condition, such as those having a disease or condition, as well as those at risk of having a disease or condition.

In particular embodiments, a method for expanding a population of satellite stem cells in vivo, ex vivo, or in vitro comprising contacting the stem cells with an effective amount of a composition comprising a modified non-canonical Wnt polypeptide or a polynucleotide encoding such a modified non-canonical Wnt polypeptide. In particular embodiments, the non-canonical Wnt is selected from the group consisting of: Wnt4, Wnt5a, Wnt5b, Wnt6, Wnt7a, Wnt7b, and Wnt11. In preferred embodiments, the Wnt polypeptide is a Wnt5a or Wnt7a polypeptide or an active fragment or variant thereof, or ortholog, paralog, or homolog thereof, that binds to and activates a Wnt receptor.

Without being bound to any particular theory, it is believed that increasing the number of satellite cells in a tissue, provides enhanced regeneration potential of the tissue.

In particular embodiments, stem cells are isolated or maintained, and expanded ex vivo or in vitro and subsequently administered to a subject in need thereof. For example, stem cells can be cultured and expanded ex vivo or in vitro and contacted with an effective amount of a Wnt composition of the invention and then administered to a patient as a therapeutic stem cell composition according to methods known to skilled persons. In certain embodiments, the expanded stem cell population is administered to the patient in combination with a therapeutic Wnt composition.

The methods of promoting stem cell expansion can be used to stimulate the ex vivo or in vitro expansion of stem cells and thereby provide a population of cells suitable for transplantation or administration to a subject in need thereof.

In some forms of urinary continence, the dysfunctional muscle can be treated with a composition or method of the invention, for example, by direct protein injection into the muscle. Thus, in one embodiment, the method is useful for treating urinary incontinence.

In further embodiments, damaged or dysfunctional muscle tissue may be cardiac muscle. For instance, the damaged muscle tissue may be cardiac muscle damaged by a cardiovascular event such as myocardial infarct, or heart failure, where the target stem cell would be a cardiac stem cell. In accordance with another aspect of the present invention, there is provided a method of promoting cardiac stem cell expansion or cardiac muscle hypertrophy in a mammal comprising administering to the mammal an effective amount of a composition as described herein.

Further, in addition to using the stem cells in transplants, stem cells, or compositions comprising stem cells may be used as a research tool and/or as part of a diagnostic assay or kit. Without wishing to be limiting a kit may comprise muscle stem cells, one or more modified Wnt polypeptides, cell culture or growth medium, cell cryopreservation medium, one or more pharmaceutically acceptable delivery media, one or more modified Wnt polynucleotide sequences or genetic constructs, one or more devices for implantation or delivery of cells to a subject in need thereof, instructions for using, delivering, implanting, culturing, cryopreserving or any combination thereof the cells as described herein.

Indicators of cell expansion and/or muscle hypertrophy may be monitored qualitatively or quantitatively and include, for example, changes in gross morphology, total cell number, histology, histochemistry or immunohistochemistry, or the presence, absence or relative levels of specific cellular markers. The presence, absence or relative levels of cellular markers can be analyzed by, for example, histochemical techniques, immunological techniques, electrophoresis, Western blot analysis, FACS analysis, flow cytometry and the like. Alternatively the presence of mRNA expressed from the gene encoding the cellular marker protein can be detected, for example, using PCR techniques, Northern blot analysis, the use of suitable oligonucleotide probes and the like.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Wnt Polypeptides have Conserved Sites for Post-Translational Modification

Wnt proteins are secreted signaling proteins involved in cell survival, proliferation, division and migration. Wnts are required for effective tissue patterning during embryogenesis and tissue regeneration in the adult. Certain Wnt proteins drive skeletal muscle regeneration through stimulation of satellite stem cell symmetric expansion and muscle fiber hypertrophy.

Figure 11A:
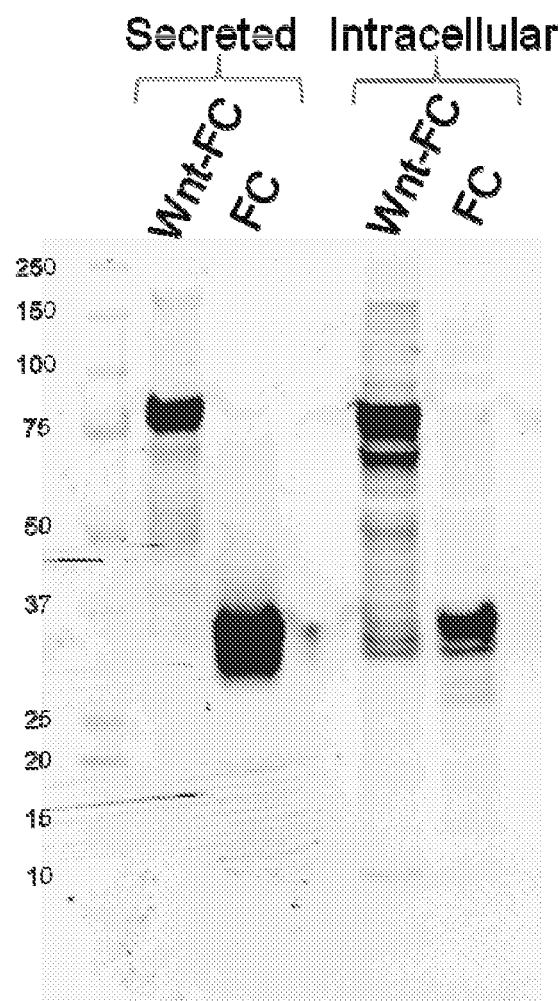
FIG. 11a shows a western blot of a Wnt7a protein with its native secretion signal peptide replaced with the signal peptide from immunoglobulin Kappa and constructed as a immunoglobulin Fc domain fusion protein. The secretion from mammalian culture systems is shown in FIG. 11a in comparison to Fc domain-alone control.
Figure 11B:
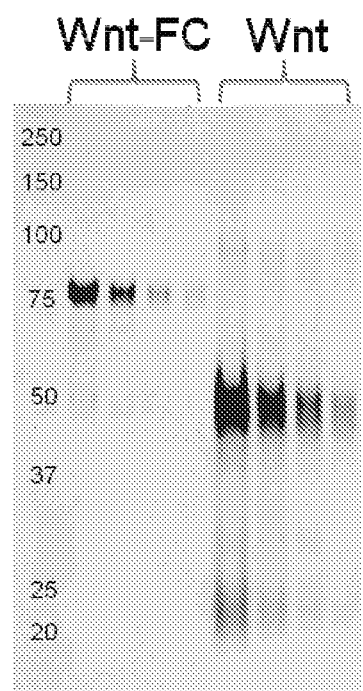
FIG. 11b shows the relative molecular weight differences between Wnt7a and Wnt7a-Fc fusion protein by SDS-PAGE western blot using an anti-Wnt7a detection antibody.

19 human Wnts have been identified and grouped based of discrete regions of homology. The Wnt proteins have complex post-translational modifications including both glycosylation and lipidation. Protein glycosylation is required for effective protein folding and secretion. FIG. 1 is an alignment of all 19 human Wnt polypeptides. The amino acid residues modified by either glycosylation or lipidation are well conserved (see shaded residues). Further, these same residues are conserved across species as can be seen from the alignment of Wnt7a polypeptides in FIGS. 2 and 11. Lipidation has historically been thought to be required for effective activity by fixing the mature secreted protein to the plasma membrane; effectively localizing the Wnt to its frizzled receptors. For this reason, Wnts are thought to be autocrine or local paracrine signaling molecules rather than fully systemic growth factor/cytokines.

As described elsewhere herein, protein lipidation is not a requirement for the activity of all Wnt polypeptides. The selective mutation of lipidated cysteine or serine residues in a wild type Wnt (wtWnt) sequence, e.g., Wnt7a, SEQ ID NO: 2, were replaced with non-lipidated alanine residues. In the specific example of Wnt7a, the cysteine residue at position 73 and/or the serine residue at position 206 were mutated to alanine residues. This resulted in proteins comprising the sequences listed in SEQ ID Nos: 3-5, which lacked post translational lipidation at the mutated residues.

Example 2

Non-Canonical Wnts Induce Myoblast Hypertrophy

Wnt polypeptides signal via frizzled receptors and co-receptors to stimulate several intracellular pathways. Wnts are generally categorized as either "canonical" or "non-canonical" signaling molecules where canonical signaling results in the nuclear localization of the protein β-Catenin and subsequent expression of target genes. Non-canonical signaling generally includes cellular functions of Wnts that do not directly involve the nuclear localization of β-Catenin, such as the activation of the planar cell polarity (PCP) or Calcium/PLC/PKC pathways. Receptors and coreceptors for canonical and non-canonical pathway activation are different; with the canonical signaling pathway showing dependence for the co-receptor LRP. Wnt7a is a non-canonical signaling molecule and has been shown to drive symmetrical expansion of muscle satellite stem cells via the activation of the PCP pathway (Le Grand et al., *Wnt7a activates the planar cell polarity pathway to drive the symmetric expansion of satellite stem cells*. Cell Stem Cell 4, 535-547, 2009). More recently Wnt7a was shown to drive the hypertrophy of myoblasts in culture, potentially via a G-protein-depended activation of the PI3-Kinase/mTOR pathway (Julia von Maltzahn, C. Florian Bentzinger and Michael A. Rudnicki, *Nature Cell Biology*, Dec. 11, 2011; *epub*).

Figure 3B:
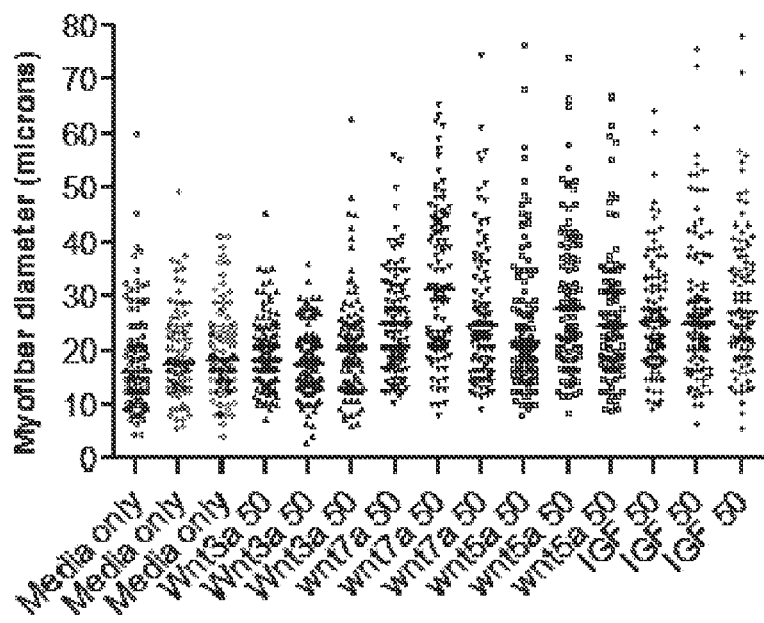
FIG. 3b shows data of in vitro myoblast fiber hypertrophy induced by certain Wnt treatments. 100 fibers were counted for each of 3 biological replicates for each treatment group and individual counts in microns and replicate medians are displayed.

The ability of several Wnt polypeptides to induce hypertrophy of myoblast cells was tested. The Wnt polypeptides tested initially were obtained from R&D systems and represented canonical (Wnt3a) and non-canonical (Wnt5a and Wnt7a) signaling polypeptides. As shown in FIG. 3, while buffer control or canonical Wnt polypeptide Wnt3a had no myoblast hypertrophy effect, both non-canonical Wnt polypeptides (Wnt7a and Wnt5a) produced significant myoblast hypertrophy effect in vitro.

Methods

C2C12 mouse myoblasts were obtained from ATCC (#CRL-1772) and grown on gelatin-coated tissue culture plates in DMEM (MediaTech #10-017-CV) medium supplemented with 10% 50 FBS. The cells remained less than 20% confluent throughout the experiment. 96 well tissue culture plates were coated with 0.1% gelatin for at least 15 minutes at room temperature (RT) and 2,000 cells (in 0.2 mL of growth medium) were plated in each well of the 96-well plate. The plates were then incubated for 24 hours at 37° C. The following day, the media was aspirated and replaced with 0.2 mL of a differentiation media having DMEM (MediaTech #10-017-CV) supplemented with 2% horse serum (Fisher, Hyclone SH30074). After 3 days of differentiation, Wnt polypeptides (rhWnt7a #3008-WN/CF, rhWnt3a #5036-WN/CF or rhWnt5a #645-WN/CF (from R&D systems) were added to the cell culture and incubated for an additional 2 days.

The cells were fixed, washed, permeablized, and stained with myosin slow and fast myosin antibodies (Sigma #M4276-0.2ML, Sigma #M8421-0.2ML). Cells were visualized; myofiber diameter was calculated for 100 fibers per experiment; and the data from 3 independent biological replicates was collated for a total of 300 data points per treatment group. The median fiber diameter for each biological replicate group is shown in FIG. 3. The mean of the median across the three biological replicates for each group was 17.5 µm for medium alone, 18.8 µm (Wnt3a), 27 µm (Wnt7a), 24.6 µm (Wnt5a), and 25.8 µm (insulin growth factor (IGF)). The increase in hypertrophy for cells treated with Wnt7a, Wnt5a and IGF was statistically significant compared with either media control or Wnt3a treatment.

Example 3

Construction and Expression of Modified Wnt7a Polypeptides

Non-canonical Wnts induce muscle satellite stem cell expansion and muscle hypertrophy. Induction of both processes would be of great benefit therapeutically: for the treatment of cachexia, muscle atrophy, and muscular dystrophy. The use of Wnt as a therapeutic requires effective scaled production, and purification and formulation applicable for therapeutic use while retaining the specific Wnt activity and receptor specificity. The post-translational lipidation of Wnt polypeptides represents a potential complication to these requirements of manufacture. Wnts were generally thought to require lipid for effective activity, lipidated proteins are challenging to purify at high concentrations and require the use of detergent formulation for solubility and stability.

Figure 4:
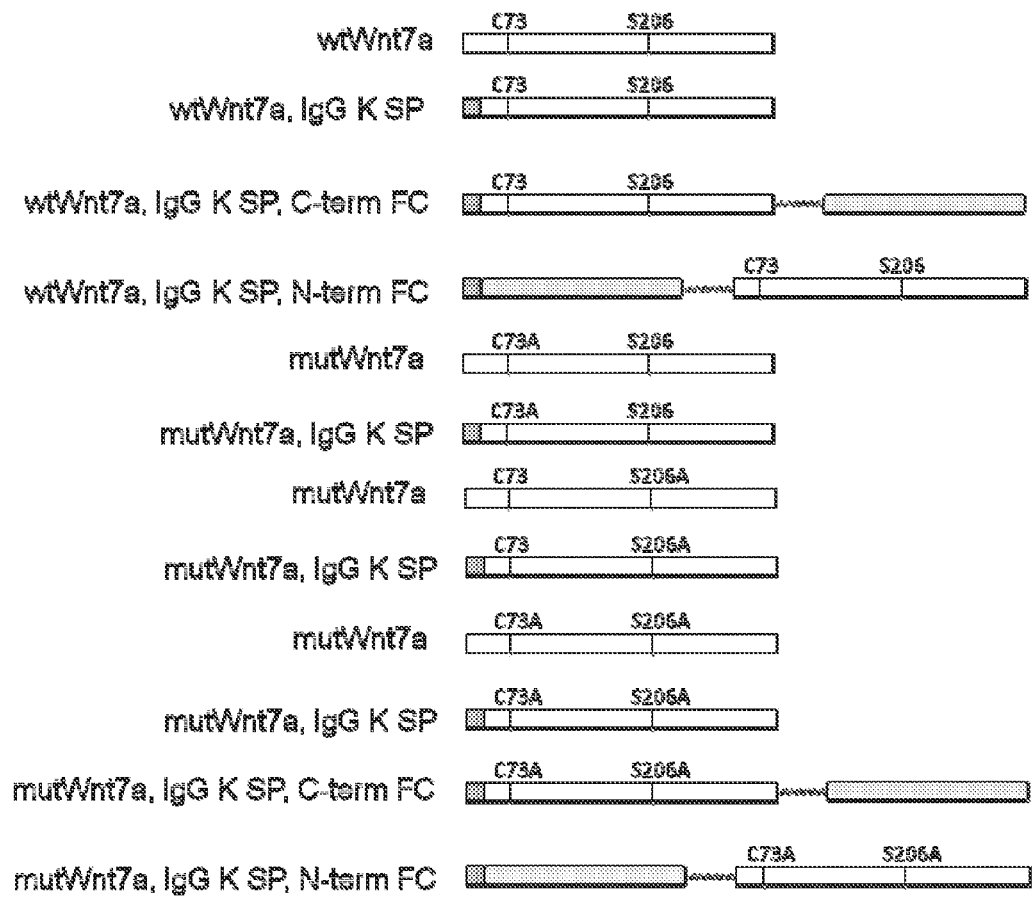
FIG. 4 shows a schematic representation of the various constructed Wnt7a variants. Wild type human Wnt7a sequence is shown in white, variants with specific point mutations leading to amino acid changes are seen in white with amino acid changes as indicated. Replacement of the naturally occurring Wnt7a secretion signal peptide with that of human IgG Kappa chain is indicated as grey shading. Amino or carboxy-terminal fusions of immunoglobulin Fc regions were constructed with linker regions as indicated.

To address these challenges, several variants of Wnt7a were constructed. Specifically, the amino acid residues targeted for post-translational lipidation (Cys 73 and Ser206 in Wnt7a) were mutated to Alanine residues using the following molecular biology techniques. The wild type human Wnt7a was PCR amplified using forward primer 5'-GCATGGATCCACCATGAACCGGAAAGCGCGG-3' (SEQ ID NO: 41) and reverse primer 5'-GCATGCGGCCGCTCACTTGCACGTGTACATCTCC-3' (SEQ ID NO: 42). The PCR product was inserted into pcDNA3.1(+) vector between the BamHI and Not I sites. The modified Wnt7a constructs were prepared using the QuikChange® site-directed mutagenesis method. The human Wnt7a C73A construct (cysteine at amino acid 73 substituted with alanine) was made using the human wild type Wnt7a as a template with forward primer 5'-ATGGGCCTGGACGAGGCCCAGTTTCAGTTCCGC-3' (SEQ ID NO: 43) and reverse primer 5'-GCGGAACTGAAACTGGGCCTCGTCCAGGCCCAT-3' (SEQ ID NO: 44). The human Wnt7a S206A construct (serine at amino acid 206 substituted with alanine) was made using the human wild type Wnt7a as a template using forward primer 5'-GTGCCACGGCGTGGCAGGCTCGTGCACC-3' (SEQ ID NO: 45) and reverse primer 5'-GGTGCACGAGCCTGCCACGCCGTGGCAC-3' (SEQ ID NO: 46). The human Wnt7a C73A/S206A constructs were made using the reagents for the individual C73A and S206A constructs. Final vector DNA was prepared using Qiagen Endo-free purification kits. The Wnt cDNAs in the pcDNA3 vector were expressed in HEK293 cells for 48-72 hrs. Wnt polypeptides were subsequently purified from the HEK293 culture media by affinity chromatography using an antibody specific for all variants of Wnt7a produced (Antibody: Santa Cruz K15 #26361). Activity of the purified modified Wnt polypeptides was tested using in vitro hypertrophy assay as seen in subsequent examples. A schematic of all Wnt7a constructs built is shown in FIG. 4 (see also SEQ ID NOs: 1, 2, 3, 4, 5, 12 and 13).

Example 4

Heterologous Signal Peptides Improve Wnt Secretion and Production

To improve production, secretion, and solubility of Wnt proteins showing poor secretion from the mammalian culture in HEK293 cells—with the majority of expressed protein remaining within the cell—Wnt fusion poylpeptides were constructed in which the endogenous Wnt secretion signal peptide was replaced by the signal peptide of human immunoglobulin G Kappa chain (IgGK) or that of human protein CD33. A schematic of Wnt7a fusion polypeptides comprising heterologous signal peptides is shown in FIG. 4 (see also SEQ ID NOs: 12 and 13).

Figure 5:
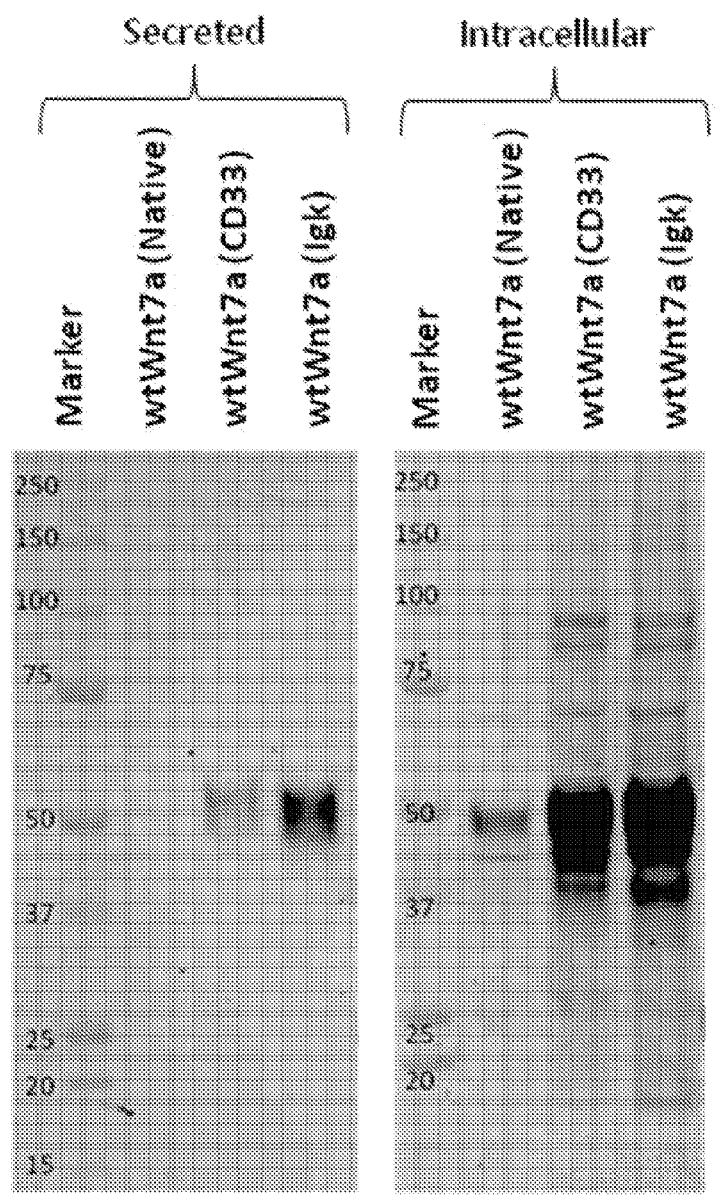
FIG. 5 shows a SDS-PAGE, Western blot of Wnt7a expressed and secreted from HEK293 cells in mammalian tissue culture. The increased expression and subsequent secretion of Wnt polypeptides with exogenous secretion signal peptides from CD33 or IgG Kappa chain can be clearly seen over that of the native signal peptide.

As shown in FIG. 5, the Wnt fusion polypeptides having heterologous signal peptides performed significantly better than Wnt polypeptides comprising a native signal peptide, when compared for expression and secretion in HEK293 culture.

Example 5

Modified Wnt Polypeptides can be Formulated in the Absence of Detergent and Retain Stability and Activity Wnt protein production and formulation has traditionally relied on formulation in detergent to retain solubility of these lipidated proteins. The effective therapeutic delivery of a Wnt polypeptide requires formulation in the absence of detergent. Wnt polypeptides without lipidation sites were constructed as described in Example 3, expressed in mammalian culture systems, purified from the culture media, and formulated in 1% CHAPS detergent. A HPLC-based assay was configured to allow the effective measurement of CHAPS detergent in the Wnt polypeptide formulations.

Figure 6A:
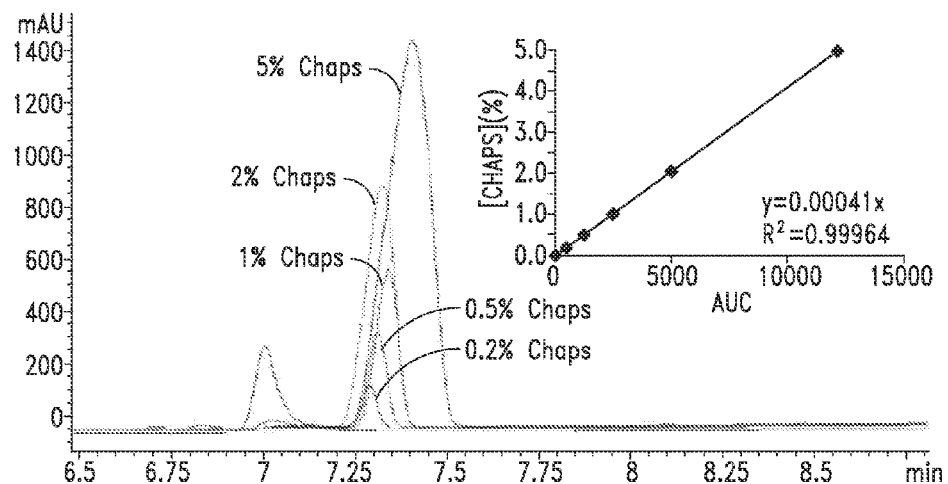
FIG. 6a shows the standard curve for chaps in Phosphate Buffered Saline to calibrate the system.
Figure 6B:
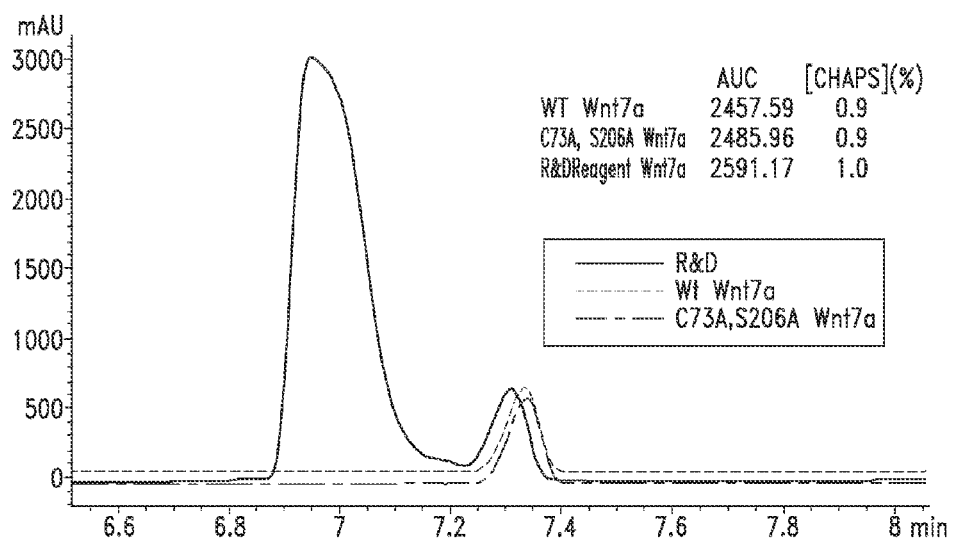
FIG. 6b shows preparations of modified Wnt polypeptidesformulated in 1% CHAPS compared with the commercially available protein from R&D systems (the commercial protein contains a carrier protein that results in a second, larger peak).
Figure 6C:
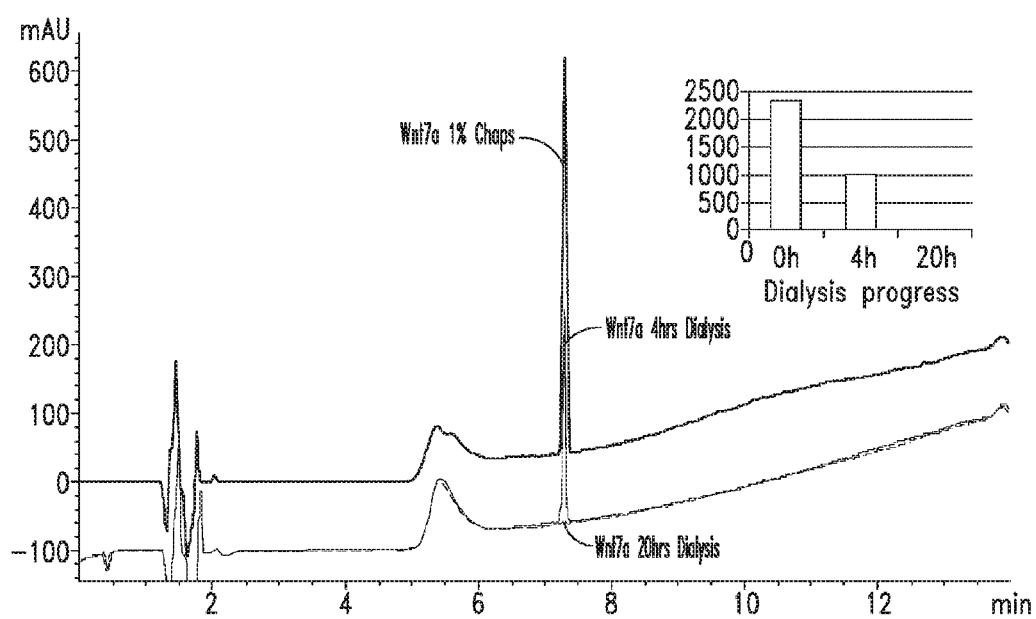
FIG. 6c shows the effective removal of CHAPS from the formulation of the Wnt polypeptides using dialysis over 4 and 20 hours as indicated.

As shown in FIG. 6a, a titration of CHAPS detergent in solution allowed for effective calibration of the assay. Various preparations of pure Wnt polypeptide were tested and final formulation was shown to be ~1% CHAPS solution in PBS (FIG. 6b). Subsequent dialysis of the Wnt polypeptide solution against PBS alone effectively removed the detergent below the level of detection (FIG. 6c). The dialyzed polypeptides were then tested for both stability and activity either in the presence or absence of the CHAPS detergent.

Incubation of the protein formulations at either 4° C. or 37° C. over a 7 day period showed Wnt with native lipidation sites was relatively stable when formulated in detergent but unstable when formulated in the absence of detergent. Conversely, modified Wnts with lipidation sites removed and replaced with Alanine (C73A, S206A) were seen to have improved stability in the absence of detergent when compared to native, lipidated protein.

Wnt variants formulated with or without detergent were then tested for activity in the C2C12 hypertrophy assay as described in Example 2. Wnt polypeptides were produced in HEK293 mammalian culture systems and affinity purified. The Wnt polypeptides were formulated in PBS with 1% CHAPS detergent. Aliquots of each Wnt polypeptides variant were reformulated by detergent removal using dialysis. Wnt proteins had equal molar concentration and were applied to the C2C12 hypertrophy assay.

Figure 7:
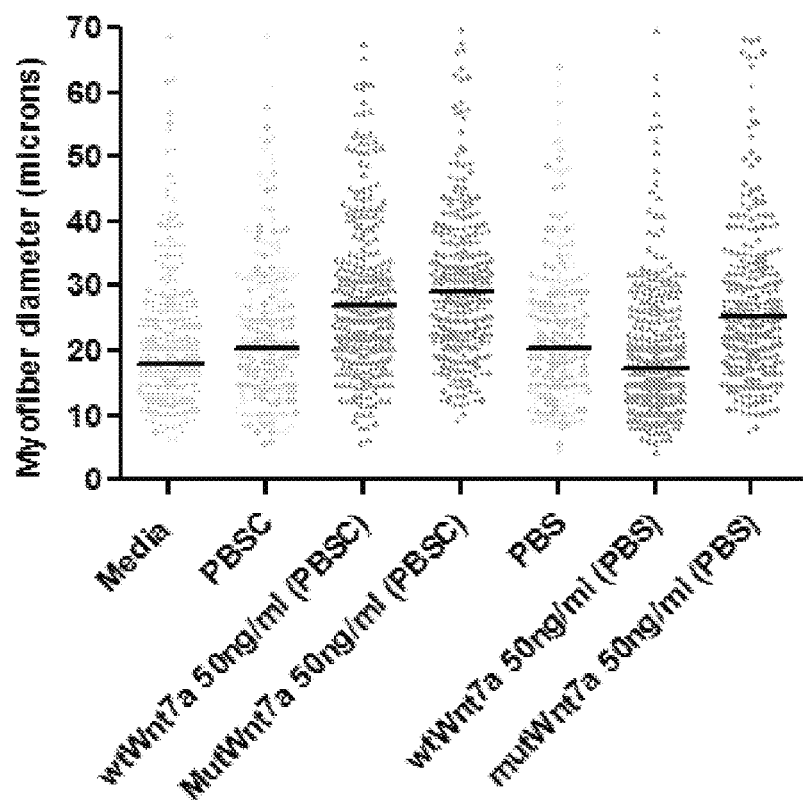
FIG. 7 shows a myoblast hypertrophy assay displaying the activity of Wnt7a variants formulated in the presence or absence of detergent. Wnt proteins were constructed with the IgG Kappa secretion signal peptide. Proteins were produced in HEK293 mammalian culture systems and affinity purified. The proteins were formulated in PBS with 1% Chaps detergent. Aliquots of Each protein variant were reformulated by detergent removal using dialysis. Proteins were seen to have equal molar concentration and were applied to the C2C12 Hypertrophy assay.
Figure 8:
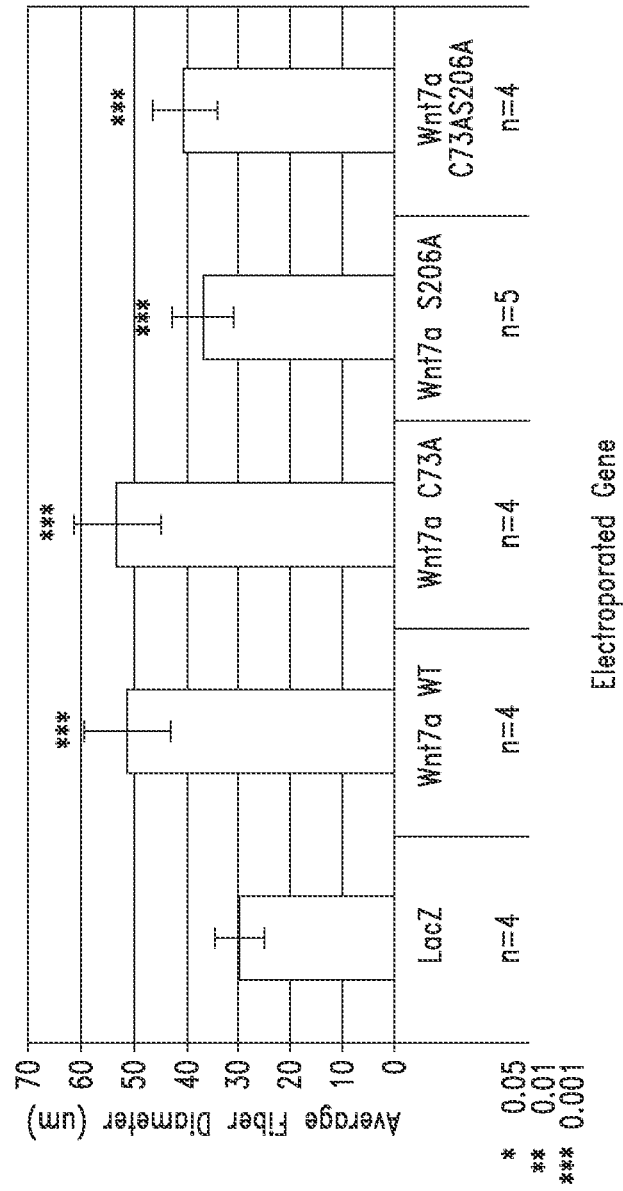
FIG. 8 shows the results of an experiment to determine the average fiber diameter of mouse tibialis anterior (TA) muscles electroporated with expression plasmids encoding modified human Wnt7a polypeptides as discussed elsewhere herein, wild type human Wnt7a, or a LacZ control.
Figure 9:
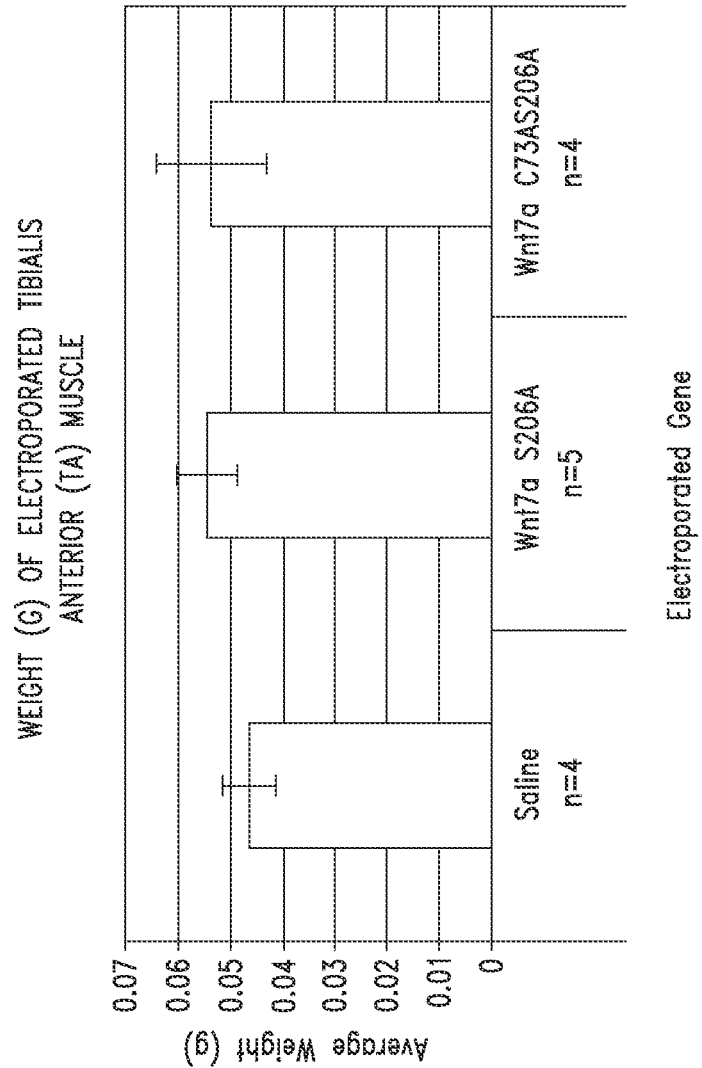
FIG. 9 shows the results of an experiment to determine the weight of mouse tibialis anterior (TA) muscles electroporated with expression plasmids encoding modified human Wnt7a polypeptides as discussed elsewhere herein, or a saline control.
Figure 10:
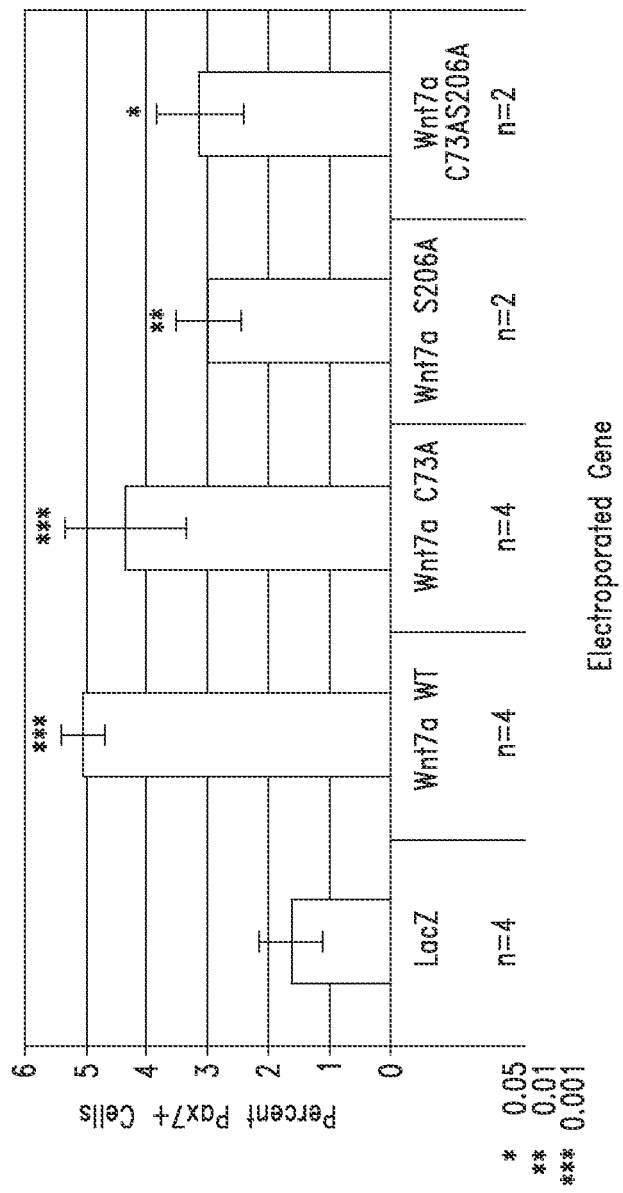
FIG. 10 shows the results of an experiment to determine the number of Pax7+ satellite stem cells in mouse tibialis anterior (TA) muscles electroporated with expression plasmids encoding modified human Wnt7a polypeptides as discussed elsewhere herein, wild type human Wnt7a, or a LacZ control.

Wnt polypeptides produced in the HEK293 culture system with the use of heterologous signal peptides retained their activity when compared to a positive control, native Wnt sequence (FIG. 7). Further, Wnt7a C73A and S206A mutants retained specific hypertrophic activity (FIG. 7). All modified Wnt retained activity when formulated in detergent.

When Wnts were reformulated in the absence of detergent, only the modified Wnts comprising Alanine substituted lipidation sites retained activity, whereas native Wnts lost myoblast hypertrophic activity (FIG. 7). Thus, Wnts specifically altered at conserved lipidation sites, retained biological activity. The modified Wnts also retained activity when formulated in the absence of detergent. Accordingly, the modified Wnt polypeptides of the invention represent useful therapeutic versions of the native protein.

Example 6

Modified Wnt7a Increases Muscle Hypertrophy and Satellite Stem Cell Expansion

To demonstrate the ability of delipidated Wnts, e.g., Wnts that have one or more lipidation sites removed, to stimulate muscle regeneration in vivo, the modified Wnt7a were over-expressed by electroporation of CMV-Wnt7a expression plasmids into TA muscles of 3-month old mice.

1. In Vivo Electroporation

Plasmids constructs encoding a LacZ, wild type Wnt7a, Wnt7a C73A, Wnt7a S206A, and Wnt7a C73A/S206A were electroporated in vivo into mice. 40 μg of each plasmid DNA in 0.9% NaCl or 0.9% NaCl (saline) was injected directly into a left TA muscle that had been exposed by an incision through the skin of an anesthetized mouse. Immediately after injection, electric stimulation was applied directly to the TA by a pulse generator (ECM 830, BTX) of 100-150 volts for 6 pulses, with a fixed duration of 20 ms and an interval of 200 ms using 5 mm needle electrodes (BTX). Experimental and contralateral TA muscles were isolated and embedded in OCT-15% Sucrose (Tissue-Tek) and frozen with isopentane cooled by cold nitrogen.

2. Histology and Quantification

Transverse sections (8 μm) of experimental and contralateral muscles were cut with a cryostat (Leica CM1850). The entire TA muscles were sectioned, in order to compare experimental and contralateral muscles at the same level on serial sections (around 400 sections were obtained from each TA muscle). For LacZ reaction, cryosections were fixed with 0.1% gluteraldehyde and exposed to X-gal solution. For H&E and immunostaining, sections were fixed with 4% paraformaldehyde. For enumeration of fibers, pictures of laminin-stained cryosections were assembled and counted on Adobe Photoshop CS2. Quantification of myofibers caliber was performed with ImageJ. The satellite cell enumeration was performed on Photoshop, on pictures of Pax7 and Laminin co-immunostained cryosections taken in regenerated areas where all the fibers had centrally located nuclei. "Percent Pax-7+ Cells" represents the number of sub-laminar Pax7+ve satellite cells normalized per fiber number, and to the contralateral leg.

3. Statistical Analysis

A minimum of 2 and up to 5 replicates was done for experiments presented. Data are presented as standard error of the mean. Results were assessed for statistical significance using Student's T Test (Microsoft Excel) and differences were considered statistically significant at the $p<0.05$ level.

4. Results

Electroporation of WT Wnt7a, Wnt7a C73A, Wnt7a S206A, and Wnt7a C73A/S206A constructs produced a statistically significant increase in the average fiber diameter of mouse TA muscles compared to a LacZ control plasmid. Moreover, the Wnt7a C73A, Wnt7a S206A, and Wnt7a C73A/S206A constructs retained Wnt biological activity of the wild type Wnt construct, as the increased the average fiber diameter of the TA muscles produced by the Wnt7a C73A, Wnt7a S206A, and Wnt7a C73A/S206A constructs was comparable to that produced by the wild type Wnt construct. These results are shown in FIG. 1.

Notably, FIG. 2 shows that TA muscles electroporated with Wnt7a S206A and Wnt7a C73A/S206A constructs also exhibited a comparable increase in TA muscle mass to TA muscles electroporated with the wild type Wnt construct.

To assess whether Wnt7a C73A, Wnt7a S206A, and Wnt7a C73A/S206A similarly stimulated the expansion of satellite stem cells in vivo, the numbers of satellite cells and satellite stem cells in regenerated muscle were assessed following electroporation of the modified Wnt7a expression plasmids. Over-expression of Wnt7a C73A, Wnt7a S206A, and Wnt7a C73A/S206A resulted in statistically significant increases in the number of Pax7+ satellite cells per myofiber on sections at 3 weeks after electroporation (Wnt7a C73A, p=0.001, n=4; Wnt7a S206A, p=0.01, n=2; Wnt7a C73A/S206A, p=0.05, n=2). The increase in the number of Pax7 satellite cells induced by over-expression of Wnt7a C73A, Wnt7a S206A, and Wnt7a C73A/S206A was comparable to the increase induced by wild type Wnt7a. These results are shown in FIG. 3.

Taken together, these results shown in FIGS. 1-3 indicate that over-expression of Wnt7a C73A, Wnt7a S206A, and Wnt7a C73A/S206A markedly enhances muscle regeneration, as evidenced by the presence of increased numbers of larger fibers and the increased mass of muscle and further, increases the numbers of satellite stem cells in vivo. In addition, these results show that the effect produced by Wnt7a C73A, Wnt7a S206A, and Wnt7a C73A/S206A was comparable to the effect produced by wild type Wnt7a.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Example 7

Wnt Proteins can be Expressed as Immunoglobulin Fc Fusions

Immunoglobulin fusion proteins and/or peptibodies have been used to improve the pharmaceutical properties of the Wnt polypeptides, such as their circulating half life in vivo. Wnt proteins of the present invention were constructed in mammalian expression vectors (pcDNA3+) with either amino-terminal or carboxyterminal Fc-fusion domains as schematically represented in FIG. 4. Amino acid residues 31-349 of native human Wnt7a or the same with C73A and/or S206A mutations were subcloned in frame with the IgG Kappa secretion signal peptide and Human IgG1e3-Fc1 domain as either a N- or C-terminal fusion. This Fc domain comprised amino acid changes that are different from native IgG1 sequence (E233P/L234V/L235A/deltaG236+A327G/A330S/P331S) to reduce antibody dependent cell-mediated cytotoxicity (ADCC) and complement dependent cytotoxicity (CDC) effects. A 17 amino acid linker (GT(GGGGS)3) was added between the Wnt protein sequence and the Fc-fusion sequence to reduce steric hindrance and prevent reduction of Wnt specific activity. These vectors were transfected into HEK293 cells and protein expression continued for 48 hours. Protein expression and secretion was monitored by western blot and can be seen in FIGS. 11*a* and 11*b*. Intact fusion proteins of the expected molecular weight were seen when immune-detected with either anti-Wnt7a antibodies or anti-Fc detection. Effective secretion was observed for the fusion proteins. Secreted proteins were subsequently purified by Protein A or Protein G affinity chromatography.

---

The invention claimed is:

1. A modified Wnt7a polypeptide comprising one or more amino acids that reduce lipidation of the Wnt7a polypeptide, wherein said modified Wnt7a polypeptide comprises an amino acid deletion, insertion, or substitution of Cys73 or Ser206.

2. The modified Wnt7a polypeptide of claim 1, wherein the modified Wnt7a polypeptide activates a non-canonical Wnt signaling pathway.

3. A modified Wnt7a polypeptide having decreased lipidation relative to the lipidation of the Wnt7a polypeptide corresponding to any one of SEQ ID NOs: 2 and 6-11, wherein said modified Wnt7a polypeptide comprise an amino acid deletion, insertion, or substitution of Cys73 or Ser206 of any one of SEQ ID NOs: 2 and 6-11.

4. The modified Wnt7a polypeptide of claim 3, wherein the polypeptide comprises:
   a) an amino acid deletion, insertion, or substitution at the amino acid position corresponding to position 73 of any one of SEQ ID NOs: 2 and 6-11;
   b) an amino acid deletion, insertion, or substitution at the amino acid position corresponding to position 206 of any one of SEQ ID NOs: 2 and 6-11;
   c) one or more amino acid deletions, insertions, or substitutions at the amino acid positions corresponding to positions 73 and 206 of any one of SEQ ID NOs: 2 and 6-11;
   d) an Alanine at the amino acid position corresponding to position 73 or 206 of any one of SEQ ID NOs: 2 and 6-11; or
   e) an Alanine at the amino acid positions corresponding to positions 73 and 206 of any of SEQ ID NOs: 2 and 6-11.

5. A polynucleotide encoding the modified Wnt7a polypeptide of claim 1.

6. A vector comprising the polynucleotide of claim 5.

7. A host cell comprising the vector of claim 6.

8. A modified Wnt7a polypeptide produced by the host cell of claim 7.

9. A composition comprising the polypeptide of claim 8.

10. A method for treating or preventing muscle loss comprising administering to a subject a composition according to claim 9.

11. The method of claim 10, wherein the subject has or is at risk of having a disease or condition affecting muscle.

12. The method of claim 11, wherein the degenerative disease is muscular dystrophy.

13. The method of claim 11, wherein the disease or condition affecting muscle is a wasting disease, muscular attenuation, muscle atrophy, ICU-induced weakness, prolonged disuse, surgery-induced weakness, or a muscle degenerative disease.

14. A Wnt7a polypeptide comprising an amino acid sequence as set forth in any one of SEQ ID NOs: 3-5, and 12-13.

15. A fusion polypeptide comprising a Wnt7a polypeptide according to claim 14 and a native signal peptide, a heterologous signal peptide, a hybrid of a native and a heterologous signal peptide, a heterologous protease cleavage site, an epitope tag or an immunoglobulin Fc region.

16. The fusion polypeptide of claim 15, wherein the heterologous signal peptide is selected from the group consisting of:
   a) a CD33 signal peptide, an immunoglobulin signal peptide, a growth hormone signal peptide, an erythropoietin signal peptide, an albumin signal peptide, a secreted alkaline phosphatase signal peptide, and a viral signal peptide; or
   b) a CD33 signal peptide, an IgGκ signal peptide, and a IgGμ signal peptide.

17. The fusion polypeptide of claim 15, comprising a heterologous protease cleavage site or an epitope tag.

18. The fusion polypeptide of claim 15, wherein the fusion polypeptide comprising an amino acid sequence as set forth in any one of SEQ ID NOs: 3-5 and 12-13, has increased production, secretion, or solubility compared to a corresponding native Wnt polypeptide as set forth in SEQ ID NOs: 2 and 6-11.

* * * * *

SEQUENCE LISTING

<160> NUMBER OF SEQ ID NOS: 46

<210> SEQ ID NO 1
<211> LENGTH: 1732
<212> TYPE: DNA
<213> ORGANISM: Homo sapiens

<400> SEQUENCE: 1

```
gagggggcggg ggctggaggc agcagcgccc ccgcactccc cgcgtctcgc acacttgcac      60
cggtcgctcg cgcgcagccc ggcgtcgccc cacgccgcgc tcgctcctcc ctccctcctc     120
ccgctccgtg gctcccgtgc tcctggcgag gctcaggcgc ggagcgcgcg gacgggcgca     180
ccgacagacg gccccgggga cgcctcggct cgcgcctccc gggcgggcta tgttgattgc     240
cccgccgggg ccggcccgcg ggatcagcac agcccggccc gcggcccccgg cggccaatcg     300 ggactatgaa ccggaaagcg cggcgctgcc tgggccacct ctttctcagc ctgggcatgg     360
tctacctccg gatcggtggc ttctcctcag tggtagctct gggcgcaagc atcatctgta     420
acaagatccc aggcctggct cccagacagc gggcgatctg ccagagccgg cccgacgcca     480
tcatcgtcat aggagaaggc tcacaaatgg gcctggacga gtgtcagttt cagttccgca     540
atggccgctg gaactgctct gcactgggag agcgcaccgt cttcgggaag gagctcaaag     600
tggggagccg ggaggctgcg ttcacctacg ccatcattgc cgccggcgtg gcccacgcca     660
tcacagctgc ctgtacccag ggcaacctga gcgactgtgg ctgcgacaaa gagaagcaag     720
gccagtacca ccgggacgag ggctggaagt ggggtggctg ctctgccgac atccgctacg     780
gcatcggctt cgccaaggtc tttgtggatg cccgggagat caagcagaat gccggactc     840 tcatgaactt gcacaacaac gaggcaggcc gaaagatcct ggaggagaac atgaagctgg     900
aatgtaagtg ccacggcgtg tcaggctcgt gcaccaccaa gacgtgctgg accacactgc     960
cacagtttcg ggagctgggc tacgtgctca aggacaagta caacgaggcc gttcacgtgg    1020
agcctgtgcg tgccagccgc aacaagcggc ccaccttcct gaagatcaag aagccactgt    1080
cgtaccgcaa gcccatggac acggacctgg tgtacatcga gaagtcgccc aactactgcg    1140
aggaggaccc ggtgaccggc agtgtgggca cccaggccgc cgcctgcaac aagacggctc    1200
cccaggccag cggctgtgac ctcatgtgct gtgggcgtgg ctacaacacc caccagtacg    1260
cccgcgtgtg gcagtgcaac tgtaagttcc actggtgctg ctatgtcaag tgcaacacgt    1320
gcagcgagcg cacggagatg tacacgtgca agtgagcccc gtgtgcacac caccctcccg    1380
ctgcaagtca gattgctggg aggactggac cgtttccaag ctgcgggctc cctggcagga    1440
tgctgagctt gtcttttctg ctgaggaggg tactttttcct gggtttcctg caggcatccg    1500 tggggaaaa aaaatctctc agagccctca actattctgt tccacaccca atgctgctcc    1560
```

```
accctccccc agacacagcc caggtccctc cgcggctgga gcgaagcctt ctgcagcagg    1620
aactctggac ccctgggcct catcacagca atatttaaca atttattctg ataaaaataa    1680
tattaattta tttaattaaa aagaattctt ccacaaaaaa aaaaaaaaaa aa            1732
```

<210> SEQ ID NO 2
<211> LENGTH: 349
<212> TYPE: PRT
<213> ORGANISM: Homo sapiens

<400> SEQUENCE: 2

```
Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345
```

```
<210> SEQ ID NO 3
<211> LENGTH: 349
<212> TYPE: PRT
<213> ORGANISM: Artificial Sequence
<220> FEATURE:
<223> OTHER INFORMATION: Engineered mutation of human Wnt-7A polypeptide

<400> SEQUENCE: 3
```

| | | | | | | | | | | | | | | |
|---|---|---|---|---|---|---|---|---|---|---|---|---|---|---|
| Met | Asn | Arg | Lys | Ala | Arg | Arg | Cys | Leu | Gly | His | Leu | Phe | Leu | Ser | Leu |
| 1 | | | | 5 | | | | | 10 | | | | | 15 | |
| Gly | Met | Val | Tyr | Leu | Arg | Ile | Gly | Gly | Phe | Ser | Ser | Val | Val | Ala | Leu |
| | | | 20 | | | | | 25 | | | | | 30 | | |
| Gly | Ala | Ser | Ile | Ile | Cys | Asn | Lys | Ile | Pro | Gly | Leu | Ala | Pro | Arg | Gln |
| | | 35 | | | | | 40 | | | | | 45 | | | |
| Arg | Ala | Ile | Cys | Gln | Ser | Arg | Pro | Asp | Ala | Ile | Ile | Val | Ile | Gly | Glu |
| | 50 | | | | | 55 | | | | | 60 | | | | |
| Gly | Ser | Gln | Met | Gly | Leu | Asp | Glu | Ala | Gln | Phe | Gln | Phe | Arg | Asn | Gly |
| 65 | | | | | 70 | | | | | 75 | | | | | 80 |
| Arg | Trp | Asn | Cys | Ser | Ala | Leu | Gly | Glu | Arg | Thr | Val | Phe | Gly | Lys | Glu |
| | | | | 85 | | | | | 90 | | | | | 95 | |
| Leu | Lys | Val | Gly | Ser | Arg | Glu | Ala | Ala | Phe | Thr | Tyr | Ala | Ile | Ile | Ala |
| | | | 100 | | | | | 105 | | | | | 110 | | |
| Ala | Gly | Val | Ala | His | Ala | Ile | Thr | Ala | Ala | Cys | Thr | Gln | Gly | Asn | Leu |
| | | 115 | | | | | 120 | | | | | 125 | | | |
| Ser | Asp | Cys | Gly | Cys | Asp | Lys | Glu | Lys | Gln | Gly | Gln | Tyr | His | Arg | Asp |
| | 130 | | | | | 135 | | | | | 140 | | | | |
| Glu | Gly | Trp | Lys | Trp | Gly | Gly | Cys | Ser | Ala | Asp | Ile | Arg | Tyr | Gly | Ile |
| 145 | | | | | 150 | | | | | 155 | | | | | 160 |
| Gly | Phe | Ala | Lys | Val | Phe | Val | Asp | Ala | Arg | Glu | Ile | Lys | Gln | Asn | Ala |
| | | | | 165 | | | | | 170 | | | | | 175 | |
| Arg | Thr | Leu | Met | Asn | Leu | His | Asn | Asn | Glu | Ala | Gly | Arg | Lys | Ile | Leu |
| | | | 180 | | | | | 185 | | | | | 190 | | |
| Glu | Glu | Asn | Met | Lys | Leu | Glu | Cys | Lys | Cys | His | Gly | Val | Ser | Gly | Ser |
| | | 195 | | | | | 200 | | | | | 205 | | | |
| Cys | Thr | Thr | Lys | Thr | Cys | Trp | Thr | Thr | Leu | Pro | Gln | Phe | Arg | Glu | Leu |
| | 210 | | | | | 215 | | | | | 220 | | | | |
| Gly | Tyr | Val | Leu | Lys | Asp | Lys | Tyr | Asn | Glu | Ala | Val | His | Val | Glu | Pro |
| 225 | | | | | 230 | | | | | 235 | | | | | 240 |
| Val | Arg | Ala | Ser | Arg | Asn | Lys | Arg | Pro | Thr | Phe | Leu | Lys | Ile | Lys | Lys |
| | | | | 245 | | | | | 250 | | | | | 255 | |
| Pro | Leu | Ser | Tyr | Arg | Lys | Pro | Met | Asp | Thr | Asp | Leu | Val | Tyr | Ile | Glu |
| | | | 260 | | | | | 265 | | | | | 270 | | |
| Lys | Ser | Pro | Asn | Tyr | Cys | Glu | Glu | Asp | Pro | Val | Thr | Gly | Ser | Val | Gly |
| | | 275 | | | | | 280 | | | | | 285 | | | |
| Thr | Gln | Gly | Arg | Ala | Cys | Asn | Lys | Thr | Ala | Pro | Gln | Ala | Ser | Gly | Cys |
| | 290 | | | | | 295 | | | | | 300 | | | | |
| Asp | Leu | Met | Cys | Cys | Gly | Arg | Gly | Tyr | Asn | Thr | His | Gln | Tyr | Ala | Arg |
| 305 | | | | | 310 | | | | | 315 | | | | | 320 |
| Val | Trp | Gln | Cys | Asn | Cys | Lys | Phe | His | Trp | Cys | Cys | Tyr | Val | Lys | Cys |
| | | | | 325 | | | | | 330 | | | | | 335 | |
| Asn | Thr | Cys | Ser | Glu | Arg | Thr | Glu | Met | Tyr | Thr | Cys | Lys | | | |
| | | | 340 | | | | | 345 | | | | | | | |

```
<210> SEQ ID NO 4
```

-continued

```
<211> LENGTH: 349
<212> TYPE: PRT
<213> ORGANISM: Artificial Sequence
<220> FEATURE:
<223> OTHER INFORMATION: Engineered mutation of human Wnt-7A polypeptide

<400> SEQUENCE: 4

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ala Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 5
<211> LENGTH: 349
<212> TYPE: PRT
<213> ORGANISM: Artificial Sequence
```

<220> FEATURE:
<223> OTHER INFORMATION: Engineered mutation of human Wnt-7A polypeptide

<400> SEQUENCE: 5

```
Met Asn Arg Lys Ala Arg Cys Leu Gly His Leu Phe Leu Ser Leu
1               5                   10                  15

Gly Met Val Tyr Leu Arg Ile Gly Phe Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Leu Asp Glu Ala Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ala Gly Ser
        195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345
```

<210> SEQ ID NO 6
<211> LENGTH: 349
<212> TYPE: PRT
<213> ORGANISM: Mus musculus

<400> SEQUENCE: 6

```
Met Thr Arg Lys Ala Arg Arg Cys Leu Gly His Leu Phe Leu Ser Leu
1               5                   10                  15

Gly Ile Val Tyr Leu Arg Ile Gly Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
        130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
                180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
        290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 7
<211> LENGTH: 349
<212> TYPE: PRT
<213> ORGANISM: Rattus norvegicus

<400> SEQUENCE: 7

Met Thr Arg Lys Ala Arg Arg Cys Leu Gly His Leu Phe Leu Ser Leu
1               5                   10                  15

Gly Ile Val Tyr Leu Arg Ile Gly Asp Phe Ser Ser Val Val Ala Leu
                20                  25                  30
```

```
Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
 50                  55                  60

Gly Ser Gln Met Gly Leu Asp Glu Cys Gln Phe Gln Phe Arg Asn Gly
 65                  70                  75                  80

Arg Trp Asn Cys Ser Ala Leu Gly Glu Arg Thr Val Phe Gly Lys Glu
                 85                  90                  95

Leu Lys Val Gly Ser Arg Glu Ala Ala Phe Thr Tyr Ala Ile Ile Ala
                100                 105                 110

Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
            290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 8
<211> LENGTH: 349
<212> TYPE: PRT
<213> ORGANISM: Gallus gallus

<400> SEQUENCE: 8

Met Asn Arg Lys Thr Arg Trp Ile Phe His Ile Phe Leu Ser Leu
 1               5                  10                  15

Gly Ile Val Tyr Ile Lys Ile Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
 50                  55                  60
```

```
                 50                 55                 60
Gly Ser Gln Met Gly Ile Asn Glu Cys Gln Phe Gln Phe Arg Asn Gly
 65                 70                 75                 80

Arg Trp Asn Cys Ser Ala Leu Gly Glu Arg Thr Val Phe Gly Lys Glu
                85                 90                 95

Leu Lys Val Gly Ser Arg Glu Ala Ala Phe Thr Tyr Ala Ile Ile Ala
                100                105                110

Ala Gly Val Ala His Ala Ile Thr Ala Ala Cys Thr Gln Gly Asn Leu
                115                120                125

Ser Asp Cys Gly Cys Asp Lys Glu Lys Gln Gly Gln Tyr His Lys Glu
                130                135                140

Glu Gly Trp Lys Trp Gly Cys Ser Ala Asp Ile Arg Tyr Gly Ile
145                150                155                160

Gly Phe Ala Lys Val Phe Val Asp Ala Arg Glu Ile Lys Gln Asn Ala
                165                170                175

Arg Thr Leu Met Asn Leu His Asn Asn Glu Ala Gly Arg Lys Ile Leu
                180                185                190

Glu Glu Asn Met Lys Leu Glu Cys Lys Cys His Gly Val Ser Gly Ser
                195                200                205

Cys Thr Thr Lys Thr Cys Trp Thr Thr Leu Pro Lys Phe Arg Glu Leu
210                215                220

Gly Tyr Ile Leu Lys Asp Lys Tyr Asn Glu Ala Val Gln Val Glu Pro
225                230                235                240

Val Arg Ala Ser Arg Asn Lys Arg Pro Thr Phe Leu Lys Ile Lys Lys
                245                250                255

Pro Leu Ser Tyr Arg Lys Pro Met Asp Thr Asp Leu Val Tyr Ile Glu
                260                265                270

Lys Ser Pro Asn Tyr Cys Glu Asp Pro Val Thr Gly Ser Val Gly
                275                280                285

Thr Gln Gly Arg Met Cys Asn Lys Thr Ala Gln Gln Ser Asn Gly Cys
                290                295                300

Asp Leu Met Cys Cys Gly Arg Gly Tyr Asn Thr His Gln Tyr Ser Arg
305                310                315                320

Val Trp Gln Cys Asn Cys Lys Phe His Trp Cys Cys Tyr Val Lys Cys
                325                330                335

Asn Thr Cys Ser Glu Arg Thr Glu Val Tyr Thr Cys Lys
                340                345

<210> SEQ ID NO 9
<211> LENGTH: 349
<212> TYPE: PRT
<213> ORGANISM: Danio rerio

<400> SEQUENCE: 9

Met Ser Arg Lys Thr Arg Arg Trp Ile Phe His Ile Phe Leu Cys Leu
1               5                  10                 15

Gly Ile Ile Tyr Leu Lys Ile Gly Gly Phe Ser Ser Val Val Ala Leu
                20                 25                 30

Gly Ala Ser Ile Ile Cys Asn Lys Ile Pro Gly Leu Ala Pro Arg Gln
                35                 40                 45

Arg Thr Ile Cys Gln Ser Arg Pro Asp Ala Ile Ile Val Ile Gly Glu
                50                 55                 60

Gly Ala Gln Met Gly Ile Asn Glu Cys Gln Phe Gln Phe Lys Asn Gly
 65                 70                 75                 80
```

```
Arg Trp Asn Cys Ser Ala Leu Gly Glu Arg Thr Val Phe Gly Lys Glu
                 85                  90                  95

Leu Lys Val Gly Ser Lys Glu Ala Ala Phe Thr Tyr Ala Ile Ile Ala
            100                 105                 110

Ala Gly Val Ala His Ala Ile Thr Ala Ala Cys Thr Gln Gly Thr Leu
            115                 120                 125

Ser Gly Cys Gly Cys Asp Lys Glu Lys Gln Gly Phe Tyr Asn Gln Glu
            130                 135                 140

Glu Gly Trp Lys Trp Gly Gly Cys Ser Ala Asp Ile Arg Tyr Gly Leu
145                 150                 155                 160

Ser Phe Ser Lys Val Phe Leu Asp Ala Arg Glu Ile Lys Gln Asn Ala
                165                 170                 175

Arg Thr Leu Met Asn Leu His Asn Asn Glu Val Gly Arg Lys Ile Leu
            180                 185                 190

Glu Lys Asn Met Arg Leu Glu Cys Lys Cys His Gly Val Ser Gly Ser
            195                 200                 205

Cys Thr Thr Lys Thr Cys Trp Thr Thr Leu Pro Lys Phe Arg Gln Leu
            210                 215                 220

Gly Tyr Ile Leu Lys Glu Arg Tyr Asn His Ala Val His Val Glu Pro
225                 230                 235                 240

Val Arg Ala Ser Arg Asn Lys Arg Pro Ala Phe Leu Lys Val Lys Lys
                245                 250                 255

Pro Tyr Ser Tyr Arg Lys Pro Met Asp Thr Asp Leu Val Tyr Ile Glu
            260                 265                 270

Lys Ser Pro Asn Tyr Cys Glu Ala Asp Pro Val Thr Gly Ser Met Gly
            275                 280                 285

Thr Gln Gly Arg Ile Cys Asn Lys Thr Ala Gln His Thr Asn Gly Cys
            290                 295                 300

Asp Leu Met Cys Cys Gly Arg Gly Tyr Asn Thr His Gln Tyr Ser Arg
305                 310                 315                 320

Val Trp Gln Cys Asn Cys Lys Phe Leu Trp Cys Cys Tyr Val Lys Cys
                325                 330                 335

Asn Thr Cys Ser Glu Arg Thr Glu Val Tyr Thr Cys Lys
            340                 345

<210> SEQ ID NO 10
<211> LENGTH: 349
<212> TYPE: PRT
<213> ORGANISM: Sus scrofa

<400> SEQUENCE: 10

Met Asn Arg Lys Ala Arg Arg Cys Leu Gly His Leu Phe Leu Ser Leu
1               5                   10                  15

Gly Leu Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
            50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110
```

```
Ala Gly Val Ala His Ala Ile Thr Ala Ala Cys Thr Gln Gly Asn Leu
            115                 120                 125

Ser Asp Cys Gly Cys Asp Lys Glu Lys Gln Gly Gln Tyr His Arg Asp
        130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
            340                 345

<210> SEQ ID NO 11
<211> LENGTH: 349
<212> TYPE: PRT
<213> ORGANISM: Bos taurus

<400> SEQUENCE: 11

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
```

```
                    130                 135                 140
Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
                195                 200                 205

Cys Thr Thr Lys Thr Cys Trp Thr Thr Leu Pro Gln Phe Arg Glu Leu
            210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Ala Phe Leu Lys Ile Lys Lys
                245                 250                 255

Pro Leu Ser Tyr Arg Lys Pro Met Asp Thr Glu Leu Val Tyr Ile Glu
                260                 265                 270

Lys Ser Pro Ser Tyr Cys Glu Glu Asp Pro Ala Thr Gly Ser Val Gly
            275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
                340                 345

<210> SEQ ID NO 12
<211> LENGTH: 353
<212> TYPE: PRT
<213> ORGANISM: Artificial Sequence
<220> FEATURE:
<223> OTHER INFORMATION: Human Wnt7a polypeptide with signal peptide
      of human immunoglobulin kappa chain

<400> SEQUENCE: 12

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
                20                  25                  30

Lys Leu Ala Leu Gly Ala Ser Ile Ile Cys Asn Lys Ile Pro Gly Leu
            35                  40                  45

Ala Pro Arg Gln Arg Ala Ile Cys Gln Ser Arg Pro Asp Ala Ile Ile
50                  55                  60

Val Ile Gly Glu Gly Ser Gln Met Gly Leu Asp Glu Cys Gln Phe Gln
65                  70                  75                  80

Phe Arg Asn Gly Arg Trp Asn Cys Ser Ala Leu Gly Glu Arg Thr Val
                85                  90                  95

Phe Gly Lys Glu Leu Lys Val Gly Ser Arg Glu Ala Ala Phe Thr Tyr
            100                 105                 110

Ala Ile Ile Ala Ala Gly Val Ala His Ala Ile Thr Ala Ala Cys Thr
        115                 120                 125

Gln Gly Asn Leu Ser Asp Cys Gly Cys Asp Lys Glu Lys Gln Gly Gln
    130                 135                 140
```

Tyr His Arg Asp Glu Gly Trp Lys Trp Gly Gly Cys Ser Ala Asp Ile
145                 150                 155                 160

Arg Tyr Gly Ile Gly Phe Ala Lys Val Phe Val Asp Ala Arg Glu Ile
            165                 170                 175

Lys Gln Asn Ala Arg Thr Leu Met Asn Leu His Asn Asn Glu Ala Gly
        180                 185                 190

Arg Lys Ile Leu Glu Glu Asn Met Lys Leu Glu Cys Lys Cys His Gly
    195                 200                 205

Val Ser Gly Ser Cys Thr Thr Lys Thr Cys Trp Thr Thr Leu Pro Gln
210                 215                 220

Phe Arg Glu Leu Gly Tyr Val Leu Lys Asp Lys Tyr Asn Glu Ala Val
225                 230                 235                 240

His Val Glu Pro Val Arg Ala Ser Arg Asn Lys Arg Pro Thr Phe Leu
            245                 250                 255

Lys Ile Lys Lys Pro Leu Ser Tyr Arg Lys Pro Met Asp Thr Asp Leu
        260                 265                 270

Val Tyr Ile Glu Lys Ser Pro Asn Tyr Cys Glu Glu Asp Pro Val Thr
    275                 280                 285

Gly Ser Val Gly Thr Gln Gly Arg Ala Cys Asn Lys Thr Ala Pro Gln
290                 295                 300

Ala Ser Gly Cys Asp Leu Met Cys Cys Gly Arg Gly Tyr Asn Thr His
305                 310                 315                 320

Gln Tyr Ala Arg Val Trp Gln Cys Asn Cys Lys Phe His Trp Cys Cys
            325                 330                 335

Tyr Val Lys Cys Asn Thr Cys Ser Glu Arg Thr Glu Met Tyr Thr Cys
        340                 345                 350

Lys

<210> SEQ ID NO 13
<211> LENGTH: 353
<212> TYPE: PRT
<213> ORGANISM: Artificial Sequence
<220> FEATURE:
<223> OTHER INFORMATION: Modified human Wnt7a polypeptide with signal
      peptide of human immunoglobulin kappa chain

<400> SEQUENCE: 13

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Leu Gly Ala Ser Ile Ile Cys Asn Lys Ile Pro Gly Leu
        35                  40                  45

Ala Pro Arg Gln Arg Ala Ile Cys Gln Ser Arg Pro Asp Ala Ile Ile
    50                  55                  60

Val Ile Gly Glu Gly Ser Gln Met Gly Leu Asp Glu Ala Gln Phe Gln
65                  70                  75                  80

Phe Arg Asn Gly Arg Trp Asn Cys Ser Ala Leu Gly Glu Arg Thr Val
            85                  90                  95

Phe Gly Lys Glu Leu Lys Val Gly Ser Arg Glu Ala Ala Phe Thr Tyr
        100                 105                 110

Ala Ile Ile Ala Ala Gly Val Ala His Ala Ile Thr Ala Ala Cys Thr
    115                 120                 125

Gln Gly Asn Leu Ser Asp Cys Gly Cys Asp Lys Glu Lys Gln Gly Gln
130                 135                 140

```
Tyr His Arg Asp Glu Gly Trp Lys Trp Gly Gly Cys Ser Ala Asp Ile
145                 150                 155                 160

Arg Tyr Gly Ile Gly Phe Ala Lys Val Phe Val Asp Ala Arg Glu Ile
            165                 170                 175

Lys Gln Asn Ala Arg Thr Leu Met Asn Leu His Asn Asn Glu Ala Gly
        180                 185                 190

Arg Lys Ile Leu Glu Glu Asn Met Lys Leu Glu Cys Lys Cys His Gly
    195                 200                 205

Val Ala Gly Ser Cys Thr Thr Lys Thr Cys Trp Thr Thr Leu Pro Gln
210                 215                 220

Phe Arg Glu Leu Gly Tyr Val Leu Lys Asp Lys Tyr Asn Glu Ala Val
225                 230                 235                 240

His Val Glu Pro Val Arg Ala Ser Arg Asn Lys Arg Pro Thr Phe Leu
            245                 250                 255

Lys Ile Lys Lys Pro Leu Ser Tyr Arg Lys Pro Met Asp Thr Asp Leu
        260                 265                 270

Val Tyr Ile Glu Lys Ser Pro Asn Tyr Cys Glu Glu Asp Pro Val Thr
    275                 280                 285

Gly Ser Val Gly Thr Gln Gly Arg Ala Cys Asn Lys Thr Ala Pro Gln
290                 295                 300

Ala Ser Gly Cys Asp Leu Met Cys Cys Gly Arg Gly Tyr Asn Thr His
305                 310                 315                 320

Gln Tyr Ala Arg Val Trp Gln Cys Asn Cys Lys Phe His Trp Cys Cys
            325                 330                 335

Tyr Val Lys Cys Asn Thr Cys Ser Glu Arg Thr Glu Met Tyr Thr Cys
        340                 345                 350

Lys

<210> SEQ ID NO 14
<211> LENGTH: 1143
<212> TYPE: DNA
<213> ORGANISM: Homo sapiens

<400> SEQUENCE: 14
atgaagaagt ccattggaat attaagccca ggagttgctt tggggatggc tggaagtgca      60
atgtcttcca gttcttcct agtggctttg gccatatttt tctccttcgc ccaggttgta     120
attgaagcca attcttggtg gtcgctaggt atgaataacc tgttcagat gtcagaagta     180 tatattatag gagcacagcc tctctgcagc caactggcag gactttctca aggacagaag     240
aaactgtgcc acttgtatca ggaccacatg cagtacatcg agaaggcgc gaagacaggc     300 atcaaagaat gccagtatca attccgacat cgaaggtgga actgcagcac tgtggataac     360
acctctgttt ttggcagggt gatgcagata ggcagccgcg agacggcctt cacatacgcg     420
gtgagcgcag caggggtggt gaacgccatg agccgggcgt gccgcgaggg cgagctgtcc     480
acctgcggct gcagccgcgc cgcgcgcccc aaggacctgc gcgggactg gctctggggc     540 ggctgcggcg acaacatcga ctatggctac cgctttgcca aggagttcgt ggacgcccgc     600
gagcgggagc gcatccacgc caagggctcc tacgagagtg ctcgcatcct catgaacctg     660
cacaacaacg aggccggccg caggacggtg tacaacctgg ctgatgtggc ctgcaagtgc     720 catgggtgt ccggctcatg tagcctgaag acatgctggc tgcagctggc agacttccgc     780
aaggtgggtg atgccctgaa ggagaagtac gacagcgcgg cggccatgcg gctcaacagc     840
cggggcaagt tggtacaggt caacagccgc ttcaactcgc ccaccacaca agacctggtc     900
```

```
tacatcgacc ccagccctga ctactgcgtg cgcaatgaga gcaccggctc gctgggcacg    960
cagggccgcc tgtgcaacaa gacgtcggag ggcatggatg gctgcgagct catgtgctgc   1020
ggccgtggct acgaccagtt caagaccgtg cagacggagc gctgccactg caagttccac   1080
tggtgctgct acgtcaagtg caagaagtgc acggagatcg tggaccagtt tgtgtgcaag   1140
tag                                                                 1143
```

<210> SEQ ID NO 15
<211> LENGTH: 380
<212> TYPE: PRT
<213> ORGANISM: Homo sapiens

<400> SEQUENCE: 15

```
Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
```

```
                   325                 330                 335
Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
            355                 360                 365

Lys Cys Thr Glu Ile Val Asp Gln Phe Val Cys Lys
            370                 375                 380

<210> SEQ ID NO 16
<211> LENGTH: 380
<212> TYPE: PRT
<213> ORGANISM: Artificial Sequence
<220> FEATURE:
<223> OTHER INFORMATION: Mutated human Wnt5a polypeptide

<400> SEQUENCE: 16

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Ala Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
```

```
                    305                 310                 315                 320
Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
                340                 345                 350

Glu Arg Cys His Cys Lys Phe His Trp Cys Cys Tyr Val Lys Cys Lys
                355                 360                 365

Lys Cys Thr Glu Ile Val Asp Gln Phe Val Cys Lys
                370                 375                 380

<210> SEQ ID NO 17
<211> LENGTH: 380
<212> TYPE: PRT
<213> ORGANISM: Artificial Sequence
<220> FEATURE:
<223> OTHER INFORMATION: Mutated human Wnt5a polypeptide

<400> SEQUENCE: 17

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
                20                  25                  30

Phe Phe Ser Phe Ala Gln Val Val Ile Glu Ala Asn Ser Trp Trp Ser
            35                  40                  45

Leu Gly Met Asn Asn Pro Val Gln Met Ser Glu Val Tyr Ile Ile Gly
        50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
                100                 105                 110

Trp Asn Cys Ser Thr Val Asp Asn Thr Ser Val Phe Gly Arg Val Met
                115                 120                 125

Gln Ile Gly Ser Arg Glu Thr Ala Phe Thr Tyr Ala Val Ser Ala Ala
        130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
                180                 185                 190

Ala Lys Glu Phe Val Asp Ala Arg Glu Arg Glu Arg Ile His Ala Lys
                195                 200                 205

Gly Ser Tyr Glu Ser Ala Arg Ile Leu Met Asn Leu His Asn Asn Glu
        210                 215                 220

Ala Gly Arg Arg Thr Val Tyr Asn Leu Ala Asp Val Ala Cys Lys Cys
225                 230                 235                 240

His Gly Val Ala Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
                260                 265                 270

Ala Ala Ala Met Arg Leu Asn Ser Arg Gly Lys Leu Val Gln Val Asn
                275                 280                 285

Ser Arg Phe Asn Ser Pro Thr Thr Gln Asp Leu Val Tyr Ile Asp Pro
```

```
                290             295             300
Ser Pro Asp Tyr Cys Val Arg Asn Glu Ser Thr Gly Ser Leu Gly Thr
305                 310             315                 320

Gln Gly Arg Leu Cys Asn Lys Thr Ser Glu Gly Met Asp Gly Cys Glu
                325             330             335

Leu Met Cys Cys Gly Arg Gly Tyr Asp Gln Phe Lys Thr Val Gln Thr
                340             345             350

Glu Arg Cys His Cys Lys Phe His Trp Cys Cys Tyr Val Lys Cys Lys
                355             360             365

Lys Cys Thr Glu Ile Val Asp Gln Phe Val Cys Lys
                370             375             380

<210> SEQ ID NO 18
<211> LENGTH: 380
<212> TYPE: PRT
<213> ORGANISM: Artificial Sequence
<220> FEATURE:
<223> OTHER INFORMATION: Mutated human Wnt5a polypeptide

<400> SEQUENCE: 18

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
                20                  25                  30

Phe Phe Ser Phe Ala Gln Val Val Ile Glu Ala Asn Ser Trp Trp Ser
                35                  40                  45

Leu Gly Met Asn Asn Pro Val Gln Met Ser Glu Val Tyr Ile Ile Gly
            50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Ala Gln Tyr Gln Phe Arg His Arg Arg
                100                 105                 110

Trp Asn Cys Ser Thr Val Asp Asn Thr Ser Val Phe Gly Arg Val Met
            115                 120                 125

Gln Ile Gly Ser Arg Glu Thr Ala Phe Thr Tyr Ala Val Ser Ala Ala
            130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
            195                 200                 205

Gly Ser Tyr Glu Ser Ala Arg Ile Leu Met Asn Leu His Asn Asn Glu
            210                 215                 220

Ala Gly Arg Arg Thr Val Tyr Asn Leu Ala Asp Val Ala Cys Lys Cys
225                 230                 235                 240

His Gly Val Ala Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
                260                 265                 270

Ala Ala Ala Met Arg Leu Asn Ser Arg Gly Lys Leu Val Gln Val Asn
```

```
            275                 280                 285
Ser Arg Phe Asn Ser Pro Thr Thr Gln Asp Leu Val Tyr Ile Asp Pro
    290                 295                 300
Ser Pro Asp Tyr Cys Val Arg Asn Glu Ser Thr Gly Ser Leu Gly Thr
305                 310                 315                 320
Gln Gly Arg Leu Cys Asn Lys Thr Ser Glu Gly Met Asp Gly Cys Glu
                325                 330                 335
Leu Met Cys Cys Gly Arg Gly Tyr Asp Gln Phe Lys Thr Val Gln Thr
            340                 345                 350
Glu Arg Cys His Cys Lys Phe His Trp Cys Cys Tyr Val Lys Cys Lys
        355                 360                 365
Lys Cys Thr Glu Ile Val Asp Gln Phe Val Cys Lys
    370                 375                 380
```

<210> SEQ ID NO 19
<211> LENGTH: 380
<212> TYPE: PRT
<213> ORGANISM: Mus musculus

<400> SEQUENCE: 19

```
Met Lys Lys Pro Ile Gly Ile Leu Ser Pro Gly Val Ala Leu Gly Thr
1               5                   10                  15
Ala Gly Gly Ala Met Ser Ser Lys Phe Phe Leu Met Ala Leu Ala Thr
                20                  25                  30
Phe Phe Ser Phe Ala Gln Val Val Ile Glu Ala Asn Ser Trp Trp Ser
            35                  40                  45
Leu Gly Met Asn Asn Pro Val Gln Met Ser Glu Val Tyr Ile Ile Gly
        50                  55                  60
Ala Gln Pro Leu Cys Ser Gln Leu Ala Gly Leu Ser Gln Gly Gln Lys
65                  70                  75                  80
Lys Leu Cys His Leu Tyr Gln Asp His Met Gln Tyr Ile Gly Glu Gly
                85                  90                  95
Ala Lys Thr Gly Ile Lys Glu Cys Gln Tyr Gln Phe Arg His Arg Arg
                100                 105                 110
Trp Asn Cys Ser Thr Val Asp Asn Thr Ser Val Phe Gly Arg Val Met
            115                 120                 125
Gln Ile Gly Ser Arg Glu Thr Ala Phe Thr Tyr Ala Val Ser Ala Ala
        130                 135                 140
Gly Val Val Asn Ala Met Ser Arg Ala Cys Arg Glu Gly Glu Leu Ser
145                 150                 155                 160
Thr Cys Gly Cys Ser Arg Ala Ala Arg Pro Lys Asp Leu Pro Arg Asp
                165                 170                 175
Trp Leu Trp Gly Gly Cys Gly Asp Asn Ile Asp Tyr Gly Tyr Arg Phe
            180                 185                 190
Ala Lys Glu Phe Val Asp Ala Arg Glu Arg Glu Arg Ile His Ala Lys
        195                 200                 205
Gly Ser Tyr Glu Ser Ala Arg Ile Leu Met Asn Leu His Asn Asn Glu
    210                 215                 220
Ala Gly Arg Arg Thr Val Tyr Asn Leu Ala Asp Val Ala Cys Lys Cys
225                 230                 235                 240
His Gly Val Ser Gly Ser Cys Ser Leu Lys Thr Cys Trp Leu Gln Leu
                245                 250                 255
Ala Asp Phe Arg Lys Val Gly Asp Ala Leu Lys Glu Lys Tyr Asp Ser
            260                 265                 270
```

```
Ala Ala Ala Met Arg Leu Asn Ser Arg Gly Lys Leu Val Gln Val Asn
            275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380

<210> SEQ ID NO 20
<211> LENGTH: 379
<212> TYPE: PRT
<213> ORGANISM: Rattus norvegicus

<400> SEQUENCE: 20

Met Lys Lys Pro Ile Gly Ile Leu Ser Pro Gly Val Ala Leu Gly Thr
1               5                   10                  15

Ala Gly Gly Ala Met Ser Ser Lys Phe Phe Leu Met Ala Leu Ala Thr
            20                  25                  30

Phe Phe Ser Phe Ala Gln Val Val Ile Lys Ala Asn Ser Trp Trp Ser
        35                  40                  45

Leu Ser Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Arg Pro Lys Asp Leu Pro Arg Asp Trp
                165                 170                 175

Leu Trp Gly Gly Cys Gly Asp Asn Ile Asp Tyr Gly Tyr Arg Phe Ala
            180                 185                 190

Lys Glu Phe Val Asp Ala Arg Glu Arg Glu Arg Ile His Ala Lys Gly
        195                 200                 205

Ser Tyr Glu Ser Ala Arg Ile Leu Met Asn Leu His Asn Asn Glu Ala
    210                 215                 220

Gly Arg Arg Thr Val Tyr Asn Leu Ala Asp Val Ala Cys Lys Cys His
225                 230                 235                 240

Gly Val Ser Gly Ser Cys Ser Leu Lys Thr Cys Trp Leu Gln Leu Ala
                245                 250                 255

Asp Phe Arg Lys Val Gly Asp Ala Leu Lys Glu Lys Tyr Asp Ser Ala
            260                 265                 270
```

```
Ala Ala Met Arg Leu Asn Ser Arg Gly Lys Leu Val Gln Val Asn Ser
            275                 280                 285

Arg Phe Asn Ser Pro Thr Thr Gln Asp Leu Val Tyr Ile Asp Pro Ser
290                 295                 300

Pro Asp Tyr Cys Val Arg Asn Glu Ser Thr Gly Ser Leu Gly Thr Gln
305                 310                 315                 320

Gly Arg Leu Cys Asn Lys Thr Ser Glu Gly Met Asp Gly Cys Glu Leu
                325                 330                 335

Met Cys Cys Gly Arg Gly Tyr Asp Gln Phe Lys Thr Val Gln Thr Glu
                340                 345                 350

Arg Cys His Cys Lys Phe His Trp Cys Cys Tyr Val Lys Cys Lys Lys
                355                 360                 365

Cys Thr Glu Ile Val Asp Gln Phe Val Cys Lys
                370                 375

<210> SEQ ID NO 21
<211> LENGTH: 385
<212> TYPE: PRT
<213> ORGANISM: Gallus gallus

<400> SEQUENCE: 21

Met Glu Lys Ser Thr Ala Val Leu Ile Gln Gly Gly Ala Leu Gly Thr
1               5                   10                  15

Leu Gly Ser Thr Met Ala Ser Gln Tyr Leu Val Val Ala Leu Ala Ile
                20                  25                  30

Phe Ser Ser Cys Thr Gln Val Val Ile Glu Ala Ser Ser Trp Trp Ser
            35                  40                  45

Leu Gly Met Asn Pro Met Asn Pro Met Asn Pro Val Gln Met Ser Glu
50                  55                  60

Val Tyr Ile Ile Gly Ala Gln Pro Leu Cys Ser Gln Leu Ala Gly Leu
65                  70                  75                  80

Ser Gln Gly Gln Lys Lys Leu Cys Gln Leu Tyr Gln Asp His Met Gln
                85                  90                  95

Phe Ile Gly Glu Gly Ala Lys Thr Gly Ile Lys Glu Cys Gln Tyr Gln
                100                 105                 110

Phe Arg His Arg Arg Trp Asn Cys Ser Thr Val Asp Asn Asn Ser Val
            115                 120                 125

Phe Gly Arg Val Met Gln Ile Gly Ser Arg Glu Thr Ala Phe Thr Tyr
130                 135                 140

Ala Val Ser Ala Ala Gly Val Val Asn Ala Met Ser Arg Ala Cys Arg
145                 150                 155                 160

Glu Gly Glu Leu Ser Ser Cys Gly Cys Ser Arg Ala Ala Arg Pro Lys
                165                 170                 175

Asp Leu Pro Arg Asp Trp Leu Trp Gly Gly Cys Gly Asp Asn Ile Glu
                180                 185                 190

Tyr Gly Tyr Arg Phe Ala Lys Glu Phe Val Asp Ala Arg Glu Arg Glu
            195                 200                 205

Arg Val Tyr Gln Arg Gly Ser Tyr Glu Ser Ala Arg Ile Met Met Asn
210                 215                 220

Leu His Asn Asn Glu Ala Gly Arg Arg Thr Val Tyr Asn Leu Ala Asp
225                 230                 235                 240

Val Ala Cys Lys Cys His Gly Val Ser Gly Ser Cys Ser Leu Lys Thr
                245                 250                 255

Cys Trp Leu Gln Leu Ala Asp Phe Arg Lys Val Gly Asp Ala Leu Lys
```

```
                    260                 265                 270
Glu Lys Tyr Asp Ser Ala Ala Met Lys Leu Asn Ser Arg Gly Lys
            275                 280                 285

Leu Val Gln Met Asn Ser Arg Phe Asn Ala Pro Thr Ile His Asp Leu
            290                 295                 300

Ile Tyr Ile Asp Pro Ser Pro Asp Tyr Cys Met Arg Asn Glu Ser Thr
305                 310                 315                 320

Gly Ser Leu Gly Thr Gln Gly Arg Leu Cys Asn Lys Thr Ser Glu Gly
                325                 330                 335

Met Asp Gly Cys Glu Leu Met Cys Cys Gly Arg Gly Tyr Asp Gln Phe
            340                 345                 350

Lys Thr Val Gln Arg Glu Arg Cys His Cys Lys Phe His Trp Cys Cys
            355                 360                 365

Tyr Val Lys Cys Lys Leu Cys Thr Glu Ile Val Asp Gln Phe Val Cys
            370                 375                 380

Lys
385

<210> SEQ ID NO 22
<211> LENGTH: 374
<212> TYPE: PRT
<213> ORGANISM: Danio rerio

<400> SEQUENCE: 22

Met Met Leu Leu Lys Leu Lys Trp Thr Ser Ser Gly Val Lys Asp Thr
1               5                   10                  15

Pro His Thr Leu Leu Ser Ile Ile Thr Phe Cys Val Phe Phe Met
            20                  25                  30

Leu Glu Ile Val Asp Ala Asn Ser Trp Trp Ser Leu Ala Met Asn Pro
            35                  40                  45

Leu Leu Ile Pro Glu Val Tyr Val Ile Gly Gly Gln Pro Leu Cys Ser
50                  55                  60

Gln Leu Ser Gly Leu Ser Lys Gly Gln Lys Lys Leu Cys Gln Leu Tyr
65                  70                  75                  80

Gln Asp His Met Gln Tyr Ile Gly Glu Gly Ala Lys Thr Gly Ile Arg
                85                  90                  95

Glu Cys Gln His Gln Phe Arg His Arg Arg Trp Asn Cys Ser Thr Val
            100                 105                 110

Asp Asn Ser Thr Val Leu Gly Arg Val Met His Ile Gly Ser Arg Glu
            115                 120                 125

Ser Ala Phe Ala Phe Ala Ile Ser Ala Ala Gly Val Leu His Ala Val
            130                 135                 140

Ser Arg Ala Cys Arg Glu Gly Ala Leu Ser Ser Cys Gly Cys Ser Arg
145                 150                 155                 160

Ala Ser Arg Pro Lys Asp Leu Pro Arg Asp Trp Leu Trp Gly Gly Cys
                165                 170                 175

Gly Asp Asn Leu Asn Tyr Gly Tyr Arg Phe Ser Arg Glu Phe Val Asp
            180                 185                 190

Ala Arg Glu Arg Glu Lys Thr Phe Ser Lys Gly Ser Ala Glu Ser Ala
            195                 200                 205

Arg Gln Met Met Asn Leu His Asn Asn Glu Ala Gly Arg Arg Ile Val
            210                 215                 220

Ser Asp Leu Ala Asp Val Ser Cys Lys Cys His Gly Val Ser Gly Ser
225                 230                 235                 240
```

```
Cys Ser Leu Lys Thr Cys Trp Leu Gln Leu Ala Asp Phe Arg Lys Val
                245                 250                 255

Gly Asp Val Leu Lys Glu Lys Tyr Asp Ser Ala Ala Met Arg Met
            260                 265                 270

Asn Gly Arg Gly Lys Leu Val Gln Met His Ser Lys Phe Ser Pro Pro
            275                 280                 285

Ser Gly Gln Asp Leu Leu Tyr Leu Gln Pro Ser Pro Asp Tyr Cys Ile
            290                 295                 300

Arg Asn Ser Ser Gly Ser Leu Gly Thr Gln Gly Arg Leu Cys Asn
305                 310                 315                 320

Lys Thr Ser Glu Gly Met Asp Gly Cys Ala Leu Met Cys Cys Gly Arg
                325                 330                 335

Gly Tyr Asp Gln Tyr Lys Ala Glu Leu Val Glu Arg Cys His Cys Lys
            340                 345                 350

Phe His Trp Cys Cys Tyr Val Arg Cys Lys Arg Cys Ser Ser Ile Val
            355                 360                 365

Asp Gln Tyr Val Cys Lys
            370

<210> SEQ ID NO 23
<211> LENGTH: 380
<212> TYPE: PRT
<213> ORGANISM: Bos taurus

<400> SEQUENCE: 23

Met Lys Lys Ser Ile Gly Ile Leu Ser Pro Gly Val Ala Trp Gly Thr
1               5                   10                  15

Ala Gly Arg Ala Met Ser Ser Lys Phe Phe Leu Met Ala Leu Ala Ile
            20                  25                  30

Phe Leu Ser Phe Ala Gln Val Val Ile Glu Ala Asn Ser Trp Trp Ser
            35                  40                  45

Leu Gly Met Asn Asn Pro Val Gln Met Ser Glu Val Tyr Ile Ile Gly
            50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
            115                 120                 125

Gln Ile Gly Ser Arg Glu Thr Ala Phe Thr Tyr Ala Val Ser Ala Ala
            130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
            195                 200                 205

Gly Ser Tyr Glu Ser Ala Arg Ile Leu Met Asn Leu His Asn Asn Glu
            210                 215                 220

Ala Gly Arg Arg Thr Val Tyr Ser Leu Ala Asp Val Ala Cys Lys Cys
225                 230                 235                 240
```

```
His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380

<210> SEQ ID NO 24
<211> LENGTH: 370
<212> TYPE: PRT
<213> ORGANISM: Homo sapiens

<400> SEQUENCE: 24

Met Gly Leu Trp Ala Leu Leu Pro Gly Trp Val Ser Ala Thr Leu Leu
1               5                   10                  15

Leu Ala Leu Ala Ala Leu Pro Ala Ala Leu Ala Ala Asn Ser Ser Gly
            20                  25                  30

Arg Trp Trp Gly Ile Val Asn Val Ala Ser Ser Thr Asn Leu Leu Thr
        35                  40                  45

Asp Ser Lys Ser Leu Gln Leu Val Leu Glu Pro Ser Leu Gln Leu Leu
    50                  55                  60

Ser Arg Lys Gln Arg Arg Leu Ile Arg Gln Asn Pro Gly Ile Leu His
65                  70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
        115                 120                 125

Ala Ile Thr Ser Ala Gly Val Thr His Ser Val Ala Arg Ser Cys Ser
    130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
            180                 185                 190

Asp Leu Arg Phe Leu Met Asn Leu His Asn Asn Glu Ala Gly Arg Thr
        195                 200                 205

Thr Val Phe Ser Glu Met Arg Gln Glu Cys Lys Cys His Gly Met Ser
    210                 215                 220

Gly Ser Cys Thr Val Arg Thr Cys Trp Met Arg Leu Pro Thr Leu Arg
```

```
                225                 230                 235                 240
Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
                260                 265                 270

Arg Leu Glu Pro Glu Asp Pro Ala His Lys Pro Ser Pro His Asp
            275                 280                 285

Leu Val Tyr Phe Glu Lys Ser Pro Asn Phe Cys Thr Tyr Ser Gly Arg
            290                 295                 300

Leu Gly Thr Ala Gly Thr Ala Gly Arg Ala Cys Asn Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
            340                 345                 350

Cys His Val Ser Cys Arg Asn Cys Thr His Thr Arg Val Leu His Glu
                355                 360                 365

Cys Leu
    370

<210> SEQ ID NO 25
<211> LENGTH: 360
<212> TYPE: PRT
<213> ORGANISM: Homo sapiens

<400> SEQUENCE: 25

Met Asn Ala Pro Leu Gly Gly Ile Trp Leu Trp Leu Pro Leu Leu Leu
1               5                   10                  15

Thr Trp Leu Thr Pro Glu Val Asn Ser Ser Trp Trp Tyr Met Arg Ala
            20                  25                  30

Thr Gly Gly Ser Ser Arg Val Met Cys Asp Asn Val Pro Gly Leu Val
        35                  40                  45

Ser Ser Gln Arg Gln Leu Cys His Arg His Pro Asp Val Met Arg Ala
    50                  55                  60

Ile Ser Gln Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95

Phe Gly Arg Val Leu Leu Arg Ser Ser Arg Glu Ser Ala Phe Val Tyr
            100                 105                 110

Ala Ile Ser Ser Ala Gly Val Phe Ala Ile Thr Arg Ala Cys Ser
        115                 120                 125

Gln Gly Glu Val Lys Ser Cys Ser Cys Asp Pro Lys Lys Met Gly Ser
    130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175

Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
        195                 200                 205

His Gly Val Ser Gly Ser Cys Thr Leu Arg Thr Cys Trp Leu Ala Met
    210                 215                 220
```

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
            245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
            275                 280                 285

Thr Ala Gly Arg Val Cys Asn Leu Thr Ser Arg Gly Met Asp Ser Cys
            290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
            325                 330                 335

Gln Asp Cys Leu Glu Ala Leu Asp Val His Thr Cys Lys Ala Pro Lys
            340                 345                 350

Asn Ala Asp Trp Thr Thr Ala Thr
            355                 360

<210> SEQ ID NO 26
<211> LENGTH: 372
<212> TYPE: PRT
<213> ORGANISM: Homo sapiens

<400> SEQUENCE: 26

Met Leu Asp Gly Leu Gly Val Val Ala Ile Ser Ile Phe Gly Ile Gln
1               5                   10                  15

Leu Lys Thr Glu Gly Ser Leu Arg Thr Ala Val Pro Gly Ile Pro Thr
            20                  25                  30

Gln Ser Ala Phe Asn Lys Cys Leu Gln Arg Tyr Ile Gly Ala Leu Gly
            35                  40                  45

Ala Arg Val Ile Cys Asp Asn Ile Pro Gly Leu Val Ser Arg Gln Arg
        50                  55                  60

Gln Leu Cys Gln Arg Tyr Pro Asp Ile Met Arg Ser Val Gly Glu Gly
65                  70                  75                  80

Ala Arg Glu Trp Ile Arg Glu Cys Gln His Gln Phe Arg His His Arg
                85                  90                  95

Trp Asn Cys Thr Thr Leu Asp Arg Asp His Thr Val Phe Gly Arg Val
            100                 105                 110

Met Leu Arg Ser Ser Arg Glu Ala Ala Phe Val Tyr Ala Ile Ser Ser
            115                 120                 125

Ala Gly Val Val His Ala Ile Thr Arg Ala Cys Ser Gln Gly Glu Leu
            130                 135                 140

Ser Val Cys Ser Cys Asp Pro Tyr Thr Arg Gly Arg His His Asp Gln
145                 150                 155                 160

Arg Gly Asp Phe Asp Trp Gly Gly Cys Ser Asp Asn Ile His Tyr Gly
            165                 170                 175

Val Arg Phe Ala Lys Ala Phe Val Asp Ala Lys Glu Lys Arg Leu Lys
            180                 185                 190

Asp Ala Arg Ala Leu Met Asn Leu His Asn Asn Arg Cys Gly Arg Thr
            195                 200                 205

Ala Val Arg Arg Phe Leu Lys Leu Glu Cys Lys Cys His Gly Val Ser
            210                 215                 220

Gly Ser Cys Thr Leu Arg Thr Cys Trp Arg Ala Leu Ser Asp Phe Arg
225                 230                 235                 240

```
Arg Thr Gly Asp Tyr Leu Arg Arg Tyr Asp Gly Ala Val Gln Val
            245                 250                 255

Met Ala Thr Gln Asp Gly Ala Asn Phe Thr Ala Arg Gln Gly Tyr
        260                 265                 270

Arg Arg Ala Thr Arg Thr Asp Leu Val Tyr Phe Asp Asn Ser Pro Asp
        275                 280                 285

Tyr Cys Val Leu Asp Lys Ala Ala Gly Ser Leu Gly Thr Ala Gly Arg
        290                 295                 300

Val Cys Ser Lys Thr Ser Lys Gly Thr Asp Gly Cys Glu Ile Met Cys
305                 310                 315                 320

Cys Gly Arg Gly Tyr Asp Thr Thr Arg Val Thr Arg Val Thr Gln Cys
                325                 330                 335

Glu Cys Lys Phe His Trp Cys Cys Ala Val Arg Cys Lys Glu Cys Arg
                340                 345                 350

Asn Thr Val Asp Val His Thr Cys Lys Ala Pro Lys Lys Ala Glu Trp
            355                 360                 365

Leu Asp Gln Thr
        370

<210> SEQ ID NO 27
<211> LENGTH: 355
<212> TYPE: PRT
<213> ORGANISM: Homo sapiens

<400> SEQUENCE: 27

Met Glu Pro His Leu Leu Gly Leu Leu Gly Leu Leu Gly Gly
1               5                   10                  15

Thr Arg Val Leu Ala Gly Tyr Pro Ile Trp Trp Ser Leu Ala Leu Gly
            20                  25                  30

Gln Gln Tyr Thr Ser Leu Gly Ser Gln Pro Leu Leu Cys Gly Ser Ile
        35                  40                  45

Pro Gly Leu Val Pro Lys Gln Leu Arg Phe Cys Arg Asn Tyr Ile Glu
    50                  55                  60

Ile Met Pro Ser Val Ala Glu Gly Val Lys Leu Gly Ile Gln Glu Cys
65                  70                  75                  80

Gln His Gln Phe Arg Gly Arg Arg Trp Asn Cys Thr Thr Ile Asp Asp
                85                  90                  95

Ser Leu Ala Ile Phe Gly Pro Val Leu Asp Lys Ala Thr Arg Glu Ser
            100                 105                 110

Ala Phe Val His Ala Ile Ala Ser Ala Gly Val Ala Phe Ala Val Thr
        115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205

His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
```

```
               225                 230                 235                 240
Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
                260                 265                 270

Asp Leu Val Tyr Tyr Glu Asn Ser Pro Asn Phe Cys Glu Pro Asn Pro
                275                 280                 285

Glu Thr Gly Ser Phe Gly Thr Arg Asp Arg Thr Cys Asn Val Thr Ser
                290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
                340                 345                 350

Thr Cys Lys
        355

<210> SEQ ID NO 28
<211> LENGTH: 352
<212> TYPE: PRT
<213> ORGANISM: Homo sapiens

<400> SEQUENCE: 28

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
                20                  25                  30

Ser Ser Leu Gly Ser Gln Pro Ile Leu Cys Ala Ser Ile Pro Gly Leu
            35                  40                  45

Val Pro Lys Gln Leu Arg Phe Cys Arg Asn Tyr Val Glu Ile Met Pro
        50                  55                  60

Ser Val Ala Glu Gly Ile Lys Ile Gly Ile Gln Glu Cys Gln His Gln
65              70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
                100                 105                 110

His Ala Ile Ala Ser Ala Gly Val Ala Phe Ala Val Thr Arg Ser Cys
            115                 120                 125

Ala Glu Gly Thr Ala Ala Ile Cys Gly Cys Ser Ser Arg His Gln Gly
        130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
                180                 185                 190

Gln Ala Ile Ala Ser His Met His Leu Lys Cys Lys Cys His Gly Leu
            195                 200                 205

Ser Gly Ser Cys Glu Val Lys Thr Cys Trp Trp Ser Gln Pro Asp Phe
        210                 215                 220

Arg Ala Ile Gly Asp Phe Leu Lys Asp Lys Tyr Asp Ser Ala Ser Glu
225                 230                 235                 240
```

Met Val Val Glu Lys His Arg Glu Ser Arg Gly Trp Val Glu Thr Leu
            245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
            290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
            325                 330                 335

Val Ser Cys Gln Glu Cys Thr Arg Val Tyr Asp Val His Thr Cys Lys
            340                 345                 350

<210> SEQ ID NO 29
<211> LENGTH: 351
<212> TYPE: PRT
<213> ORGANISM: Homo sapiens

<400> SEQUENCE: 29

Met Ser Pro Arg Ser Cys Leu Arg Ser Leu Arg Leu Leu Val Phe Ala
1               5                   10                  15

Val Phe Ser Ala Ala Ala Ser Asn Trp Leu Tyr Leu Ala Lys Leu Ser
            20                  25                  30

Ser Val Gly Ser Ile Ser Glu Glu Thr Cys Glu Lys Leu Lys Gly
            35                  40                  45

Leu Ile Gln Arg Gln Val Gln Met Cys Lys Arg Asn Leu Glu Val Met
50                  55                  60

Asp Ser Val Arg Arg Gly Ala Gln Leu Ala Ile Glu Glu Cys Gln Tyr
65                  70                  75                  80

Gln Phe Arg Asn Arg Arg Trp Asn Cys Ser Thr Leu Asp Ser Leu Pro
            85                  90                  95

Val Phe Gly Lys Val Val Thr Gln Gly Thr Arg Glu Ala Ala Phe Val
            100                 105                 110

Tyr Ala Ile Ser Ser Ala Gly Val Ala Phe Ala Val Thr Arg Ala Cys
            115                 120                 125

Ser Ser Gly Glu Leu Glu Lys Cys Gly Cys Asp Arg Thr Val His Gly
            130                 135                 140

Val Ser Pro Gln Gly Phe Gln Trp Ser Gly Cys Ser Asp Asn Ile Ala
145                 150                 155                 160

Tyr Gly Val Ala Phe Ser Gln Ser Phe Val Asp Val Arg Glu Arg Ser
            165                 170                 175

Lys Gly Ala Ser Ser Arg Ala Leu Met Asn Leu His Asn Asn Glu
            180                 185                 190

Ala Gly Arg Lys Ala Ile Leu Thr His Met Arg Val Glu Cys Lys Cys
            195                 200                 205

His Gly Val Ser Gly Ser Cys Glu Val Lys Thr Cys Trp Arg Ala Val
            210                 215                 220

Pro Pro Phe Arg Gln Val Gly His Ala Leu Lys Glu Lys Phe Asp Gly
225                 230                 235                 240

Ala Thr Glu Val Glu Pro Arg Arg Val Gly Ser Ser Arg Ala Leu Val
            245                 250                 255

Pro Arg Asn Ala Gln Phe Lys Pro His Thr Asp Glu Asp Leu Val Tyr
            260                 265                 270

```
Leu Glu Pro Ser Pro Asp Phe Cys Glu Gln Asp Met Arg Ser Gly Val
            275                 280                 285

Leu Gly Thr Arg Gly Arg Thr Cys Asn Lys Thr Ser Lys Ala Ile Asp
        290                 295                 300

Gly Cys Glu Leu Leu Cys Cys Gly Arg Gly Phe His Thr Ala Gln Val
305                 310                 315                 320

Glu Leu Ala Glu Arg Cys Ser Cys Lys Phe His Trp Cys Cys Phe Val
                325                 330                 335

Lys Cys Arg Gln Cys Gln Arg Leu Val Glu Leu His Thr Cys Arg
            340                 345                 350

<210> SEQ ID NO 30
<211> LENGTH: 359
<212> TYPE: PRT
<213> ORGANISM: Homo sapiens

<400> SEQUENCE: 30

Met Pro Ser Leu Leu Leu Phe Thr Ala Ala Leu Leu Ser Ser Trp
1               5                   10                  15

Ala Gln Leu Leu Thr Asp Ala Asn Ser Trp Trp Ser Leu Ala Leu Asn
            20                  25                  30

Pro Val Gln Arg Pro Glu Met Phe Ile Ile Gly Ala Gln Pro Val Cys
        35                  40                  45

Ser Gln Leu Pro Gly Leu Ser Pro Gly Gln Arg Lys Leu Cys Gln Leu
    50                  55                  60

Tyr Gln Glu His Met Ala Tyr Ile Gly Glu Gly Ala Lys Thr Gly Ile
65              70                  75                  80

Lys Glu Cys Gln His Gln Phe Arg Gln Arg Trp Asn Cys Ser Thr
            85                  90                  95

Ala Asp Asn Ala Ser Val Phe Gly Arg Val Met Gln Ile Gly Ser Arg
                100                 105                 110

Glu Thr Ala Phe Thr His Ala Val Ser Ala Ala Gly Val Val Asn Ala
            115                 120                 125

Ile Ser Arg Ala Cys Arg Glu Gly Glu Leu Ser Thr Cys Gly Cys Ser
        130                 135                 140

Arg Thr Ala Arg Pro Lys Asp Leu Pro Arg Asp Trp Leu Trp Gly Gly
145                 150                 155                 160

Cys Gly Asp Asn Val Glu Tyr Gly Tyr Arg Phe Ala Lys Glu Phe Val
                165                 170                 175

Asp Ala Arg Glu Arg Glu Lys Asn Phe Ala Lys Gly Ser Glu Glu Gln
            180                 185                 190

Gly Arg Val Leu Met Asn Leu Gln Asn Asn Glu Ala Gly Arg Arg Ala
        195                 200                 205

Val Tyr Lys Met Ala Asp Val Ala Cys Lys Cys His Gly Val Ser Gly
    210                 215                 220

Ser Cys Ser Leu Lys Thr Cys Trp Leu Gln Leu Ala Glu Phe Arg Lys
225                 230                 235                 240

Val Gly Asp Arg Leu Lys Glu Lys Tyr Asp Ser Ala Ala Ala Met Arg
                245                 250                 255

Val Thr Arg Lys Gly Arg Leu Glu Leu Val Asn Ser Arg Phe Thr Gln
            260                 265                 270

Pro Thr Pro Glu Asp Leu Val Tyr Val Asp Pro Ser Pro Asp Tyr Cys
        275                 280                 285

Leu Arg Asn Glu Ser Thr Gly Ser Leu Gly Thr Gln Gly Arg Leu Cys
```

```
                    290                 295                 300
Asn Lys Thr Ser Glu Gly Met Asp Gly Cys Glu Leu Met Cys Cys Gly
305                 310                 315                 320

Arg Gly Tyr Asn Gln Phe Lys Ser Val Gln Val Glu Arg Cys His Cys
                    325                 330                 335

Lys Phe His Trp Cys Cys Phe Val Arg Cys Lys Lys Cys Thr Glu Ile
                    340                 345                 350

Val Asp Gln Tyr Ile Cys Lys
                    355

<210> SEQ ID NO 31
<211> LENGTH: 365
<212> TYPE: PRT
<213> ORGANISM: Homo sapiens

<400> SEQUENCE: 31

Met Leu Pro Pro Leu Pro Ser Arg Leu Gly Leu Leu Leu Leu Leu Leu
1               5                   10                  15

Leu Cys Pro Ala His Val Gly Gly Leu Trp Trp Ala Val Gly Ser Pro
                20                  25                  30

Leu Val Met Asp Pro Thr Ser Ile Cys Arg Lys Ala Arg Arg Leu Ala
            35                  40                  45

Gly Arg Gln Ala Glu Leu Cys Gln Ala Glu Pro Glu Val Val Ala Glu
50                  55                  60

Leu Ala Arg Gly Ala Arg Leu Gly Val Arg Glu Cys Gln Phe Gln Phe
65                  70                  75                  80

Arg Phe Arg Arg Trp Asn Cys Ser Ser His Ser Lys Ala Phe Gly Arg
                85                  90                  95

Ile Leu Gln Gln Asp Ile Arg Glu Thr Ala Phe Val Phe Ala Ile Thr
                100                 105                 110

Ala Ala Gly Ala Ser His Ala Val Thr Gln Ala Cys Ser Met Gly Glu
            115                 120                 125

Leu Leu Gln Cys Gly Cys Gln Ala Pro Arg Gly Arg Ala Pro Pro Arg
130                 135                 140

Pro Ser Gly Leu Pro Gly Thr Pro Gly Pro Pro Gly Pro Ala Gly Ser
145                 150                 155                 160

Pro Glu Gly Ser Ala Ala Trp Glu Trp Gly Gly Cys Gly Asp Asp Val
                165                 170                 175

Asp Phe Gly Asp Glu Lys Ser Arg Leu Phe Met Asp Ala Arg His Lys
                180                 185                 190

Arg Gly Arg Gly Asp Ile Arg Ala Leu Val Gln Leu His Asn Asn Glu
            195                 200                 205

Ala Gly Arg Leu Ala Val Arg Ser His Thr Arg Thr Glu Cys Lys Cys
210                 215                 220

His Gly Leu Ser Gly Ser Cys Ala Leu Arg Thr Cys Trp Gln Lys Leu
225                 230                 235                 240

Pro Pro Phe Arg Glu Val Gly Ala Arg Leu Leu Glu Arg Phe His Gly
                245                 250                 255

Ala Ser Arg Val Met Gly Thr Asn Asp Gly Lys Ala Leu Leu Pro Ala
                260                 265                 270

Val Arg Thr Leu Lys Pro Pro Gly Arg Ala Asp Leu Leu Tyr Ala Ala
            275                 280                 285

Asp Ser Pro Asp Phe Cys Ala Pro Asn Arg Arg Thr Gly Ser Pro Gly
290                 295                 300
```

```
Thr Arg Gly Arg Ala Cys Asn Ser Ser Ala Pro Asp Leu Ser Gly Cys
305                 310                 315                 320

Asp Leu Leu Cys Cys Gly Arg Gly His Arg Gln Glu Ser Val Gln Leu
                325                 330                 335

Glu Glu Asn Cys Leu Cys Arg Phe His Trp Cys Cys Val Val Gln Cys
            340                 345                 350

His Arg Cys Arg Val Arg Lys Glu Leu Ser Leu Cys Leu
        355                 360                 365

<210> SEQ ID NO 32
<211> LENGTH: 349
<212> TYPE: PRT
<213> ORGANISM: Homo sapiens

<400> SEQUENCE: 32

Met His Arg Asn Phe Arg Lys Trp Ile Phe Tyr Val Phe Leu Cys Phe
1               5                   10                  15

Gly Val Leu Tyr Val Lys Leu Gly Ala Leu Ser Ser Val Ala Leu
            20                  25                  30

Gly Ala Asn Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320
```

-continued

Val Trp Gln Cys Asn Cys Lys Phe His Trp Cys Cys Phe Val Lys Cys
            325                 330                 335

Asn Thr Cys Ser Glu Arg Thr Glu Val Phe Thr Cys Lys
            340                 345

<210> SEQ ID NO 33
<211> LENGTH: 351
<212> TYPE: PRT
<213> ORGANISM: Homo sapiens

<400> SEQUENCE: 33

Met Gly Asn Leu Phe Met Leu Trp Ala Ala Leu Gly Ile Cys Cys Ala
1               5                   10                  15

Ala Phe Ser Ala Ser Ala Trp Ser Val Asn Asn Phe Leu Ile Thr Gly
            20                  25                  30

Pro Lys Ala Tyr Leu Thr Tyr Thr Thr Ser Val Ala Leu Gly Ala Gln
        35                  40                  45

Ser Gly Ile Glu Glu Cys Lys Phe Gln Phe Ala Trp Glu Arg Trp Asn
50                  55                  60

Cys Pro Glu Asn Ala Leu Gln Leu Ser Thr His Asn Arg Leu Arg Ser
65                  70                  75                  80

Ala Thr Arg Glu Thr Ser Phe Ile His Ala Ile Ser Ser Ala Gly Val
                85                  90                  95

Met Tyr Ile Ile Thr Lys Asn Cys Ser Met Gly Asp Phe Glu Asn Cys
            100                 105                 110

Gly Cys Asp Gly Ser Asn Asn Gly Lys Thr Gly His Gly Trp Ile
            115                 120                 125

Trp Gly Gly Cys Ser Asp Asn Val Glu Phe Gly Glu Arg Ile Ser Lys
130                 135                 140

Leu Phe Val Asp Ser Leu Glu Lys Gly Lys Asp Ala Arg Ala Leu Met
145                 150                 155                 160

Asn Leu His Asn Asn Arg Ala Gly Arg Leu Ala Val Arg Ala Thr Met
                165                 170                 175

Lys Arg Thr Cys Lys Cys His Gly Ile Ser Gly Ser Cys Ser Ile Gln
            180                 185                 190

Thr Cys Trp Leu Gln Leu Ala Glu Phe Arg Glu Met Gly Asp Tyr Leu
        195                 200                 205

Lys Ala Lys Tyr Asp Gln Ala Leu Lys Ile Glu Met Asp Lys Arg Gln
    210                 215                 220

Leu Arg Ala Gly Asn Ser Ala Glu Gly His Trp Val Pro Ala Glu Ala
225                 230                 235                 240

Phe Leu Pro Ser Ala Glu Ala Glu Leu Ile Phe Leu Glu Glu Ser Pro
                245                 250                 255

Asp Tyr Cys Thr Cys Asn Ser Ser Leu Gly Ile Tyr Gly Thr Glu Gly
            260                 265                 270

Arg Glu Cys Leu Gln Asn Ser His Asn Thr Ser Arg Trp Glu Arg Arg
        275                 280                 285

Ser Cys Gly Arg Leu Cys Thr Glu Cys Gly Leu Gln Val Glu Glu Arg
    290                 295                 300

Lys Thr Glu Val Ile Ser Ser Cys Asn Cys Lys Phe Gln Trp Cys Cys
305                 310                 315                 320

Thr Val Lys Cys Asp Gln Cys Arg His Val Val Ser Lys Tyr Tyr Cys
                325                 330                 335

Ala Arg Ser Pro Gly Ser Ala Gln Ser Leu Gly Lys Gly Ser Ala

<210> SEQ ID NO 34
<211> LENGTH: 351
<212> TYPE: PRT
<213> ORGANISM: Homo sapiens

<400> SEQUENCE: 34

Met Phe Leu Ser Lys Pro Ser Val Tyr Ile Cys Leu Phe Thr Cys Val
1               5                   10                  15

Leu Gln Leu Ser His Ser Trp Ser Val Asn Asn Phe Leu Met Thr Gly
            20                  25                  30

Pro Lys Ala Tyr Leu Ile Tyr Ser Ser Val Ala Ala Gly Ala Gln
        35                  40                  45

Ser Gly Ile Glu Glu Cys Lys Tyr Gln Phe Ala Trp Asp Arg Trp Asn
50                  55                  60

Cys Pro Glu Arg Ala Leu Gln Leu Ser Ser His Gly Gly Leu Arg Ser
65                  70                  75                  80

Ala Asn Arg Glu Thr Ala Phe Val His Ala Ile Ser Ser Ala Gly Val
                85                  90                  95

Met Tyr Thr Leu Thr Arg Asn Cys Ser Leu Gly Asp Phe Asp Asn Cys
            100                 105                 110

Gly Cys Asp Asp Ser Arg Asn Gly Gln Leu Gly Gly Gln Gly Trp Leu
        115                 120                 125

Trp Gly Gly Cys Ser Asp Asn Val Gly Phe Gly Glu Ala Ile Ser Lys
130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
                165                 170                 175

Lys Arg Thr Cys Lys Cys His Gly Val Ser Gly Ser Cys Thr Thr Gln
            180                 185                 190

Thr Cys Trp Leu Gln Leu Pro Glu Phe Arg Glu Val Gly Ala His Leu
        195                 200                 205

Lys Glu Lys Tyr His Ala Ala Leu Lys Val Asp Leu Leu Gln Gly Ala
210                 215                 220

Gly Asn Ser Ala Ala Gly Arg Gly Ala Ile Ala Asp Thr Phe Arg Ser
225                 230                 235                 240

Ile Ser Thr Arg Glu Leu Val His Leu Glu Asp Ser Pro Asp Tyr Cys
                245                 250                 255

Leu Glu Asn Lys Thr Leu Gly Leu Leu Gly Thr Glu Gly Arg Glu Cys
            260                 265                 270

Leu Arg Arg Gly Arg Ala Leu Gly Arg Trp Glu Arg Ser Cys Arg
        275                 280                 285

Arg Leu Cys Gly Asp Cys Gly Leu Ala Val Glu Glu Arg Arg Ala Glu
290                 295                 300

Thr Val Ser Ser Cys Asn Cys Lys Phe His Trp Cys Cys Ala Val Arg
305                 310                 315                 320

Cys Glu Gln Cys Arg Arg Arg Val Thr Lys Tyr Phe Cys Ser Arg Ala
                325                 330                 335

Glu Arg Pro Arg Gly Gly Ala Ala His Lys Pro Gly Arg Lys Pro
            340                 345                 350

<210> SEQ ID NO 35
<211> LENGTH: 365

```
<212> TYPE: PRT
<213> ORGANISM: Homo sapiens

<400> SEQUENCE: 35

Met Leu Asp Gly Ser Pro Leu Ala Arg Trp Leu Ala Ala Phe Gly
1               5                   10                  15

Leu Thr Leu Leu Leu Ala Ala Leu Arg Pro Ser Ala Ala Tyr Phe Gly
            20                  25                  30

Leu Thr Gly Ser Glu Pro Leu Thr Ile Leu Pro Leu Thr Leu Glu Pro
        35                  40                  45

Glu Ala Ala Ala Gln Ala His Tyr Lys Ala Cys Asp Arg Leu Lys Leu
    50                  55                  60

Glu Arg Lys Gln Arg Arg Met Cys Arg Arg Asp Pro Gly Val Ala Glu
65                  70                  75                  80

Thr Leu Val Glu Ala Val Ser Met Ser Ala Leu Glu Cys Gln Phe Gln
                85                  90                  95

Phe Arg Phe Glu Arg Trp Asn Cys Thr Leu Glu Gly Arg Tyr Arg Ala
            100                 105                 110

Ser Leu Leu Lys Arg Gly Phe Lys Glu Thr Ala Phe Leu Tyr Ala Ile
        115                 120                 125

Ser Ser Ala Gly Leu Thr His Ala Leu Ala Lys Ala Cys Ser Ala Gly
    130                 135                 140

Arg Met Glu Arg Cys Thr Cys Asp Glu Ala Pro Asp Leu Glu Asn Arg
145                 150                 155                 160

Glu Ala Trp Gln Trp Gly Gly Cys Gly Asp Asn Leu Lys Tyr Ser Ser
                165                 170                 175

Lys Phe Val Lys Glu Phe Leu Gly Arg Arg Ser Ser Lys Asp Leu Arg
            180                 185                 190

Ala Arg Val Asp Phe His Asn Asn Leu Val Gly Val Lys Val Ile Lys
        195                 200                 205

Ala Gly Val Glu Thr Thr Cys Lys Cys His Gly Val Ser Gly Ser Cys
    210                 215                 220

Thr Val Arg Thr Cys Trp Arg Gln Leu Ala Pro Phe His Glu Val Gly
225                 230                 235                 240

Lys His Leu Lys His Lys Tyr Glu Thr Ala Leu Lys Val Gly Ser Thr
                245                 250                 255

Thr Asn Glu Ala Ala Gly Glu Ala Gly Ala Ile Ser Pro Pro Arg Gly
            260                 265                 270

Arg Ala Ser Gly Ala Gly Gly Ser Asp Pro Leu Pro Arg Thr Pro Glu
        275                 280                 285

Leu Val His Leu Asp Asp Ser Pro Ser Phe Cys Leu Ala Gly Arg Phe
    290                 295                 300

Ser Pro Gly Thr Ala Gly Arg Arg Cys His Arg Glu Lys Asn Cys Glu
305                 310                 315                 320

Ser Ile Cys Cys Gly Arg Gly His Asn Thr Gln Ser Arg Val Val Thr
                325                 330                 335

Arg Pro Cys Gln Cys Gln Val Arg Trp Cys Cys Tyr Val Glu Cys Arg
            340                 345                 350

Gln Cys Thr Gln Arg Glu Glu Val Tyr Thr Cys Lys Gly
        355                 360                 365

<210> SEQ ID NO 36
<211> LENGTH: 357
<212> TYPE: PRT
<213> ORGANISM: Homo sapiens
```

<400> SEQUENCE: 36

```
Met Arg Pro Pro Pro Ala Leu Ala Leu Ala Gly Leu Cys Leu Leu Ala
1               5                   10                  15

Leu Pro Ala Ala Ala Ala Ser Tyr Phe Gly Leu Thr Gly Arg Glu Val
            20                  25                  30

Leu Thr Pro Phe Pro Gly Leu Gly Thr Ala Ala Ala Pro Ala Gln Gly
        35                  40                  45

Gly Ala His Leu Lys Gln Cys Asp Leu Leu Lys Leu Ser Arg Arg Gln
    50                  55                  60

Lys Gln Leu Cys Arg Arg Glu Pro Gly Leu Ala Glu Thr Leu Arg Asp
65                  70                  75                  80

Ala Ala His Leu Gly Leu Leu Glu Cys Gln Phe Gln Phe Arg His Glu
                85                  90                  95

Arg Trp Asn Cys Ser Leu Glu Gly Arg Met Gly Leu Leu Lys Arg Gly
            100                 105                 110

Phe Lys Glu Thr Ala Phe Leu Tyr Ala Val Ser Ser Ala Ala Leu Thr
        115                 120                 125

His Thr Leu Ala Arg Ala Cys Ser Ala Gly Arg Met Glu Arg Cys Thr
130                 135                 140

Cys Asp Asp Ser Pro Gly Leu Glu Ser Arg Gln Ala Trp Gln Trp Gly
145                 150                 155                 160

Val Cys Gly Asp Asn Leu Lys Tyr Ser Thr Lys Phe Leu Ser Asn Phe
                165                 170                 175

Leu Gly Ser Lys Arg Gly Asn Lys Asp Leu Arg Ala Arg Ala Asp Ala
            180                 185                 190

His Asn Thr His Val Gly Ile Lys Ala Val Lys Ser Gly Leu Arg Thr
        195                 200                 205

Thr Cys Lys Cys His Gly Val Ser Gly Ser Cys Ala Val Arg Thr Cys
210                 215                 220

Trp Lys Gln Leu Ser Pro Phe Arg Glu Thr Gly Gln Val Leu Lys Leu
225                 230                 235                 240

Arg Tyr Asp Ser Ala Val Lys Val Ser Ser Ala Thr Asn Glu Ala Leu
                245                 250                 255

Gly Arg Leu Glu Leu Trp Ala Pro Ala Arg Gln Gly Ser Leu Thr Lys
            260                 265                 270

Gly Leu Ala Pro Arg Ser Gly Asp Leu Val Tyr Met Glu Asp Ser Pro
        275                 280                 285

Ser Phe Cys Arg Pro Ser Lys Tyr Ser Pro Gly Thr Ala Gly Arg Val
    290                 295                 300

Cys Ser Arg Glu Ala Ser Cys Ser Ser Leu Cys Cys Gly Arg Gly Tyr
305                 310                 315                 320

Asp Thr Gln Ser Arg Leu Val Ala Phe Ser Cys His Cys Gln Val Gln
                325                 330                 335

Trp Cys Cys Tyr Val Glu Cys Gln Gln Cys Val Gln Glu Glu Leu Val
            340                 345                 350

Tyr Thr Cys Lys His
        355
```

<210> SEQ ID NO 37
<211> LENGTH: 417
<212> TYPE: PRT
<213> ORGANISM: Homo sapiens

<400> SEQUENCE: 37

```
Met Gly Ser Ala His Pro Arg Pro Trp Leu Arg Leu Arg Pro Gln Pro
1               5                   10                  15
Gln Pro Arg Pro Ala Leu Trp Val Leu Leu Phe Phe Leu Leu Leu Leu
            20                  25                  30
Ala Ala Ala Met Pro Arg Ser Ala Pro Asn Asp Ile Leu Asp Leu Arg
        35                  40                  45
Leu Pro Pro Glu Pro Val Leu Asn Ala Asn Thr Val Cys Leu Thr Leu
50                  55                  60
Pro Gly Leu Ser Arg Arg Gln Met Glu Val Cys Val Arg His Pro Asp
65                  70                  75                  80
Val Ala Ala Ser Ala Ile Gln Gly Ile Gln Ala Ile His Glu Cys
                85                  90                  95
Gln His Gln Phe Arg Asp Gln Arg Trp Asn Cys Ser Ser Leu Glu Thr
                100                 105                 110
Arg Asn Lys Ile Pro Tyr Glu Ser Pro Ile Phe Ser Arg Gly Phe Arg
        115                 120                 125
Glu Ser Ala Phe Ala Tyr Ala Ile Ala Ala Ala Gly Val Val His Ala
    130                 135                 140
Val Ser Asn Ala Cys Ala Leu Gly Lys Leu Lys Ala Cys Gly Cys Asp
145                 150                 155                 160
Ala Ser Arg Arg Gly Asp Glu Glu Ala Phe Arg Arg Lys Leu His Arg
                165                 170                 175
Leu Gln Leu Asp Ala Leu Gln Arg Gly Lys Gly Leu Ser His Gly Val
            180                 185                 190
Pro Glu His Pro Ala Leu Pro Thr Ala Ser Pro Gly Leu Gln Asp Ser
        195                 200                 205
Trp Glu Trp Gly Gly Cys Ser Pro Asp Met Gly Phe Gly Glu Arg Phe
    210                 215                 220
Ser Lys Asp Phe Leu Asp Ser Arg Glu Pro His Arg Asp Ile His Ala
225                 230                 235                 240
Arg Met Arg Leu His Asn Asn Arg Val Gly Arg Gln Ala Val Met Glu
                245                 250                 255
Asn Met Arg Arg Lys Cys Lys Cys His Gly Thr Ser Gly Ser Cys Gln
            260                 265                 270
Leu Lys Thr Cys Trp Gln Val Thr Pro Glu Phe Arg Thr Val Gly Ala
        275                 280                 285
Leu Leu Arg Ser Arg Phe His Arg Ala Thr Leu Ile Arg Pro His Asn
    290                 295                 300
Arg Asn Gly Gly Gln Leu Glu Pro Gly Pro Ala Gly Ala Pro Ser Pro
305                 310                 315                 320
Ala Pro Gly Ala Pro Gly Pro Arg Arg Arg Ala Ser Pro Ala Asp Leu
                325                 330                 335
Val Tyr Phe Glu Lys Ser Pro Asp Phe Cys Glu Arg Glu Pro Arg Leu
            340                 345                 350
Asp Ser Ala Gly Thr Val Gly Arg Leu Cys Asn Lys Ser Ser Ala Gly
        355                 360                 365
Ser Asp Gly Cys Gly Ser Met Cys Cys Gly Arg Gly His Asn Ile Leu
    370                 375                 380
Arg Gln Thr Arg Ser Glu Arg Cys His Cys Arg Phe His Trp Cys Cys
385                 390                 395                 400
Phe Val Val Cys Glu Glu Cys Arg Ile Thr Glu Trp Val Ser Val Cys
                405                 410                 415
```

Lys

<210> SEQ ID NO 38
<211> LENGTH: 389
<212> TYPE: PRT
<213> ORGANISM: Homo sapiens

<400> SEQUENCE: 38

Met Leu Glu Glu Pro Arg Pro Arg Pro Pro Ser Gly Leu Ala Gly
1               5                   10                  15

Leu Leu Phe Leu Ala Leu Cys Ser Arg Ala Leu Ser Asn Glu Ile Leu
            20                  25                  30

Gly Leu Lys Leu Pro Gly Glu Pro Leu Thr Ala Asn Thr Val Cys
            35                  40                  45

Leu Thr Leu Ser Gly Leu Ser Lys Arg Gln Leu Gly Leu Cys Leu Arg
    50                  55                  60

Asn Pro Asp Val Thr Ala Ser Ala Leu Gln Gly Leu His Ile Ala Val
65              70                  75                  80

His Glu Cys Gln His Gln Leu Arg Asp Gln Arg Trp Asn Cys Ser Ala
                85                  90                  95

Leu Glu Gly Gly Gly Arg Leu Pro His His Ser Ala Ile Leu Lys Arg
            100                 105                 110

Gly Phe Arg Glu Ser Ala Phe Ser Phe Ser Met Leu Ala Ala Gly Val
            115                 120                 125

Met His Ala Val Ala Thr Ala Cys Ser Leu Gly Lys Leu Val Ser Cys
130                 135                 140

Gly Cys Gly Trp Lys Gly Ser Gly Glu Gln Asp Arg Leu Arg Ala Lys
145                 150                 155                 160

Leu Leu Gln Leu Gln Ala Leu Ser Arg Gly Lys Ser Phe Pro His Ser
                165                 170                 175

Leu Pro Ser Pro Gly Pro Gly Ser Ser Pro Ser Pro Gly Pro Gln Asp
            180                 185                 190

Thr Trp Glu Trp Gly Gly Cys Asn His Asp Met Asp Phe Gly Glu Lys
            195                 200                 205

Phe Ser Arg Asp Phe Leu Asp Ser Arg Glu Ala Pro Arg Asp Ile Gln
    210                 215                 220

Ala Arg Met Arg Ile His Asn Asn Arg Val Gly Arg Gln Val Val Thr
225                 230                 235                 240

Glu Asn Leu Lys Arg Lys Cys Lys Cys His Gly Thr Ser Gly Ser Cys
                245                 250                 255

Gln Phe Lys Thr Cys Trp Arg Ala Ala Pro Glu Phe Arg Ala Val Gly
            260                 265                 270

Ala Ala Leu Arg Glu Arg Leu Gly Arg Ala Ile Phe Ile Asp Thr His
            275                 280                 285

Asn Arg Asn Ser Gly Ala Phe Gln Pro Arg Leu Arg Pro Arg Arg Leu
290                 295                 300

Ser Gly Glu Leu Val Tyr Phe Glu Lys Ser Pro Asp Phe Cys Glu Arg
305                 310                 315                 320

Asp Pro Thr Met Gly Ser Pro Gly Thr Arg Gly Arg Ala Cys Asn Lys
                325                 330                 335

Thr Ser Arg Leu Leu Asp Gly Cys Gly Ser Leu Cys Cys Gly Arg Gly
            340                 345                 350

His Asn Val Leu Arg Gln Thr Arg Val Glu Arg Cys His Cys Arg Phe
            355                 360                 365

```
His Trp Cys Cys Tyr Val Leu Cys Asp Glu Cys Lys Val Thr Glu Trp
    370                 375                 380

Val Asn Val Cys Lys
385

<210> SEQ ID NO 39
<211> LENGTH: 354
<212> TYPE: PRT
<213> ORGANISM: Homo sapiens

<400> SEQUENCE: 39

Met Arg Ala Arg Pro Gln Val Cys Glu Ala Leu Leu Phe Ala Leu Ala
1               5                   10                  15

Leu Gln Thr Gly Val Cys Tyr Gly Ile Lys Trp Leu Ala Leu Ser Lys
            20                  25                  30

Thr Pro Ser Ala Leu Ala Leu Asn Gln Thr Gln His Cys Lys Gln Leu
        35                  40                  45

Glu Gly Leu Val Ser Ala Gln Val Gln Leu Cys Arg Ser Asn Leu Glu
    50                  55                  60

Leu Met His Thr Val Val His Ala Ala Arg Glu Val Met Lys Ala Cys
65                  70                  75                  80

Arg Arg Ala Phe Ala Asp Met Arg Trp Asn Cys Ser Ser Ile Glu Leu
                85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ala Ile Ser His Ala Ile Ala Arg
        115                 120                 125

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300

Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
                325                 330                 335

Cys Tyr Val Thr Cys Arg Arg Cys Glu Arg Thr Val Glu Arg Tyr Val
            340                 345                 350
```

Cys Lys

<210> SEQ ID NO 40
<211> LENGTH: 365
<212> TYPE: PRT
<213> ORGANISM: Homo sapiens

<400> SEQUENCE: 40

```
Met Asp Arg Ala Ala Leu Leu Gly Leu Ala Arg Leu Cys Ala Leu Trp
1               5                   10                  15

Ala Ala Leu Leu Val Leu Phe Pro Tyr Gly Ala Gln Gly Asn Trp Met
            20                  25                  30

Trp Leu Gly Ile Ala Ser Phe Gly Val Pro Glu Lys Leu Gly Cys Ala
        35                  40                  45

Asn Leu Pro Leu Asn Ser Arg Gln Lys Glu Leu Cys Lys Arg Lys Pro
    50                  55                  60

Tyr Leu Leu Pro Ser Ile Arg Glu Gly Ala Arg Leu Gly Ile Gln Glu
65                  70                  75                  80

Cys Gly Ser Gln Phe Arg His Glu Arg Trp Asn Cys Met Ile Thr Ala
                85                  90                  95

Ala Ala Thr Thr Ala Pro Met Gly Ala Ser Pro Leu Phe Gly Tyr Glu
            100                 105                 110

Leu Ser Ser Gly Thr Lys Glu Thr Ala Phe Ile Tyr Ala Val Met Ala
        115                 120                 125

Ala Gly Leu Val His Ser Val Thr Arg Ser Cys Ser Ala Gly Asn Met
    130                 135                 140

Thr Glu Cys Ser Cys Asp Thr Thr Leu Gln Asn Gly Gly Ser Ala Ser
145                 150                 155                 160

Glu Gly Trp His Trp Gly Gly Cys Ser Asp Asp Val Gln Tyr Gly Met
                165                 170                 175

Trp Phe Ser Arg Lys Phe Leu Asp Phe Pro Ile Gly Asn Thr Thr Gly
            180                 185                 190

Lys Glu Asn Lys Val Leu Leu Ala Met Asn Leu His Asn Asn Glu Ala
        195                 200                 205

Gly Arg Gln Ala Val Ala Lys Leu Met Ser Val Asp Cys Arg Cys His
    210                 215                 220

Gly Val Ser Gly Ser Cys Ala Val Lys Thr Cys Trp Lys Thr Met Ser
225                 230                 235                 240

Ser Phe Glu Lys Ile Gly His Leu Leu Lys Asp Lys Tyr Glu Asn Ser
                245                 250                 255

Ile Gln Ile Ser Asp Lys Thr Lys Arg Lys Met Arg Arg Arg Glu Lys
            260                 265                 270

Asp Gln Arg Lys Ile Pro Ile His Lys Asp Asp Leu Leu Tyr Val Asn
        275                 280                 285

Lys Ser Pro Asn Tyr Cys Val Glu Asp Lys Lys Leu Gly Ile Pro Gly
    290                 295                 300

Thr Gln Gly Arg Glu Cys Asn Arg Thr Ser Glu Gly Ala Asp Gly Cys
305                 310                 315                 320

Asn Leu Leu Cys Cys Gly Arg Gly Tyr Asn Thr His Val Arg Arg His
                325                 330                 335

Val Glu Arg Cys Glu Cys Lys Phe Ile Trp Cys Cys Tyr Val Arg Cys
            340                 345                 350

Arg Arg Cys Glu Ser Met Thr Asp Val His Thr Cys Lys
        355                 360                 365
```

```
<210> SEQ ID NO 41
<211> LENGTH: 31
<212> TYPE: DNA
<213> ORGANISM: Homo sapiens
<220> FEATURE:
<221> NAME/KEY: misc_feature
<222> LOCATION: (1)..(31)
<223> OTHER INFORMATION: Forward primer

<400> SEQUENCE: 41
gcatggatcc accatgaacc ggaaagcgcg g                              31

<210> SEQ ID NO 42
<211> LENGTH: 34
<212> TYPE: DNA
<213> ORGANISM: Homo sapiens
<220> FEATURE:
<221> NAME/KEY: misc_feature
<222> LOCATION: (1)..(34)
<223> OTHER INFORMATION: Reverse primer

<400> SEQUENCE: 42
gcatgcggcc gctcacttgc acgtgtacat ctcc                           34

<210> SEQ ID NO 43
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: Forward primer

<400> SEQUENCE: 43
atgggcctgg acgaggccca gtttcagttc cgc                            33

<210> SEQ ID NO 44
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: Reverse primer

<400> SEQUENCE: 44
gcggaactga aactgggcct cgtccaggcc cat                            33

<210> SEQ ID NO 45
<211> LENGTH: 28
<212> TYPE: DNA
<213> ORGANISM: Homo sapiens
<220> FEATURE:
<221> NAME/KEY: misc_feature
<222> LOCATION: (1)..(28)
<223> OTHER INFORMATION: Forward primer

<400> SEQUENCE: 45
gtgccacggc gtggcaggct cgtgcacc                                  28

<210> SEQ ID NO 46
<211> LENGTH: 28
<212> TYPE: DNA
<213> ORGANISM: Homo sapiens
<220> FEATURE:
<221> NAME/KEY: misc_feature
<222> LOCATION: (1)..(28)
```

```
<223> OTHER INFORMATION: Reverse primer

<400> SEQUENCE: 46
ggtgcacgag cctgccacgc cgtggcac                                             28
```